(12) United States Patent
Vito et al.

(10) Patent No.: US 8,297,601 B2
(45) Date of Patent: Oct. 30, 2012

(54) VIBRATION DAMPENING MATERIAL AND METHOD OF MAKING SAME

(75) Inventors: Robert A. Vito, Berwyn, PA (US);
Carmen N. DiMario, West Chester, PA (US); Thomas Falone, Mickleton, NJ (US)

(73) Assignee: Matscitechno Licensing Company, Kennett Square, PA (US)

( * ) Notice: Subject to any disclaimer, the term of this patent is extended or adjusted under 35 U.S.C. 154(b) by 0 days.

(21) Appl. No.: 12/324,281

(22) Filed: Nov. 26, 2008

(65) Prior Publication Data

US 2009/0179361 A1 Jul. 16, 2009

Related U.S. Application Data

(60) Continuation of application No. 11/304,995, filed on Dec. 15, 2005, now abandoned, which is a continuation-in-part of application No. 11/019,568, filed on Dec. 22, 2004, now Pat. No. 7,171,697, which is a continuation-in-part of application No. 10/999,246, filed on Nov. 30, 2004, now abandoned, which is a continuation-in-part of application No. 10/958,611, filed on Oct. 5, 2004, now Pat. No. 7,150,113, which is a continuation-in-part of application No. 10/856,215, filed on May 28, 2004, now Pat. No. 6,942,586, which is a continuation of application No. 10/659,560, filed on Sep. 10, 2003, now Pat. No. 6,935,973, which is a division of application No. 09/939,319, filed on Aug. 27, 2001, now Pat. No. 6,652,398.

(51) Int. Cl.
*F16M 5/00* (2006.01)
*F16F 3/087* (2006.01)

(52) U.S. Cl. .............. 267/140.11; 267/140.3; 267/148; 267/152

(58) Field of Classification Search .............. 267/136, 267/140.11, 140.12, 140.3, 140.4, 148, 149, 267/151, 152, 292, 293
See application file for complete search history.

(56) References Cited

U.S. PATENT DOCUMENTS

| | | |
|---|---|---|
| 1,125,029 A | 1/1915 | Lard |
| 1,195,994 A | 8/1916 | Lard |
| 1,498,838 A | 6/1924 | Harrison, Jr. |
| 1,551,203 A | 8/1925 | Mills |
| 1,620,118 A | 3/1927 | Mattern |
| 1,701,856 A | 2/1929 | Kraeuter |
| 1,772,414 A * | 8/1930 | Brooke-Hunt et al. ........ 267/293 |
| 2,023,131 A | 12/1935 | Gibson |
| 2,099,521 A | 11/1937 | Herkimer et al. |
| 2,871,899 A | 2/1959 | Coyle et al. |

(Continued)

FOREIGN PATENT DOCUMENTS

DE 2805314 8/1979

(Continued)

OTHER PUBLICATIONS

Technical Guide, Kevlar, Aramid Fiber, DuPont, Apr. 2000.*

(Continued)

*Primary Examiner* — Thomas J Williams
(74) *Attorney, Agent, or Firm* — RatnerPrestia

(57) ABSTRACT

The present invention is directed to a material adapted to reduce vibration and, more specifically, to a material adapted to dissipate and evenly distribute transmitted vibrations. The material is particularly suited for impact and/or heavy load vibration resistance.

15 Claims, 40 Drawing Sheets

U.S. PATENT DOCUMENTS

| | | | |
|---|---|---|---|
| 3,515,625 A | 4/1965 | Sedlak et al. | |
| 3,353,981 A | 11/1967 | Jacob | |
| 3,398,233 A * | 8/1968 | Otano et al. | 174/110 R |
| 3,606,326 A | 9/1971 | Sparks et al. | |
| 3,716,433 A | 2/1973 | Plummer | |
| 3,730,509 A | 5/1973 | Jorn | |
| 3,779,551 A | 12/1973 | Wilson | |
| 3,791,050 A | 2/1974 | Egtvedt | |
| 3,862,882 A | 1/1975 | Marzocchi | |
| 4,015,851 A | 4/1977 | Pennell | |
| 4,044,625 A | 8/1977 | D'Haem et al. | |
| 4,134,198 A | 1/1979 | Briggs | |
| 4,143,109 A | 3/1979 | Stockum | |
| 4,147,443 A | 4/1979 | Skobel | |
| 4,197,611 A | 4/1980 | Bell et al. | |
| 4,237,177 A | 12/1980 | Siama et al. | |
| 4,261,567 A | 4/1981 | Uffindell | |
| 4,268,574 A | 5/1981 | Peccenini et al. | |
| 4,338,270 A | 7/1982 | Uffindell | |
| 4,347,280 A | 8/1982 | Lau et al. | |
| 4,417,042 A | 11/1983 | Dziark | |
| 4,483,972 A | 11/1984 | Mitchell | |
| 4,504,991 A | 3/1985 | Klancnik | |
| 4,526,828 A | 7/1985 | Fogt et al. | |
| 4,552,713 A | 11/1985 | Cavicchioli | |
| 4,575,446 A | 3/1986 | Schaefer | |
| 4,584,232 A | 4/1986 | Frank et al. | |
| 4,591,160 A | 5/1986 | Piragino | |
| 4,597,578 A | 7/1986 | Lancaster | |
| 4,613,537 A | 9/1986 | Krupper | |
| 4,660,832 A | 4/1987 | Shomo | |
| 4,706,788 A * | 11/1987 | Inman et al. | 188/378 |
| 4,736,949 A | 4/1988 | Muroi | |
| 4,819,939 A | 4/1989 | Kobayashi | |
| 4,864,738 A | 9/1989 | Horovitz | |
| 4,912,836 A | 4/1990 | Avetoom | |
| 4,919,420 A | 4/1990 | Sato | |
| 4,948,131 A | 8/1990 | Nakanishi | |
| 4,953,862 A | 9/1990 | Uke et al. | |
| 4,983,242 A | 1/1991 | Reed | |
| 4,989,643 A | 2/1991 | Walton et al. | |
| 5,005,254 A | 4/1991 | Uffindell | |
| 5,042,804 A | 8/1991 | Uke et al. | |
| 5,083,780 A | 1/1992 | Walton et al. | |
| 5,087,491 A * | 2/1992 | Barrett | 248/636 |
| 5,088,734 A | 2/1992 | Glava | |
| 5,110,653 A | 5/1992 | Landi | |
| 5,122,405 A | 6/1992 | Landi | |
| 5,137,769 A | 8/1992 | Landi | |
| 5,193,246 A | 3/1993 | Huang | |
| 5,199,706 A | 4/1993 | Chen | |
| 5,203,561 A | 4/1993 | Lanctot | |
| 5,240,247 A | 8/1993 | Didier | |
| 5,254,391 A | 10/1993 | Davis | |
| 5,258,088 A | 11/1993 | Wu | |
| 5,261,665 A | 11/1993 | Downey | |
| 5,267,487 A | 12/1993 | Falco et al. | |
| 5,269,516 A | 12/1993 | Janes | |
| 5,282,618 A | 2/1994 | Hong | |
| 5,290,036 A | 3/1994 | Fenton et al. | |
| 5,294,119 A | 3/1994 | Vincent et al. | |
| 5,308,675 A * | 5/1994 | Crane et al. | 267/141.1 |
| 5,319,867 A | 6/1994 | Weber | |
| 5,322,280 A | 6/1994 | Wu | |
| 5,322,285 A | 6/1994 | Turner | |
| 5,322,290 A | 6/1994 | Minami | |
| 5,333,861 A | 8/1994 | Mills | |
| 5,338,600 A | 8/1994 | Fitchmun et al. | |
| 5,339,793 A | 8/1994 | Findley | |
| 5,348,303 A | 9/1994 | Swissheim | |
| 5,355,552 A | 10/1994 | Huang | |
| 5,360,653 A | 11/1994 | Ackley | |
| 5,362,046 A | 11/1994 | Sims | |
| 5,377,979 A | 1/1995 | Long | |
| 5,384,083 A | 1/1995 | Dawn et al. | |
| 5,395,108 A | 3/1995 | Souders et al. | |
| 5,435,549 A | 7/1995 | Chen | |
| 5,463,824 A | 11/1995 | Barna | |
| 5,511,777 A | 4/1996 | McNeely | |
| 5,516,101 A | 5/1996 | Peng | |
| 5,524,885 A | 6/1996 | Heo | |
| 5,528,842 A | 6/1996 | Ricci et al. | |
| 5,547,189 A | 8/1996 | Billlings | |
| 5,575,473 A | 11/1996 | Turner | |
| 5,593,158 A | 1/1997 | Filice et al. | |
| 5,621,914 A | 4/1997 | Ramone et al. | |
| 5,624,114 A | 4/1997 | Kelsey | |
| D379,208 S | 5/1997 | Kulisek, Jr. | |
| 5,636,377 A | 6/1997 | Wiener | |
| 5,653,643 A | 8/1997 | Falone et al. | |
| 5,655,975 A | 8/1997 | Nashif | |
| 5,657,985 A | 8/1997 | Dahlstrom et al. | |
| 5,673,437 A | 10/1997 | Chase et al. | |
| 5,686,158 A | 11/1997 | Gibbon | |
| 5,695,408 A | 12/1997 | DeLaCruz | |
| 5,718,064 A | 2/1998 | Pyle | |
| 5,730,662 A | 3/1998 | Rens | |
| 5,749,798 A | 5/1998 | Kuebler et al. | |
| 5,759,113 A | 6/1998 | Lai et al. | |
| 5,772,524 A | 6/1998 | Huang | |
| 5,789,327 A | 8/1998 | Rousseau | |
| 5,840,397 A | 11/1998 | Landi et al. | |
| 5,842,933 A | 12/1998 | Lewis | |
| 5,843,851 A | 12/1998 | Cochran | |
| 5,858,521 A | 1/1999 | Okuda et al. | |
| 5,912,195 A | 6/1999 | Walla et al. | |
| 5,916,664 A | 6/1999 | Rudy | |
| 5,926,847 A | 7/1999 | Eibert | |
| 5,944,617 A | 8/1999 | Falone et al. | |
| 5,946,734 A | 9/1999 | Vogan | |
| 5,963,989 A | 10/1999 | Robertson | |
| 5,979,081 A | 11/1999 | Vaz | |
| 6,000,062 A | 12/1999 | Trakh | |
| 6,007,439 A | 12/1999 | MacKay, Jr. | |
| 6,074,965 A | 6/2000 | Bodenschatz et al. | |
| 6,077,793 A | 6/2000 | Hatjasalo et al. | |
| 6,167,639 B1 | 1/2001 | Ventura | |
| 6,216,276 B1 | 4/2001 | Eibert | |
| 6,219,940 B1 | 4/2001 | Kita | |
| 6,231,946 B1 | 5/2001 | Brown, Jr. et al. | |
| 6,251,493 B1 * | 6/2001 | Johnson et al. | 428/71 |
| 6,318,002 B1 | 11/2001 | Ou | |
| 6,368,989 B1 | 4/2002 | Pascual et al. | |
| 6,416,432 B1 | 7/2002 | Rosen et al. | |
| 6,505,421 B1 | 1/2003 | Vaz | |
| 6,520,491 B2 * | 2/2003 | Timlick | 267/113 |
| 6,558,270 B2 | 5/2003 | Kwitek | |
| 6,578,836 B2 | 6/2003 | Kogure et al. | |
| 6,880,269 B2 | 4/2005 | Falone et al. | |
| 6,928,658 B2 | 8/2005 | Taira et al. | |
| 6,944,974 B2 | 9/2005 | Falone et al. | |
| 6,969,548 B1 | 11/2005 | Goldfine | |
| 2001/0008053 A1 | 7/2001 | Belli | |
| 2001/0055994 A1 | 12/2001 | Kwitek | |
| 2002/0144432 A1 | 10/2002 | Dennis et al. | |
| 2003/0070209 A1 | 4/2003 | Falone et al. | |
| 2003/0228816 A1 * | 12/2003 | Vito et al. | 442/169 |
| 2004/0048701 A1 | 3/2004 | Falone et al. | |
| 2004/0168355 A1 | 9/2004 | Biwand et al. | |
| 2005/0114985 A1 | 6/2005 | Falone et al. | |
| 2005/0132614 A1 | 6/2005 | Brennan | |
| 2005/0144808 A1 | 7/2005 | Vito et al. | |

FOREIGN PATENT DOCUMENTS

| | | |
|---|---|---|
| DE | 93 12 305 U1 | 10/1993 |
| EP | 0374597 | 6/1990 |
| GB | 458367 | 6/1935 |
| KR | 10-2000-0022092 | 4/2000 |
| WO | WO 9100966 | 1/1991 |
| WO | WO 03018144 | 3/2003 |
| WO | WO 03032762 | 4/2003 |
| WO | WO 03066174 | 8/2003 |

OTHER PUBLICATIONS

Technical Product Data Sheet, Nylon 6/6, Nylon 6/6 GF-30.*
Database WIP Week 198711, Derwent Publications Ltd., London, GB; AN 1987-075332, Feb. 5, 1987 (Abstract).

Benjamin Tang, Fiber Reinforced Polymer Composites Applicatiaon in USA, Jan. 6, 1997, DOT—Federal Highway Administration.

Office Action with Search Report for Taiwanese Patent Application No. 095146948 dated Jan. 11, 2012 (with English translation).

Notice of Second Office Action for PRC Patent Application No. 200580039447.9 issued on Nov. 9, 2011 (with English Translation).

Korean Office Action for application No. KR 10-2011-7005051 mailed Feb. 29, 2012.

USPTO Office Action issued for U.S. Appl. No. 12/570,499 mailed May 30, 2012.

Supplemental European Search Report for EPO 05809057.2 mailed May 11, 2012.

Taiwanese Notification of First Office Action for Taiwanese Patent Application 094134880 mailed May 21, 2012.

* cited by examiner

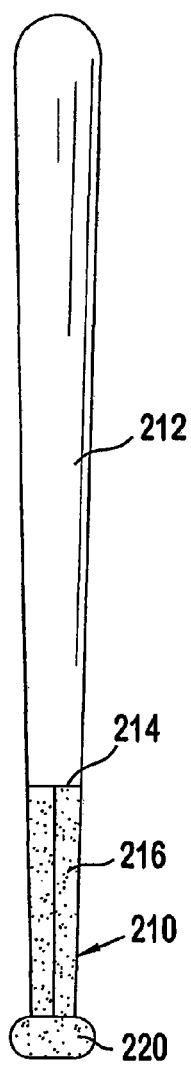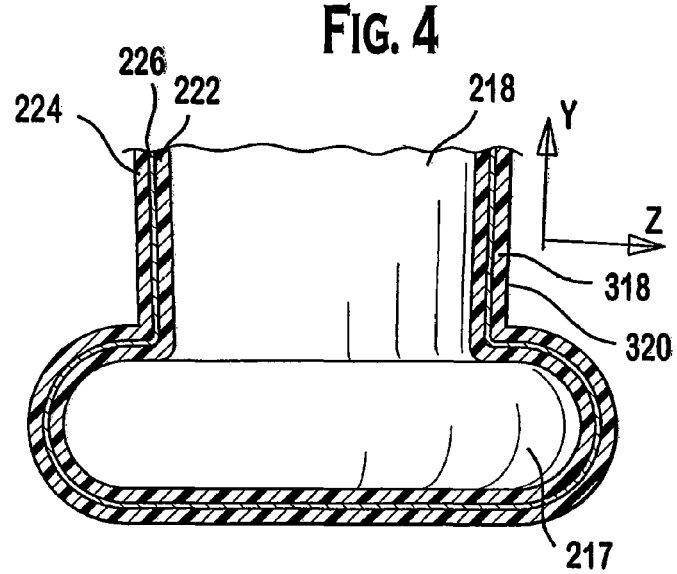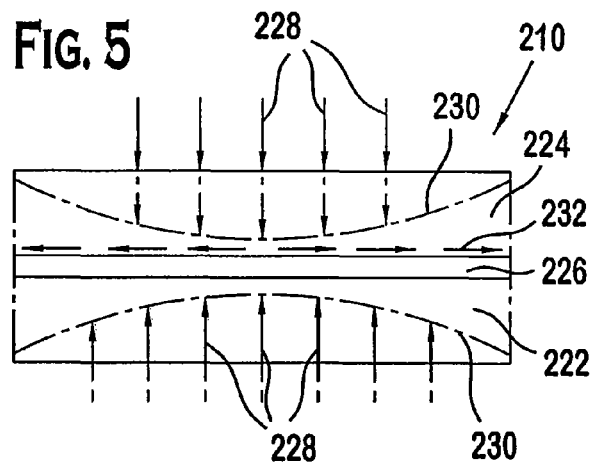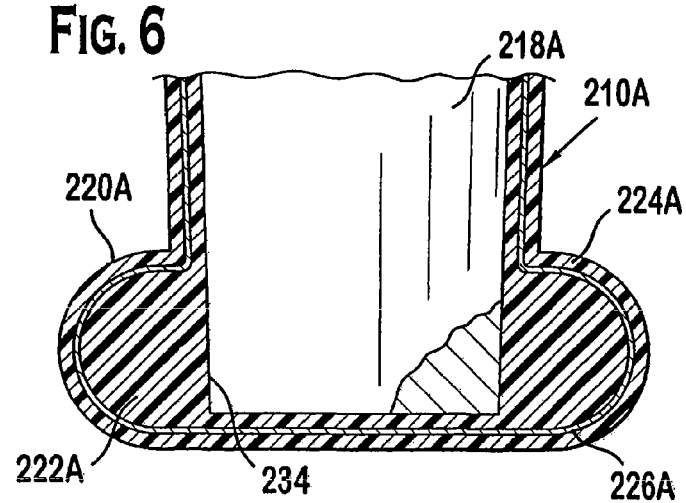

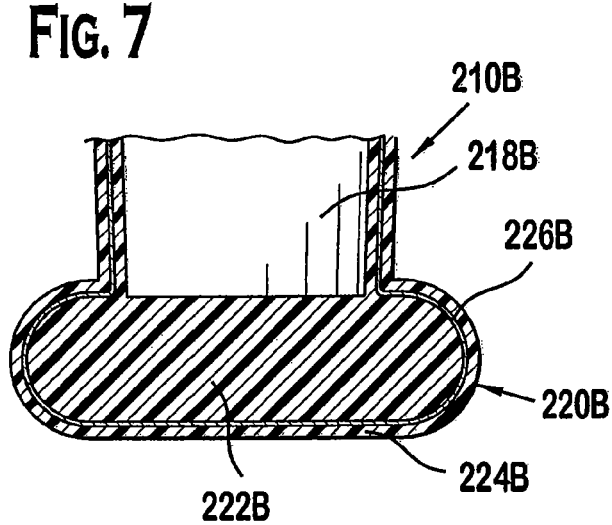
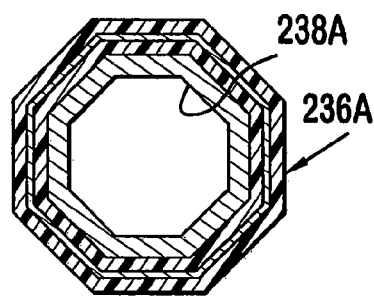
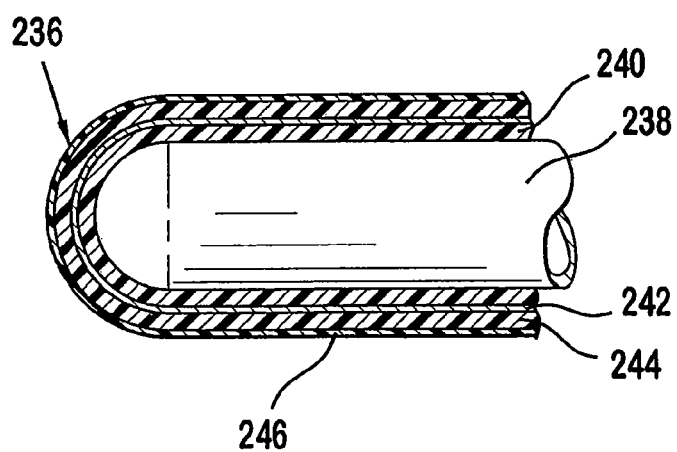
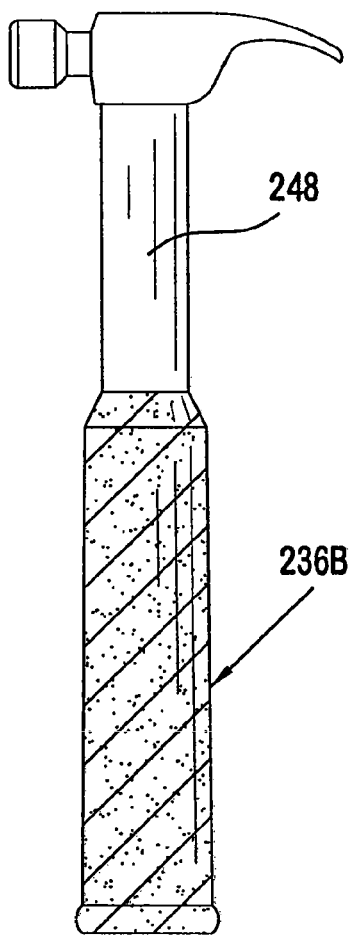

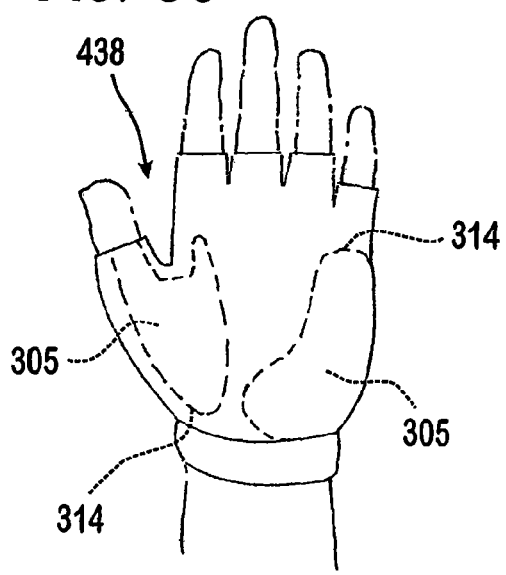
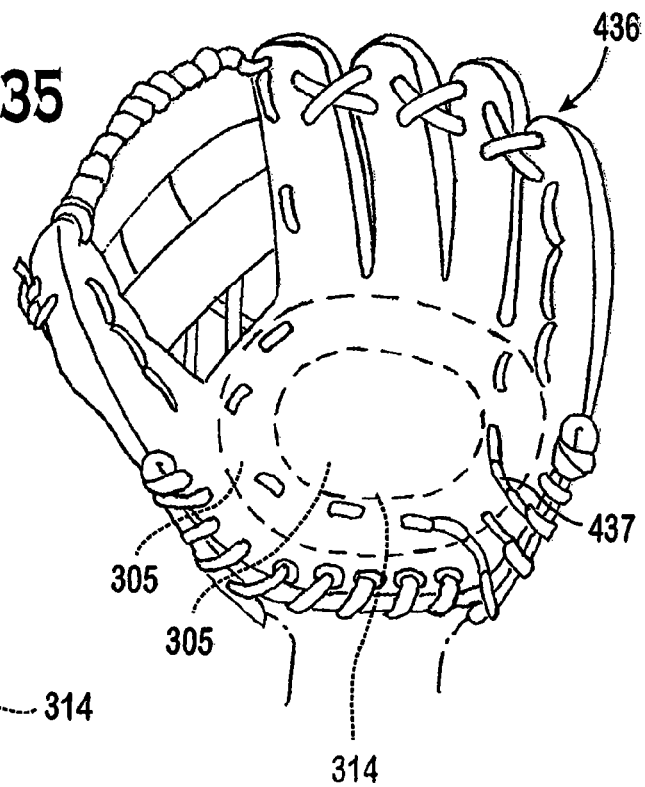
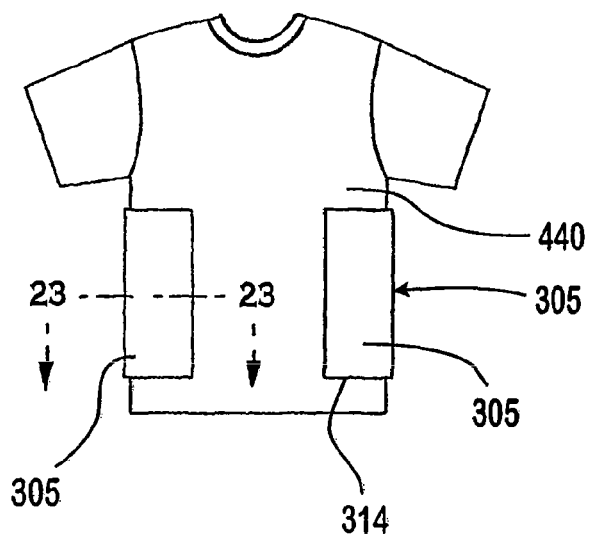

FIG. 38
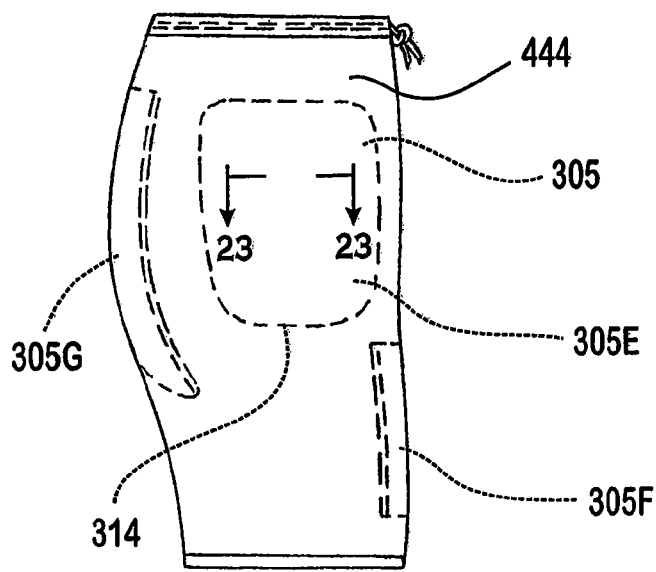
FIG. 39
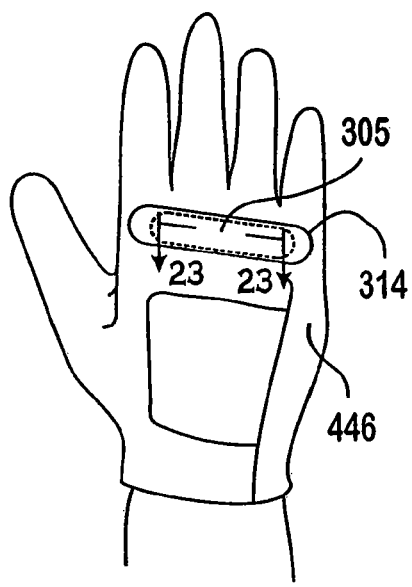
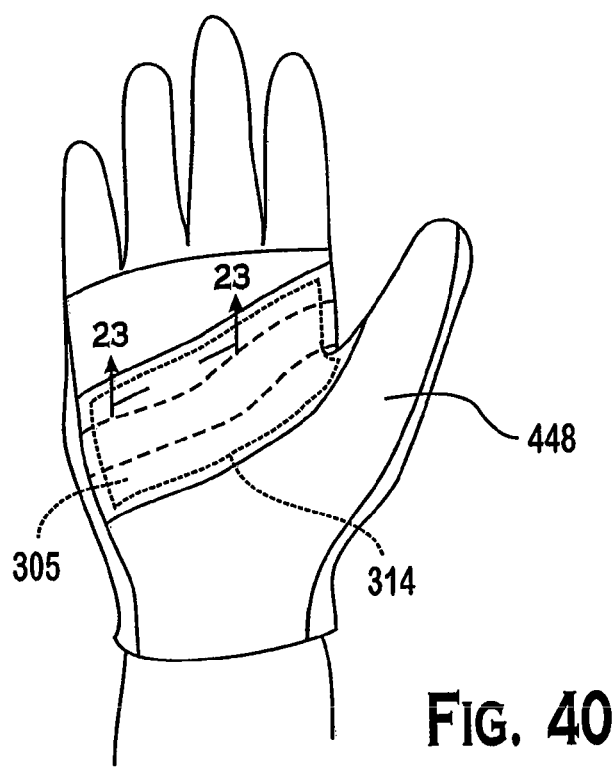
FIG. 40

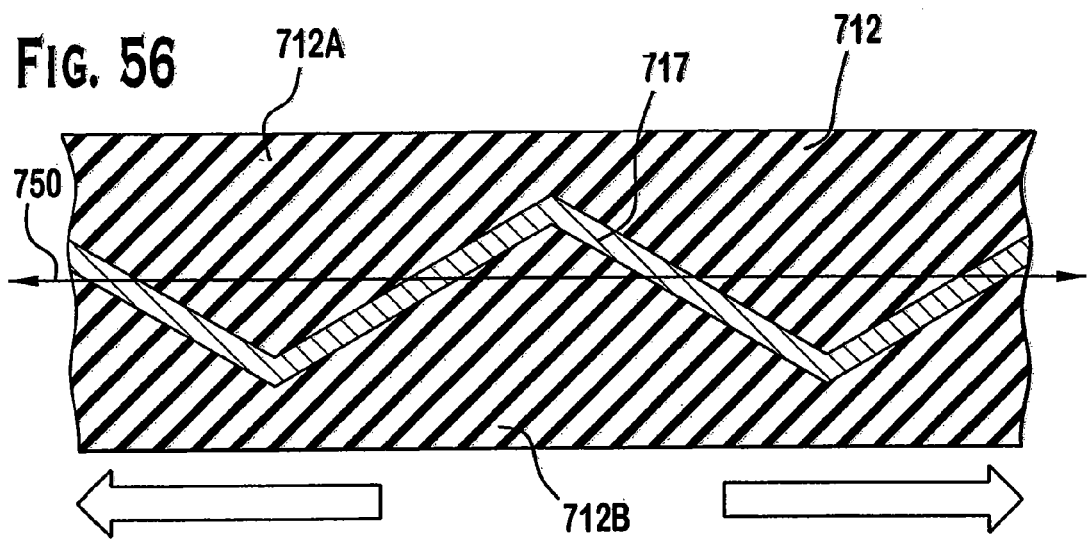
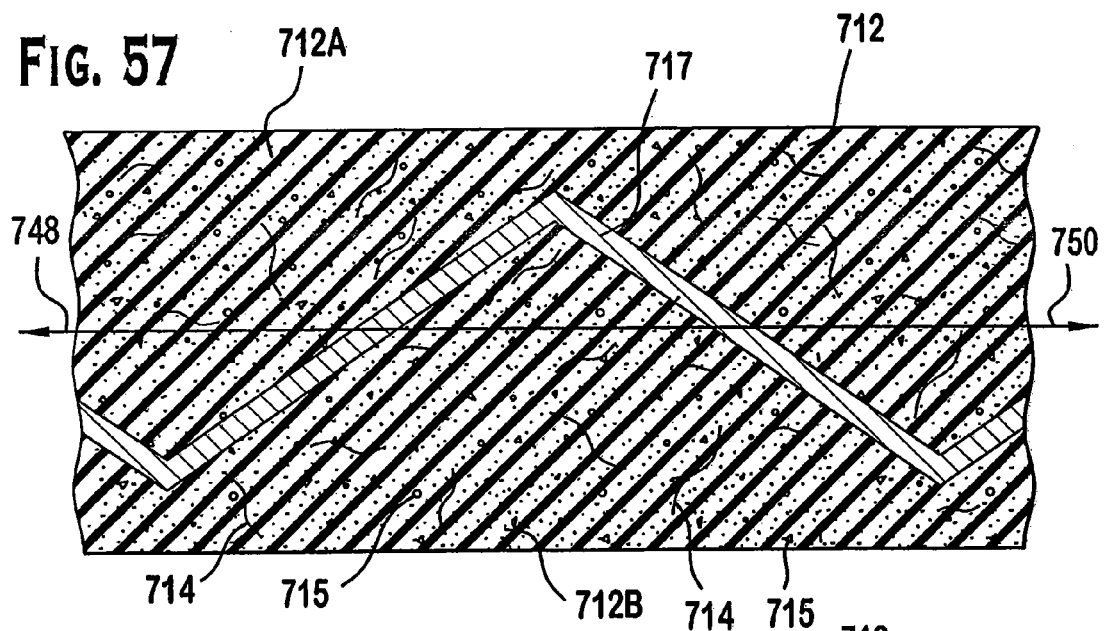
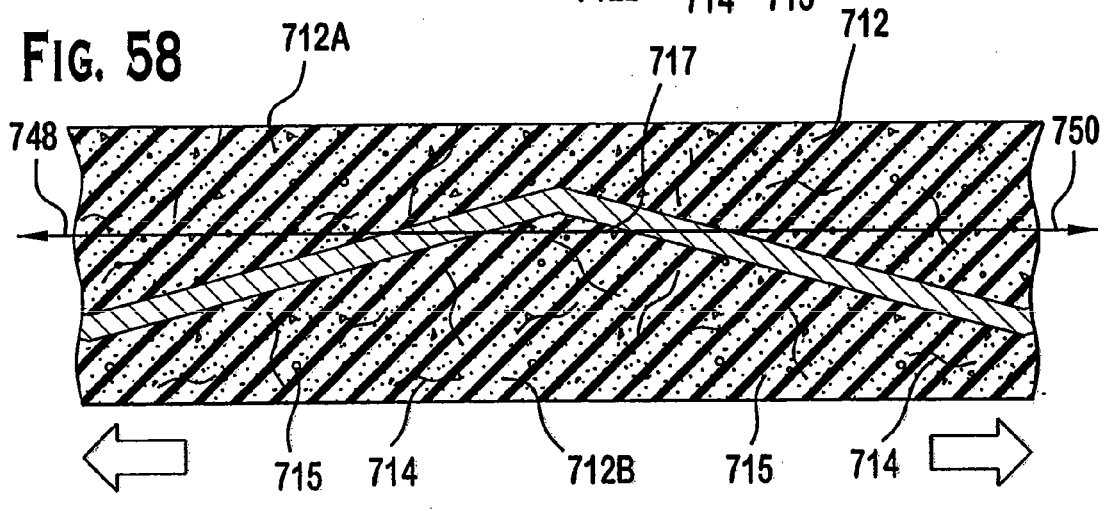

1130

VIBRATION DAMPENING MATERIAL AND METHOD OF MAKING SAME

CROSS REFERENCE TO RELATED APPLICATION(S)

This application is a continuation of U.S. patent application Ser. No. 11/304,995, filed Dec. 15, 2005, which a is a continuation in part of and claims priority to U.S. patent application Ser. No. 11/019,568, filed Dec. 22, 2004, which claims the benefit of priority to U.S. patent application Ser. No. 10/999,246, filed Nov. 30, 2004, which is a continuation in part of and claims priority to U.S. patent application Ser. No. 10/958,611, filed Oct. 5, 2004, which is a continuation in part of and claims priority to U.S. patent application Ser. No. 10/856,215, filed May 28, 2004, which is a continuation of and claims priority to U.S. patent application Ser. No. 10/659,560, filed Sep. 10, 2003, which is a divisional of and claims priority to U.S. patent application Ser. No. 09/939,319, filed on Aug. 27, 2001, now U.S. Pat. No. 6,652,398; this application also claims priority to each of U.S. patent application Ser. Nos. 10/958,941, 10/958,767, 10/958,952, 10/958,745, 10/999,246; priority to each of the above identified applications is claimed and each of the above identified applications is hereby incorporated by reference herein as if fully set forth in its entirety, which are incorporated by reference as if fully set forth.

BACKGROUND

The present invention is directed to a material adapted to reduce vibration and, more specifically, to a material adapted to dissipate and evenly distribute vibrations transmitted.

Repetitive contact and excessive vibrations can injure a person or damage equipment. What is needed is a vibration dissipating material adapted to regulate vibration that provides the necessary rigidity for effective vibration distribution; that can dampen and reduce vibrational energy; and that exhibits superior vibration dissipation.

SUMMARY

One embodiment of the present invention is directed to materials for use in items that regulate and dissipate vibration. Each of the materials, and then their uses on certain items will be described first in summary, and then in detail.

The first material comprises first and second elastomer layers; and a reinforcement layer disposed between and generally separating the first and second elastomer layers. The reinforcement layer comprising a layer of high tensile strength fibrous material.

The second material comprises first and second elastomer layers and a reinforcement layer disposed between and generally separating the first and second elastomer layers. The reinforcement layer has a plurality of high tensile strength fibrous material connected to the first and second elastomer layers and located between the first and second elastomer layers. The high tensile strength fibrous material is generally compliant only in a direction generally perpendicular to the major material surface so as to be generally non energy storing in the direction. The high tensile strength fibrous material is also generally interlocked in and generally held in position by the first and second elastomer layers. Finally, the high tensile strength fibrous material generally distributes impact energy parallel to the major material surface and into the first and second elastomer layers.

The third material comprises a first elastomeric layer of vibration absorbing material which is substantially free of voids therein; a second elastomeric layer which includes an aramid material therein and that is disposed on the first elastomeric layer, wherein the aramid material distributes vibration to facilitate vibration dampening; and a third elastomeric layer disposed on the second elastomeric layer and adapted for gripping.

The fourth material comprises a first elastomeric layer adapted to absorb vibration, the first elastomeric layer being substantially free of voids therein;
   a second elastomeric layer which includes an aramid material therein and that is disposed on the first elastomeric layer, the aramid material comprising a plurality of individual strips of aramid of different sizes, wherein the aramid material distributes vibration to facilitate vibration dampening, the second elastomeric layer being substantially free of voids therein; and
   a third elastomeric layer that is disposed on the second elastomeric layer, the third elastomeric layer being substantially free of voids.

The fifth material comprises: a first elastomeric layer of vibration absorbing material which is substantially free of voids therein; a second elastomeric layer that includes an aramid material therein and that is disposed on the first elastomeric layer, wherein the aramid material distributes vibration to facilitate vibration dampening; and a third elastomeric layer disposed on the second elastomeric layer.

The sixth material comprises: a first elastomeric layer adapted to absorb vibration, the first elastomeric layer being substantially free of voids therein;
   a second elastomeric layer which includes an aramid material therein and that is disposed on the first elastomeric layer, the aramid material comprising a plurality of individual strips of aramid of different sizes, wherein the aramid material distributes vibration to facilitate vibration dampening, the second elastomeric layer being substantially free of voids therein; and
   a third elastomeric layer that is disposed on the second elastomeric layer, the third elastomeric layer being substantially free of voids.

The seventh material comprises: a first layer adapted to absorb vibration and being formed by an elastomer that is substantially free of voids therein;
   a second layer which includes an aramid material therein and that is disposed on the first layer, the aramid material comprising a plurality of individual strips of aramid of generally equal sizes, wherein the aramid material distributes vibration to facilitate vibration dampening, the second layer being substantially free of voids therein, the plurality of individual aramid strips being generally parallel to each other; and
   a third layer formed by an elastomer that is substantially free of voids.

The eighth material comprises: a first elastomeric layer of vibration absorbing material which is substantially free of voids therein;
   a second layer including fiberglass material and that is disposed on the first elastomeric layer, wherein the fiberglass material distributes vibration to facilitate vibration dampening, wherein the fiberglass material forms a substantially imperforate sheet; and
   a third elastomeric layer disposed on the second elastomeric layer.

The ninth material comprises: a first elastomeric layer of vibration absorbing material which is substantially non-porous;

a second layer including a fiberglass material and that is disposed on the first elastomeric layer, wherein the fiberglass material distributes vibration to facilitate vibration dampening, wherein the fiberglass material forms a plurality of individual strips that are generally co-aligned within a common plane that extends generally throughout the second layer; and a third elastomeric layer disposed on the second elastomeric layer.

The tenth material comprises: a first elastomeric layer of vibration absorbing material which is substantially free of voids therein;

a second layer including high tensile strength fibrous material and that is disposed on the first elastomeric layer, wherein the high tensile strength fibrous material distributes vibration to facilitate vibration dampening, wherein the high tensile strength fibrous material forms a substantially imperforate sheet; and a third elastomeric layer disposed on the second elastomeric layer.

The eleventh material comprises: first and second elastomer layers; and a reinforcement layer disposed between and generally separating the first and second elastomer layers, the reinforcement layer comprising a cloth layer formed of a plurality of woven high tensile fibrous material, the plurality of woven high tensile fibrous material being connected to the first and second elastomer layers generally uniformly throughout to provide substantially complete coverage between the first and second elastomer layers, the cloth layer being generally compliant only in a direction generally perpendicular to the first major surface so as to be generally non energy storing in the direction, wherein the high tensile fibrous material generally distributes impact energy parallel to the first major surface and into the first and second elastomer layers.

The twelfth material comprises: first and second elastomer layers; and a reinforcement layer disposed between and generally separating the first and second elastomer layers, the reinforcement layer comprising a cloth layer formed of fiberglass, the fiberglass being connected to the first and second elastomer layers generally uniformly throughout to provide substantially complete coverage between the first and second elastomer layers, the cloth layer being generally compliant only in a direction generally perpendicular to the first major surface so as to be generally non energy storing in the direction, wherein the fiberglass generally distributes impact energy parallel to the first major surface and into the first and second elastomer layers.

The thirteenth material comprises: first and second elastomer layers; and a reinforcement layer disposed between and generally separating the first and second elastomer layers, the reinforcement layer comprising a cloth layer formed of a plurality of woven high tensile fibrous material, the plurality of woven high tensile fibrous material being connected to the first and second elastomer layers generally uniformly throughout to provide substantially complete coverage between the first and second elastomer layers, the cloth layer being generally compliant only in a direction generally perpendicular to the first major surface so as to be generally non energy storing in the direction, the cloth layer is generally interlocked in and generally held in position by the first and second elastomer layers, wherein the high tensile fibrous material generally distributes impact energy parallel to the first major surface and into the first and second elastomer layers.

The fourteenth material comprises: first and second elastomer layers; and a reinforcement layer disposed between and generally separating the first and second elastomer layers, the reinforcement layer comprising a cloth layer formed of a plurality of woven high tensile fibrous material, the plurality of woven high tensile fibrous material being connected to the first and second elastomer layers generally uniformly throughout to provide substantially complete coverage between the first and second elastomer layers, the cloth layer being generally compliant only in a second direction so as to be generally non energy storing in the second direction, wherein the high tensile fibrous material generally distributes impact energy parallel to the first direction and into the first and second elastomer layers.

The fifteenth material comprises: an elastomer layer having a first plurality of fibers therein; and a support structure penetrated by and embedded on and/or within the elastomer layer, the support structure being semi-rigid and supporting the elastomer layer.

The sixteenth material comprises: an elastomer layer; and a support structure penetrated by and embedded on and/or within the elastomer layer, the support structure being formed of a second elastomer having a higher durometer than the elastomer layer such that the support structure is semi-rigid and supporting the elastomer layer.

The seventeenth material comprises: a first elastomer layer; and a support structure penetrated by and embedded on and/or within the elastomer layer, the support structure being semi-rigid or rigid and supporting the elastomer layer, the support structure having a first plurality of particles therein.

The eighteenth material comprises: a first elastomer layer; and a support structure formed by a second elastomer layer, the support structure being located and configured to support the first elastomer layer.

The nineteenth material comprises: a first elastomer layer; and a support structure located and configured to support the elastomer layer, the support structure having a first plurality of gel particles therein.

The twentieth material comprises: a tape body being stretchable along the longitudinal axis from a first position to a second position, in which the tape body is elongated by a predetermined amount relative to the first position, the tape body comprising:

a first elastomer layer defining a tape length, as measured along the longitudinal axis, of the tape body;

a support structure disposed within the elastomer layer generally along the longitudinal axis in an at least partially non linear fashion while the tape body is in the first position so that a length of the support structure, as measured along a surface thereof, is greater than the tape length of the first elastomer layer; and wherein when the tape body is stretched into the second position, the support structure is at least partially straightened so that the support structure is more linear, relative to when the tape body is in the first position, the straightening of the support structure causing energy to be dissipated and generally preventing further elongation of the elastomer layer along the longitudinal axis past the second position, the support structure comprising a plurality of fibers.

The twenty-first material comprises: a tape body being stretchable along the longitudinal axis from a first position to a second position, in which the tape body is elongated by a predetermined amount relative to the first position, the tape body comprising:

a first elastomer layer defining a tape length, as measured along the longitudinal axis, of the tape body;

a support structure disposed at least partially within the elastomer layer generally along the longitudinal axis in an at least partially non linear fashion while the tape body is in the first position so that a length of the support structure, as measured along a surface thereof, is greater than the tape length of the first elastomer layer; and wherein when the tape body is stretched into the second position, the support structure is at least partially straightened so that the support structure is more linear, relative to when the tape body is in the first position, the straightening of the support structure causing energy to be dissipated and generally preventing further elongation of the elastomer layer along the longitudinal axis past the second position.

The twenty-second material comprises first and second aramid material layers, wherein the aramid materials support and contain the elastomer layer and distribute vibration to facilitate vibration dampening; and an elastomeric layer configured to absorb vibration, located substantially between the first and second aramid material layers.

The twenty-third material comprises an aramid material layer, wherein the aramid materials support and contain an elastomer layer and distribute vibration to facilitate vibration dampening, and wherein the aramid material layer is shaped as an open cylinder; and an elastomeric layer located within the open cylinder, to form a generally cylindrical shape, although other shapes could also be used.

The twenty-fourth material comprises a foam material layer; an aramid material layer that supports and contains an elastomeric layer and distributes vibration to facilitate vibration dampening; and the elastomeric material layer configured to absorb vibration.

The twenty-fifth material comprises an aramid material layer, wherein the aramid material supports and contains an elastomeric layer and distributes vibration to facilitate vibration dampening; and the elastomeric layer located adjacent to the aramid material layer.

Each of these materials could be used alone of in various combinations to reduce vibrations in the goods described herein.

BRIEF DESCRIPTION OF THE DRAWINGS

The foregoing summary, as well as the following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentality shown. In the drawings:

FIG. 3 is an elevational view of a baseball bat having a cover in the form of a sleeve on the handle area in accordance with this invention;

FIG. 4 is an enlarged fragmental cross-sectional view of the bat and sleeve shown in FIG. 3;

FIG. 5 is a schematic diagram showing the results in the application of shock forces on a cover in accordance with this invention;

FIG. 6 is a view similar to FIG. 4 showing an alternative sleeve mounted on a different implement;

FIG. 7 is a view similar to FIGS. 4 and 6 showing still yet another form of sleeve in accordance with this invention; FIG. 8 is a cross-sectional longitudinal view showing an alternative cover in accordance with this invention mounted on a further type of implement;

FIG. 8 is a cross-sectional longitudinal view showing an alternative cover in accordance with this invention mounted on a further type of implement;

FIG. 9 is a cross-sectional end view of yet another cover in accordance with this invention;

FIG. 10 is an elevational view of a hammer incorporating an abrasive dampening handle in accordance with this invention; FIG. 8 is an elevational view showing a portion of a handlebar incorporating a vibration dampening cover in accordance with this invention;

FIG. 19 is a perspective view of a shoe having a panel formed from the material of the present invention; while the panel is shown proximate to the heel of the shoe, the panel's size and placement can vary without departing from the scope of the present invention; for example, the panel can be positioned along a sidewall of the shoe, in the sole or mid-sole of the shoe, on the toe of the shoe, in the tongue of the shoe, or the panel can form the entire upper portion of the shoe, or the like;

FIG. 35 is a perspective view of a glove suitable for use with at least one of a baseball and a softball; the glove incorporates the material of the present invention;

FIG. 36 is a perspective view of a weightlifting glove that incorporates the material of the present invention;

FIG. 37 is a front elevation view of a jersey incorporating the material of the present invention;

FIG. 38 is an elevational view of athletic shorts incorporating the material of the present invention;

FIG. 39 is a elevational view of a golf glove incorporating the material of the present invention;

FIG. 40 is a elevational view of a rope handling glove or a rescue services glove incorporating the material of the present invention;

FIG. 47 is a cross-sectional view of the material of FIG. 46 separate from any implement, padding, equipment or the like;

FIG. 53 is a cross-sectional view of the material of FIG. 52 separate from any implement, padding, equipment or the like;

FIG. 56 is a cross-sectional view of the material of FIG. 54 stretched along the longitudinal axis into a second position, in which the material body is elongated by a predetermined amount relative to the first position; the straightening of the support structure causes energy to be dissipated and preferably generally prevents further elongation of the material along the longitudinal axis past the second position;

FIG. 57 is a cross-sectional view of another embodiment of the material of the present invention illustrating a more linear support structure within the material while the material is in the first position; the more linear arrangement of the support structure in the material, relative to that shown in FIG. 54, reduces the amount of elongation that is possible before the material stops stretching and effectively forms a brake on further movement;

FIG. 58 is a cross-sectional view of the material of FIG. 57 stretched along the longitudinal axis into the second position, in which the material is elongated along the longitudinal axis by a predetermined amount; because the support structure was more linear while the material was in the first position, relative to the material shown in FIG. 56, it is preferred that the amount of elongation of the material when the material is in the second position is reduced relative to the material shown in FIGS. 54 and 56;

FIG. 64 also illustrates that a breakable layer (i.e., a paper layer) or a self fusing adhesive layer can be located on one surface of the material; when a self fusing layer is located on one surface of the material, the material can be wrapped so as to allow multiple adjacent wrappings of the material to fuse together to form an integral piece; if desired, the integral piece may be waterproof for use with swimming or the like;

DETAILED DESCRIPTION OF THE PREFERRED EMBODIMENTS

Certain terminology is used in the following description for convenience only and is not limiting. The term "implement," as used in the specification and in the claims, means "any one of a baseball bat, racket, hockey stick, softball bat, sporting equipment, firearm, or the like." The above terminology includes the words above specifically mentioned, derivatives thereof, and words of similar import. Additionally, the words "a" and "one" are defined as including one or more of the referenced item unless specifically stated otherwise.

Figure 1:
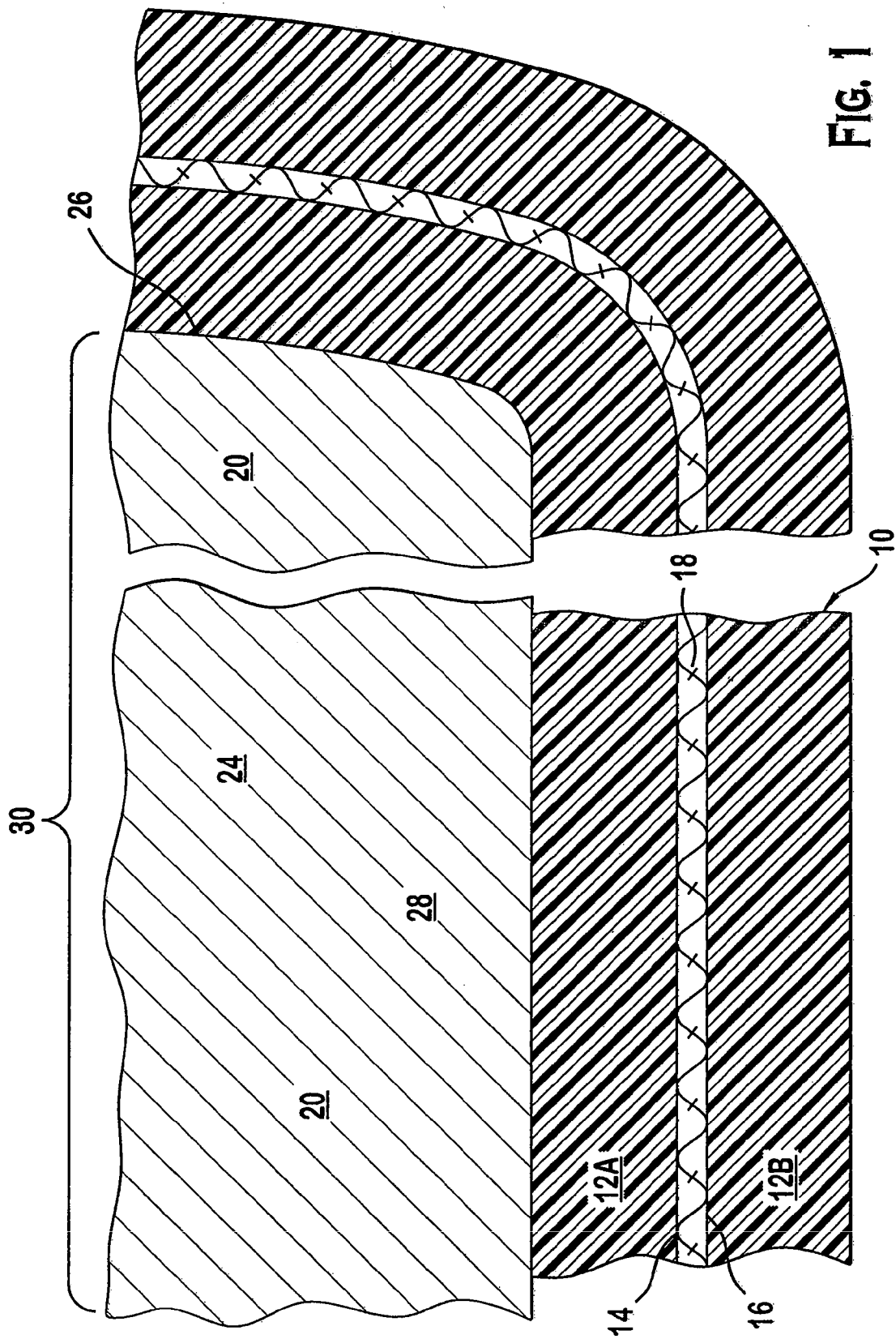
FIG. 1 is a cross-sectional view of a preferred embodiment of the material of the present invention.
Figure 2:
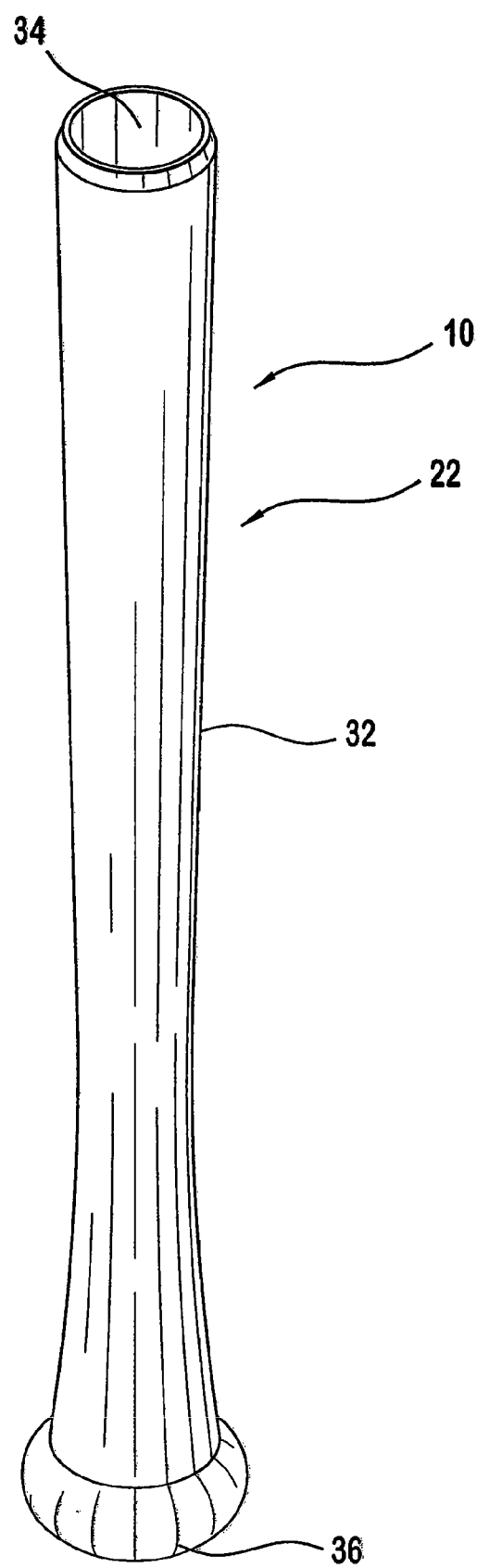
FIG. 2 is perspective view of the material of FIG. 1 configured to form a grip.
Figure 17:
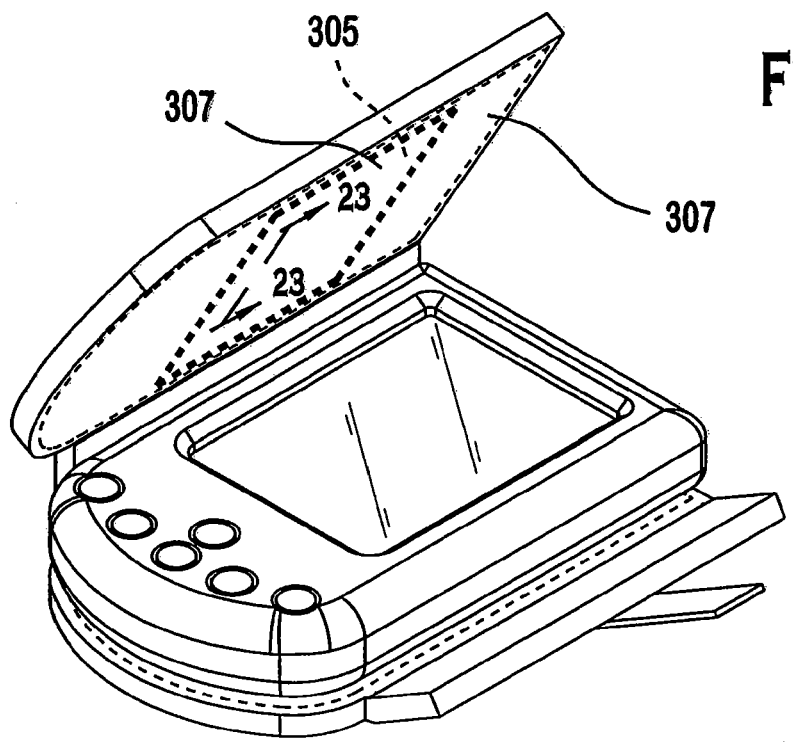
FIG. 17 is a perspective view of a portable electronic device case having a panel formed from the material of the present invention; the panel can form the entire case, or just portions of the case, without departing from the scope of the present invention; the illustrated case can be used with laptops, cell phones, GPS devices, portable music playing devices, such as MP3 players, walkie talkies, hand held video games, or the like without departing from the present invention.
Figure 19:
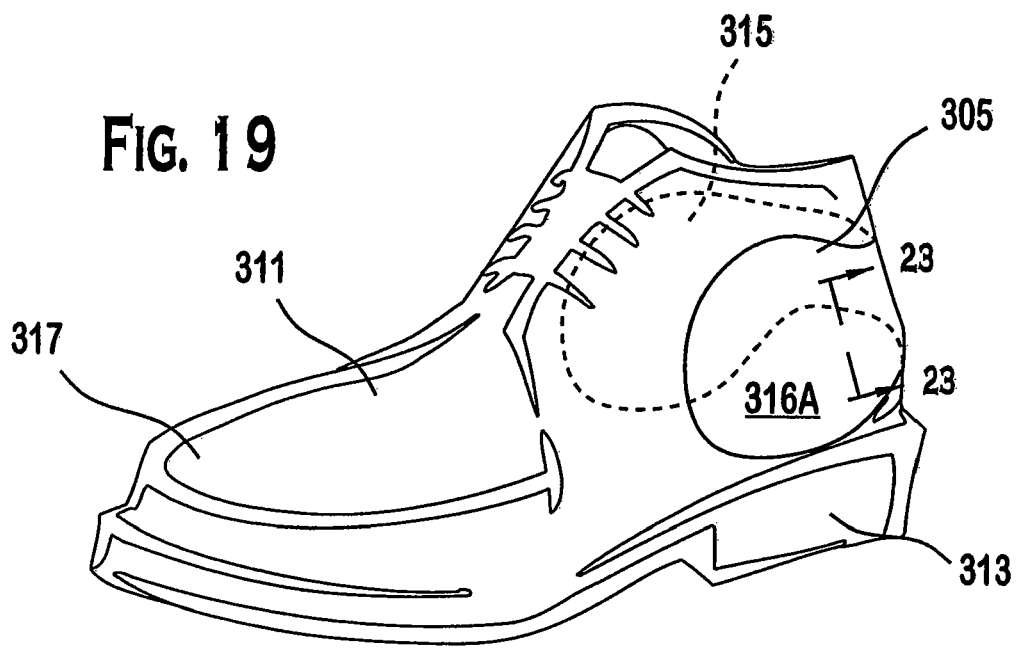
Figure 21:
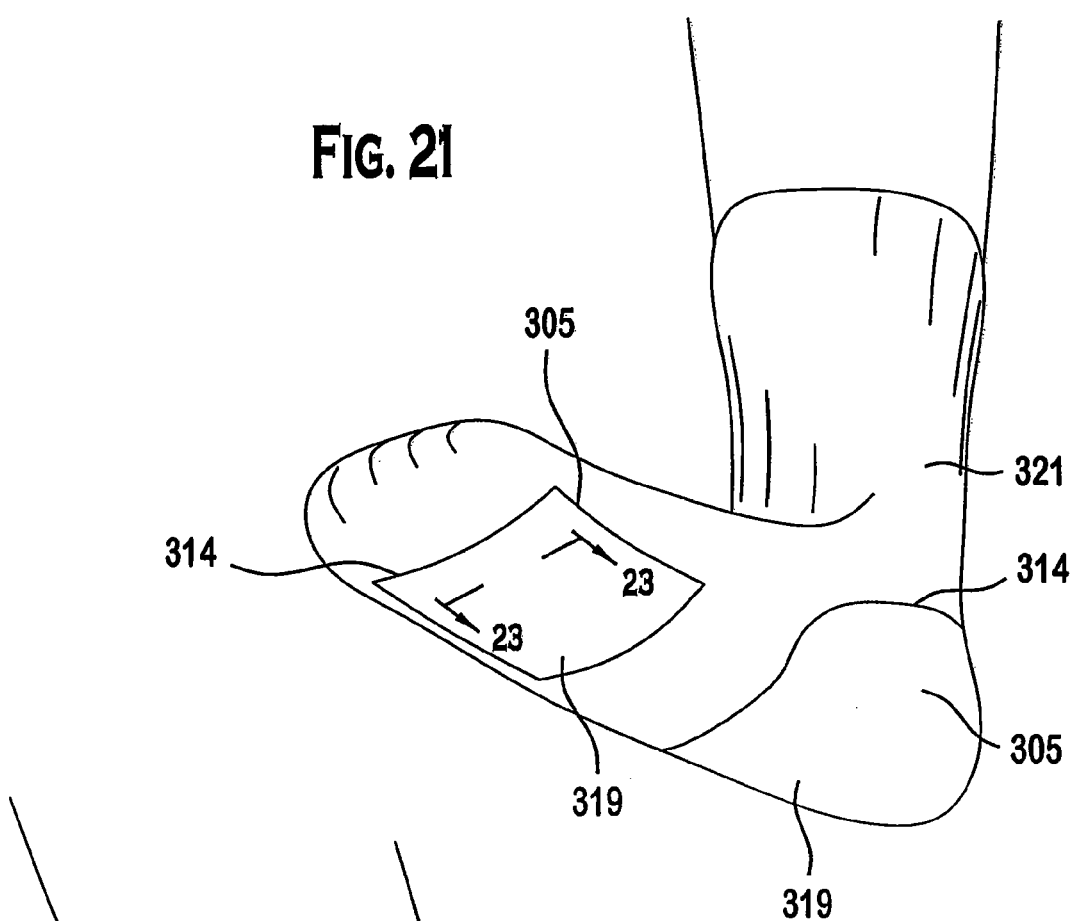
FIG. 21 is a perspective view of a sock having panels formed by the material of the present invention; the panels can be of any size and configuration; the panels can form the sock itself or be attached to an underlying fabric, such as a cotton weave.
Figure 22:
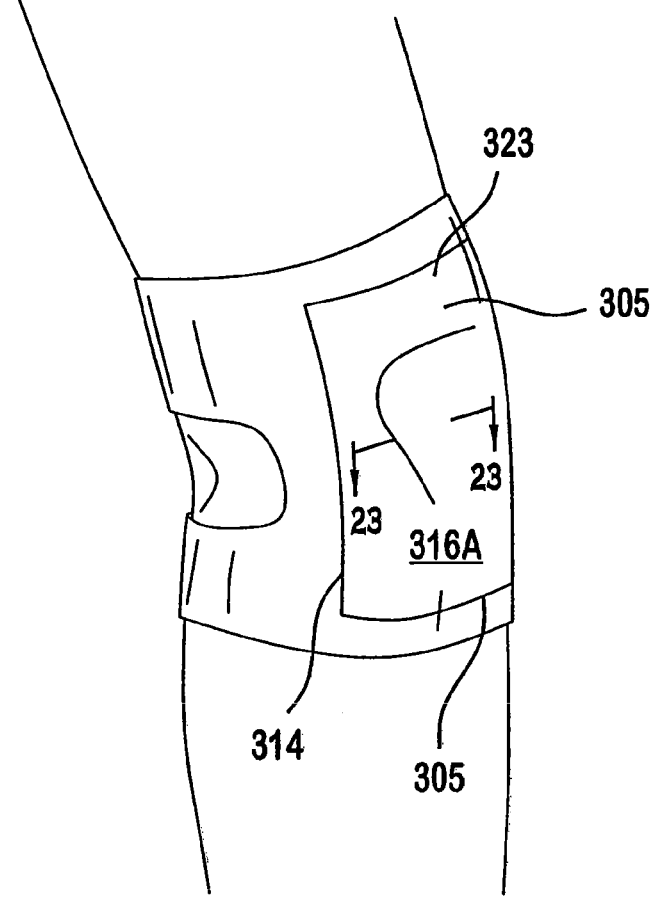
FIG. 22 is a perspective view of a kneepad having a panel formed by the material of the present invention; the panel can be of any size and configuration; the panels that are formed by the material of the present invention can be integrated in any type of kneepad or other article of clothing.
Figure 24:
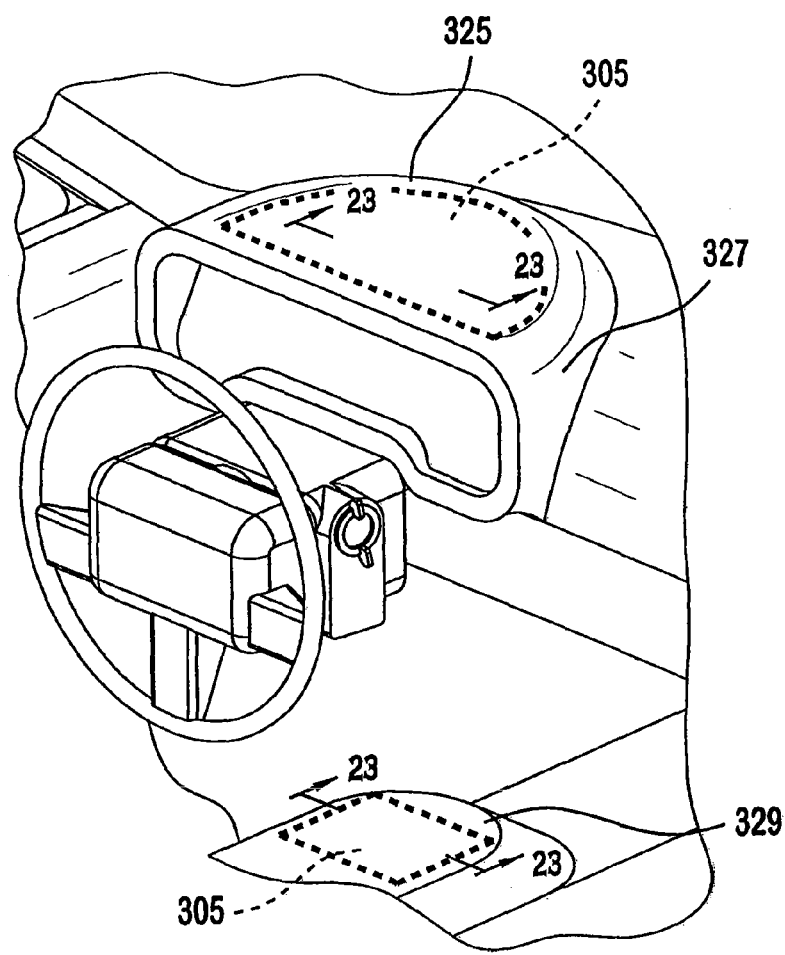
FIG. 24 is a perspective view illustrating a panel formed by the material of the present invention used to cover a dashboard, and/or a floorboard of an automobile; the panel can be used in a boat, plane, motorcycle, all terrain vehicle, train, racing vehicle, or the like and can be used in any part of a vehicle, such as a seat, roll bar, floor panel, speaker insulation, engine mounts, or the like without departing from the present invention.
Figure 25:
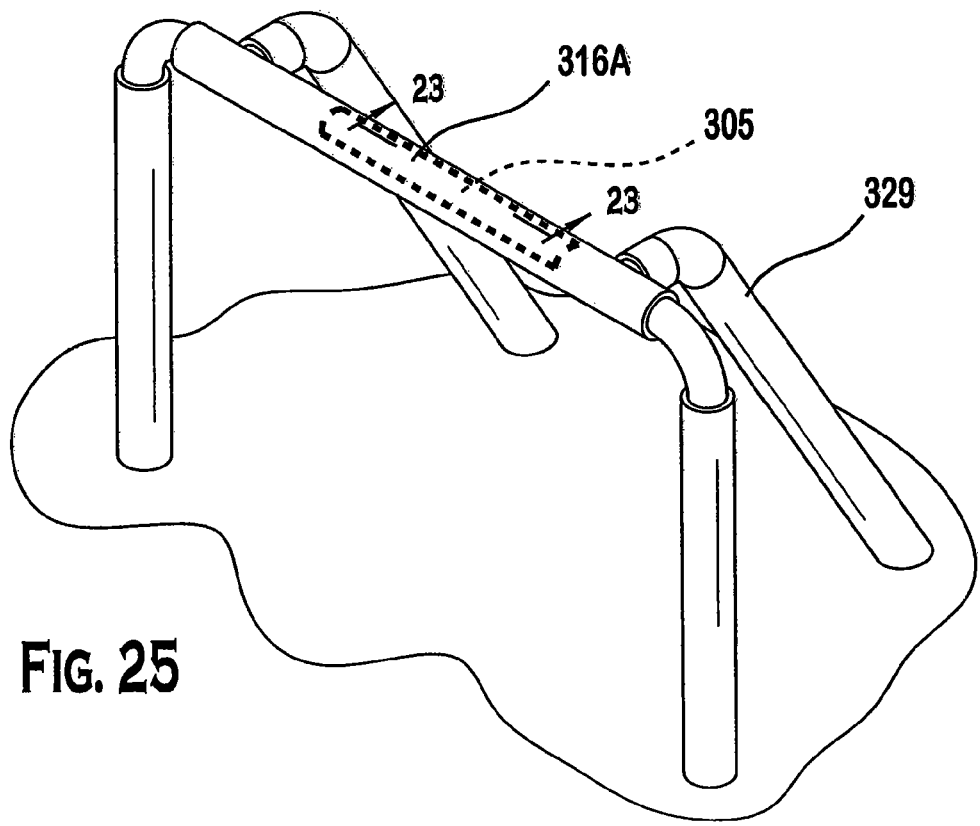
FIG. 25 is a perspective view of a roll bar for use with a vehicle that incorporates the material of the present invention as padding thereover; the roll bar padding may include a panel of the material of the present invention or may be formed entirely of the material of the present invention.
Figure 26:
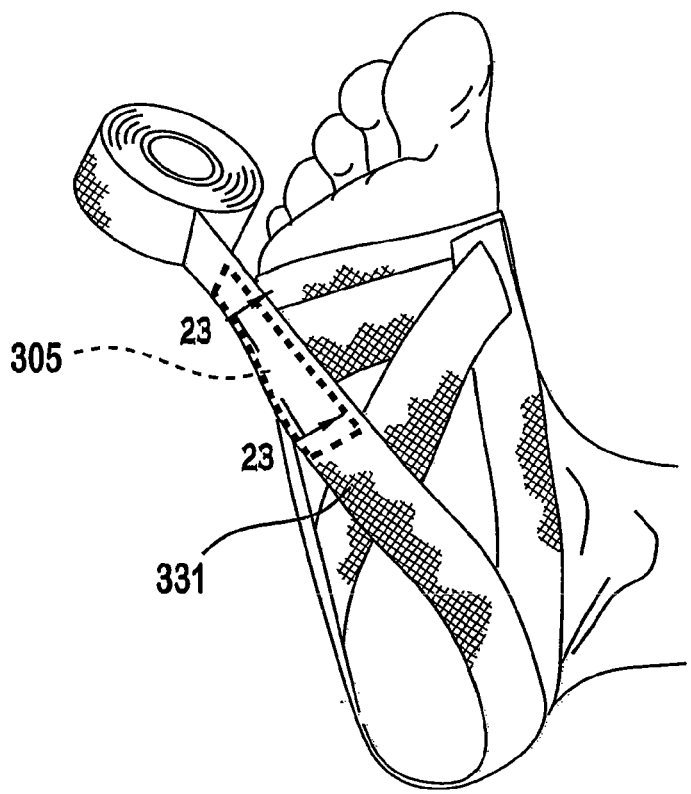
FIGS. 26-30 are perspective views of tape or other wrapping material that may include a panel of or that may be entirely made of the material of the present invention.
Figure 27:
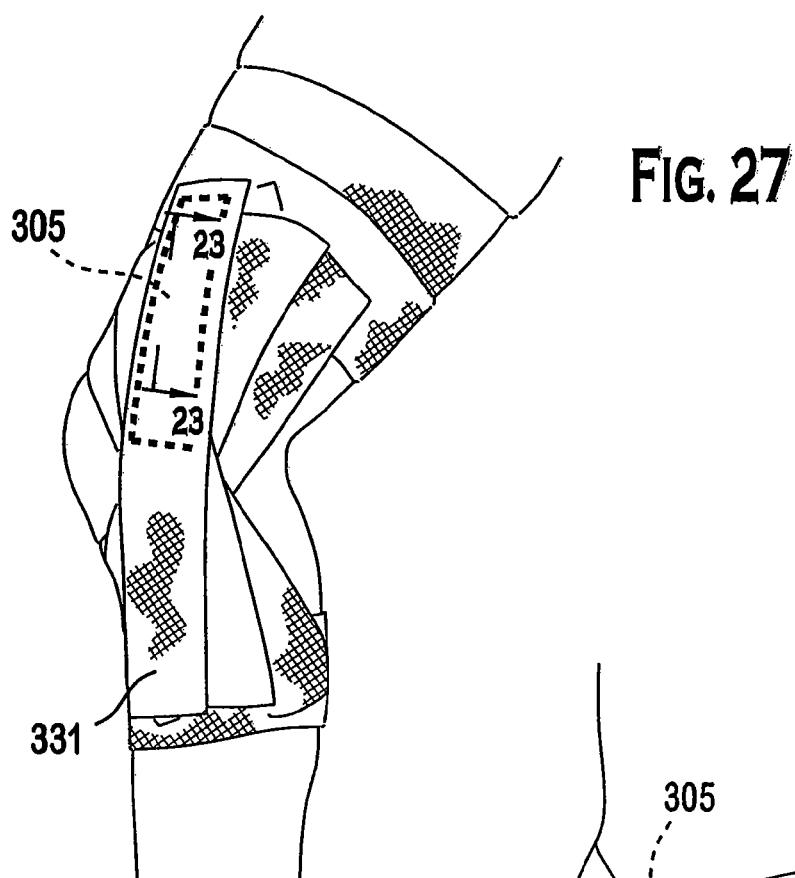
Figure 28:
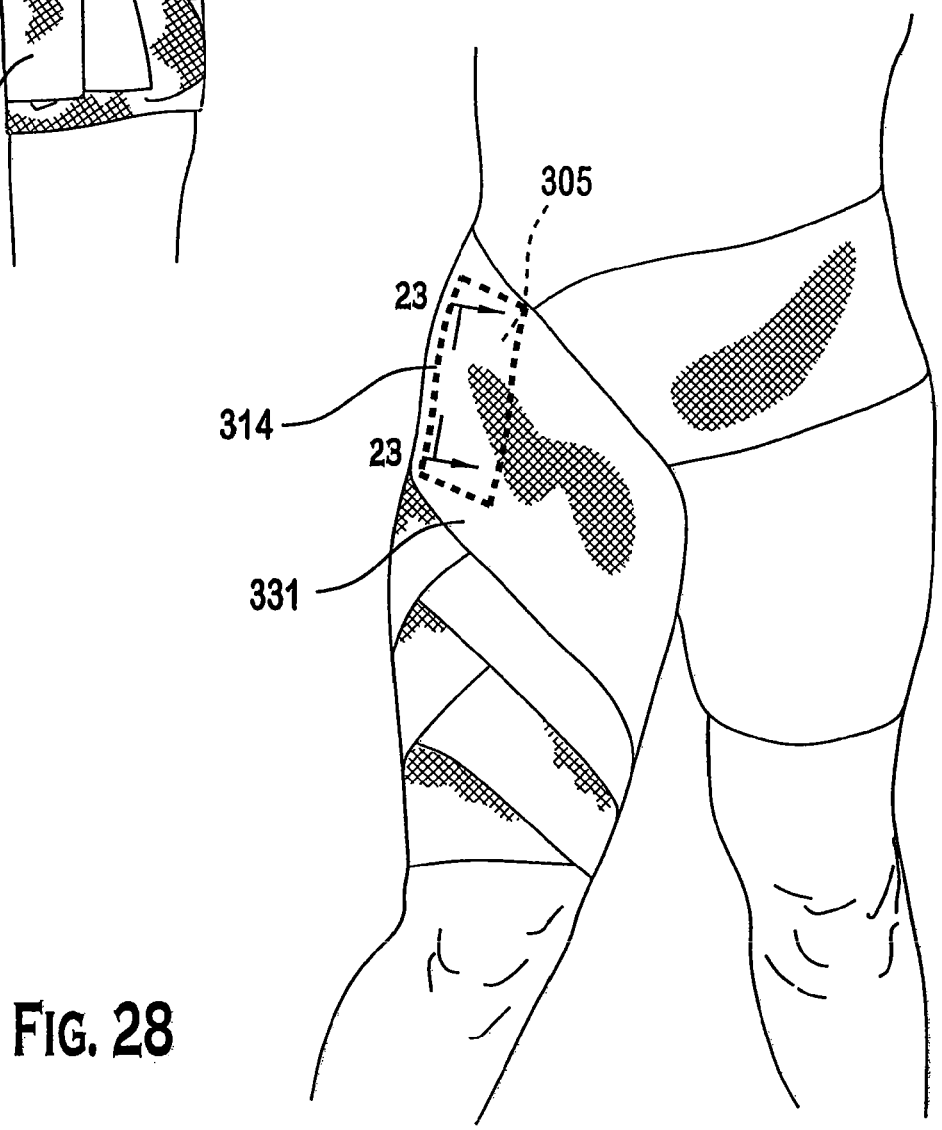
Figure 29:
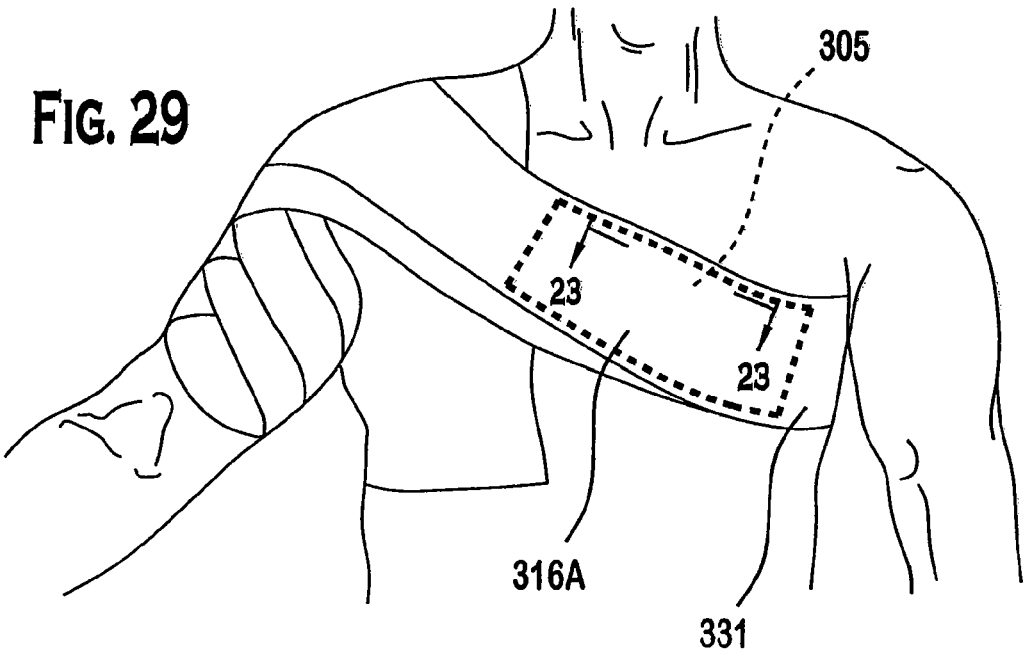
Figure 30:
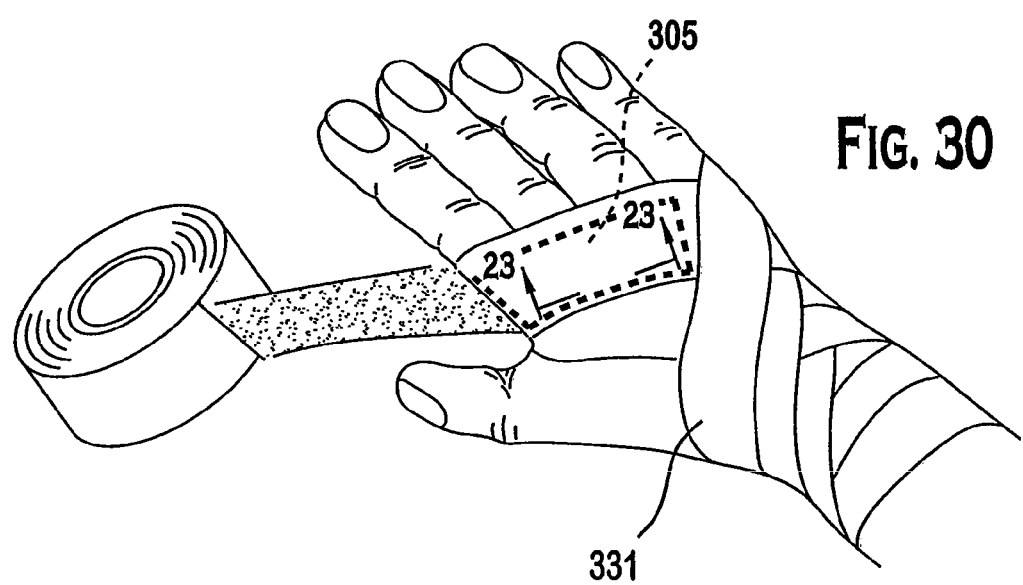

Referring to FIGS. 1 and 2, wherein like numerals indicate like elements throughout, there is shown a preferred embodiment of a material adapted to regulate vibration according to the present invention, generally designated 10. Briefly stated, the material 10 of the present invention is formed by at least a first elastomer layer 12A and a layer of high tensile strength fibrous material 14. The material 10 can be incorporated into athletic gear, grips for sports equipment, grips for tools, and protective athletic gear. The panels 305 of the material 10 can be incorporated into the various items disclosed in this application. The panel defines an outer perimeter 314 and may extend throughout the entire item that is the panel 305 may actually form the entire shoe insert, case, or other item. Alternatively, multiple panels can be separately located on an item. More specifically, the material 10 can be used: to form grips (or to form part of a grip or to form a panel 305 included in a grip) for a tennis racquet, hockey sticks, golf clubs, baseball bats or the like; to form protective athletic gear for mitts, headbands, helmets, knee pads 323 (shown in FIG. 22), umpire padding, shoulder pads, gloves, mouth guards, pads, or the like; to form seats or handle bar covers for bicycles, motorcycles, or the like; to form boots for skiing, roller blading or the like; to form clothing (such as shirts, gloves, pants, etc.) or padded liners or footwear 311 (shown in FIG. 19), such as shoe soles 313, shoe uppers 315, shoe lowers, shoe pads, ankle pads, toe pads 317, shoe inserts, and to provide padding 319 to socks 321 (shown in FIG. 21), such as sock bottoms; to form padding 307 (shown in FIG. 17) for portable electronics, such as cell phone cases, PDA cases, laptop cases, gun cases, radio cases, cassette cases, MP3 player cases, calculator cases; to form padding for speakers; to provide padding 325 (see FIG. 24) and soundproofing for automobiles 327, such as providing pole and/or roll bar padding 329 (shown in FIG. 25) in vehicles, such as automobiles, boats, trucks, all terrain vehicles, etc., providing insulation panels 329 for cars, for use in engine mounts; to form grips 309 (shown in FIG. 20) for firearms, hand guns, rifles, shotguns, or the like; to form grips for tools such as hammers, drills, screw drivers, circular saws, chisels or the like; and to form part or all of bandages and/or wraps 331 (shown in FIGS. 26-30). The material of the present invention 10 can also be used for soundproofing rooms, homes, airplanes, music studios, or the like.

The material 10 is preferably generally non elastic in a direction generally perpendicular "X" to a major material surface 316A (shown in FIG. 23) and thus, does not provide a spring like effect when experiencing impact force. It is preferred that the material 10 is generally compliant in the direction "X" which is perpendicular to the major material surface 316A, 316B so as to be generally non energy storing in the direction "X". It is preferred that the reinforcement layer generally distribute impact energy parallel to the major surfaces 316A, 316B and into the first and second elastomer layers 12A, 12B. The material 10 is preferably designed to reduce sensible vibration (and thus generally dampen and divert energy away from the object or person covered by the material).

The first elastomer layer 12A acts a shock absorber by converting mechanical vibrational energy into heat energy. The high tensile strength fibrous material layer 14 redirects vibrational energy and provides increased stiffness to the material 10 to facilitate a user's ability to control an implement 20 encased, or partially encased, by the material 10. It is preferred, but not necessary, that the high tensile strength fibrous material layer 14 be formed of aramid material.

In one embodiment, the composite material 10 may have three generally independent and separate layers including the first elastomer layer 12A and a second elastomer layer 12B. Elastomer material provides vibration damping by dissipating vibrational energy. Suitable elastomer materials include, but are not limited urethane rubbers, silicone rubbers, nitrile rubbers, butyl rubbers, acrylic rubbers, natural rubbers, styrene-butadiene rubbers, and the like. In general, any suitable elastomer material can be used to form the first and second elastomer layers without departing from the scope of the present invention. For example the elastomer layers may be thermoset elastomer layers. Alternatively, the elastomer layers 12A, 12B can be thermoplastic or any material suitable for thermoforming. For example, when manufacturing some shaped articles, such as a golf club grip, it may be more efficient to first form the material 10 as a generally flat piece or sheet of material 10 which could then be reformed or thermoformed into the desired shaped article. Additionally, the material 10 may include a shrink wrap or shrinkable layer therein and/or thereon. The shrinkable layer can be heat and/or water activated.

The material 10 can include additional layers thereover, such as a generally rigid material or the like. For example, one or more generally rigid plates of rigid material can be positioned over the material 10 to distribute impact force over an increased amount of the material. This can be useful when using the material in umpire vests, bulletproof vests, shoulder pads, shoes, or in any other application where a generally rigid outer layer is desired.

The softness of elastomer materials can be quantified using Shore A durometer ratings. Generally speaking, the lower the durometer rating, the softer the material and the more effective an elastomer layer is at absorbing and dissipating vibration because less force is channeled through the elastomer. When a soft elastomer material is squeezed, an individual's fingers are imbedded in the elastomer which increases the surface area of contact between the user's hand and creates irregularities in the outer material surface to allow a user to firmly grasp any implement 20 covered, or partially covered, by the material. However, the softer the elastomer layers 12A, 12B, the less control a user has when manipulating an implement 20 covered by the elastomer. If the elastomer layer is too soft (i.e., if the elastomer layer has too low of a Shore A durometer rating), then the implement 20 may rotate unintentionally relative to a user's hand or foot. The material 10 of the present invention is preferably designed to use first and second elastomer layers 12A, 12B having Shore A durometer ratings that provide an optimum balance between allowing a user to precisely manipulate and control the implement 20 and effectively damping vibration during use of the implement 20.

It is preferable, but not necessary, that the elastomer used with the material 10 have a Shore A durometer of between approximately ten (10) and approximately eighty (80). It is preferred that the first elastomer layer have a Shore A durometer of between approximately ten (10) and approximately twenty-five (25) and that the second elastomer layer has a Shore A durometer of between approximately twenty-five (25) and approximately forty-five (45).

The first elastomer layer 12A is preferably used to slow down impact energy and to absorb vibrational energy and to convert vibrational energy into heat energy. This preferably, but not necessarily, allows the first elastomer layer to act as a pad as well as dissipate vibration. The second elastomer layer 12B is also used to absorb vibrational energy, but also provides a compliant and comfortable grip for a user to grasp (or provides a surface for a portion of a user's body, such as the under sole of a user's foot when the material 10 is formed as a shoe insert).

In one embodiment, the first elastomer layer 12A preferably has Shore A durometer of approximately fifteen (15) and the second elastomer layer has a Shore A durometer of approximately forty-two (42). If the first and second elastomer have generally the same Shore A durometer ratings, then it is preferable, but not necessary, that the first and second elastomer layers 12A, 12B have a Shore A durometer of fifteen (15), thirty-two (32), or forty-two (42).

The high tensile strength fibrous material layer 14 is preferably, but not necessarily, formed of aramid fibers. The fibers can be woven to form a cloth layer 16 that is disposed between and generally separates the first and second elastomer layers 12A, 12B. The cloth layer 16 can be formed of aramid fibers, high tensile strength fibers, fiberglass, or other types of fiber. It is preferred that the cloth layer 16 does not have suitable rigidity for use as an open gridwork having any significant energy storage capability. It is preferred that the material which forms the reinfocement layer 14 is generally bonded to the elastomer layers 12A, 12B. The cloth layer 16 preferably generally separates the first and second elastomer layers 12A, 12B causing the material 10 to have three generally distinct and separate layers 12A, 12B, 14. The high tensile strength fibrous material layer 14 blocks and redirects vibrational energy that passes through one of the elastomer layers 12A or 12B to facilitate the dissipation of vibrations. The high tensile strength fibers 18 redirect vibrational energy along the length of the fibers 18. Thus, when the plurality of high tensile strength fibers 18 are woven to form the cloth layer 16, vibrational energy emanating from the implement 20 that is not absorbed or dissipated by the first elastomer layer 12A is redistributed evenly along the material 10 by the cloth layer 16 and then further dissipated by the second elastomer layer 12B.

The cloth layer 16 is preferably generally interlocked in, generally affixed to, or generally fixed in position by the elastomer layers 12A, 12B in order for the cloth layer 16 to block and redirect vibrational energy to facilitate dissipation of vibrations.

It is preferable that the high tensile strength fibers 18 be formed of a suitable polyamide fiber of high tensile strength with a high resistance to elongation. However, those of ordinary skill in the art will appreciate from this disclosure that any aramid fiber suitable to channel vibration can be used to form the high tensile strength fibrous material layer 14 without departing from scope of the present invention. Additionally, those of ordinary skill in the art will appreciate from this disclosure that loose fibers or chopped fibers can be used to form the high tensile strength fibrous material layer 14 without departing from the scope of the present invention. The high tensile strength fibrous material may also be formed of fiberglass. The high tensile strength fibrous material preferably prevents the material 10 from substantially elongating in a direction parallel to the major material surfaces 316A, 316B during use. It is preferred that the amount of elongation is less than ten (10%) percent. It is more preferred that the amount of elongation is less than four (4%) percent. It is most preferred that the amount of elongation is less than one (1%) percent.

Those of ordinary skill in the art will appreciate from this disclosure that the material 10 can be formed of two independent layers without departing from the scope of the present invention. Accordingly, the material 10 can be formed of a first elastomer layer 12A and a high tensile strength fibrous material layer 14 (which may be woven into a cloth layer 16) that is disposed on the first elastomer 12A.

Figure 18:
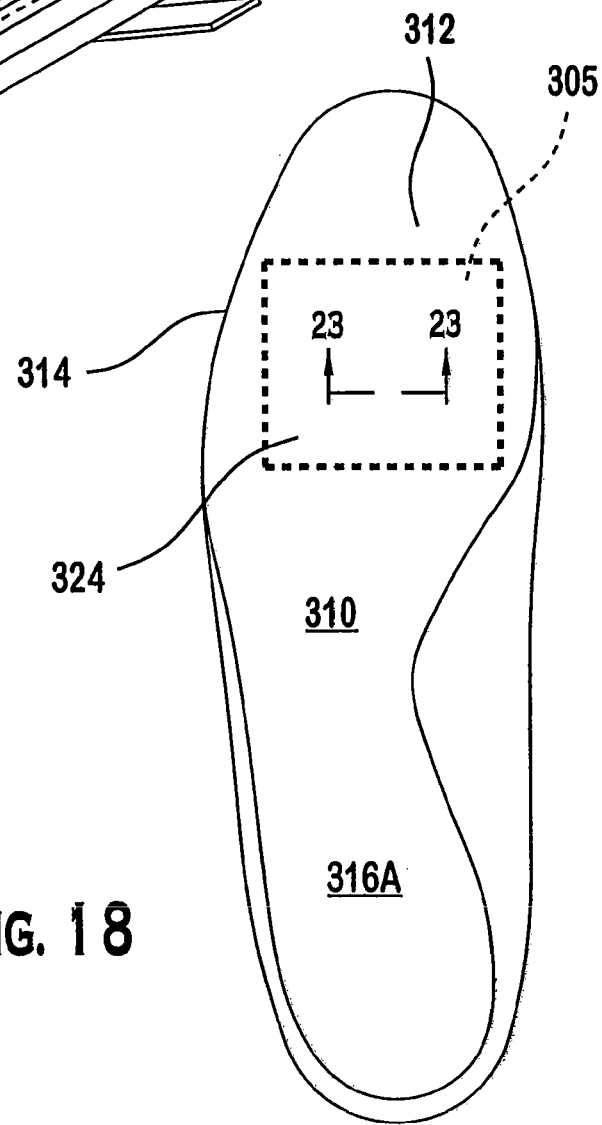
FIG. 18 is a plan view of a shoe insert formed from the material of the present invention.
Figure 23:
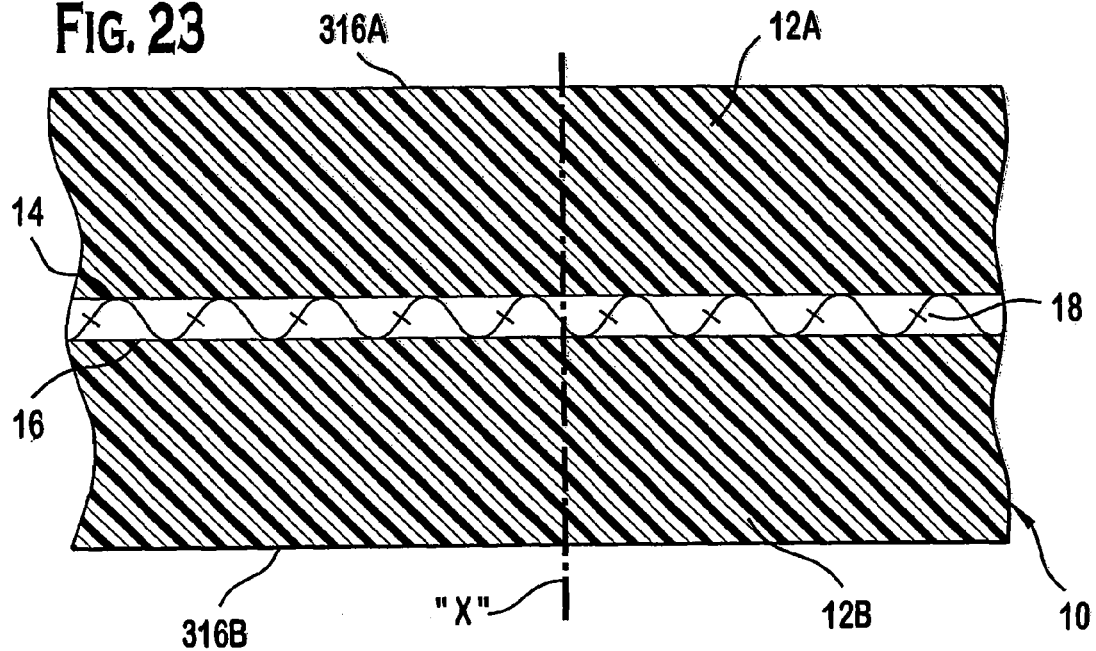
FIG. 23 is a cross-sectional view illustrating one embodiment of the material of the present invention that may be used to form a panel, covering, casing, or container as taken along the line 23-23 of FIGS. 17-22 and 24-30.

Referring to FIGS. 18 and 23, the material 10 may be configured and adapted to form an insert 310 for a shoe. When the material 10 is configured to form a shoe insert 310, the material 10 is preferably adapted to extend along an inner surface of the shoe from a location proximate to a heel of the shoe to the toe of the shoe. In addition to forming a shoe insert 310, the material 10 can be located along the sides of a shoe to protect the wearer's foot from lateral, frontal, and/or rear impact.

When the material of the present invention forms an insert 310 for a shoe, the insert 310 includes a shoe insert body 312 having a generally elongated shape with an outer perimeter 314 configured to substantially conform to a sole of the shoe so that the shoe insert body 312 extends along an inner surface of the shoe from a location proximate to a heel of the shoe to a toe of the shoe. The shoe insert body 312 is preferably generally planar and formed by a reinforced elastomer material 10 that regulates and dissipates vibration. The shoe insert body 312 has first and second major surfaces 316A, 316B.

The reinforced elastomer material 10 preferably includes first and second elastomer layers 12A, 12B. In one embodiment it is preferred that the first and second elastomer layers are generally free of voids therein and/or that the elastomer layers are formed by thermoset elastomer.

A reinforcement layer 14 is disposed between and generally separates the first and second elastomer layers 12A, 12B. The reinforcement layer 14 may include a layer formed of a plurality of high tensile strength fibrous material. Alternatively, the reinforcement layer may be formed of aramid, fiberglass, regular cloth, or the like. The reinforcement layer may be formed by woven fibers. In one embodiment, it is preferred that the reinforcement layer consist of only a single cloth layer of material.

The woven high tensile strength fibrous material is preferably connected to the first and second elastomer layers 12A, 12B generally uniformly throughout to provide substantially complete coverage between the first and second elastomer layers 12A, 12B. The cloth layer is generally compliant only in a direction "X" generally perpendicular to the first major surface 316A so as to be generally non energy storing in the direction "X". Wherein the high tensile strength fibrous material 14 generally distributes impact energy parallel to the first major surface 316A and into the first and second elastomer layers 12A, 12B. The reinforcement layer 14 preferably prevents the shoe insert 310 from substantially elongating during use. The reinforced elastomer 10 can also be used as a sole for footwear or as part of a sole or insole for footwear. The reinforced elastomer can also be used to provide padding within or along a side or upper portion of a shoe or boot.

Referring to FIGS. 4, 9, 10, and 20, the material 10 may be configured and adapted to form a grip 22 for an implement such as a bat, having a handle 24 and a proximal end 26 (i.e., the end proximal to where the bat is normally gripped). The material 10 is preferably adapted to enclose a portion of the handle 24 and to enclose the proximal end 26 of the bat or implement 20. When grip is used with a firearm the grip can be a wrap around grip or can be attached and/or molded to the firearm. As best shown in FIG. 2, it is preferable that the grip 22 be formed as a single body that completely encloses the proximal end of the implement 20. The material 10 may be also be configured and adapted to form a grip 22 for a tennis racket or similar implement 20 having a handle 24 and a proximal end 26.

Referring to FIGS. 1-3, when the material of the present invention is directed to one of the types of grips described in this application (e.g., a gun grip, tool grip, golf club grip, etc.), the grip 22 includes a grip body 318 having a generally tubular shape configured to cover a portion of the associated device. As such, the grip body 318 can have a generally circular, oval, rectangular, octagonal, polygonal cross-section or the like. The grip body 318 is formed by a reinforced elastomer material 10 that regulates and dissipates vibration. The grip body 318 defines a first direction "Y", tangential to an outer surface 320 of the grip body 318, and a second direction "Z", generally perpendicular to the outer surface 320 of the grip body 318.

The reinforced elastomer material 10 includes first and second elastomer layers 12A, 12B. A reinforcement layer 14 is disposed between and generally separates the first and second elastomer layers 12A, 12B. In some embodiments, the elastomer layer is generally free of voids and/or is a thermoset elastomer. The reinforcement layer 14 preferably includes a layer of high tensile strength fibrous material. The high tensile strength fibrous material can be woven into a cloth, chopped, or otherwise distributed. Instead of the reinforcement layer 14 being formed by high tensile strength fibrous material, the reinforcement layer 14 can be formed by a layer of fiberglass, aramid, or any other suitable material.

The high tensile strength fibrous material layer 14 is connected to the first and second elastomer layers 12A, 12B generally uniformly throughout to provide substantially complete coverage between the first and second elastomer layers. This preferably prevents sliding movement between the reinforcement layer 14 and the elastomer layers 12A, 12B. The cloth layer is preferably generally compliant only in the second direction "Z" so as to be generally non energy storing in the second direction "Z". The high tensile fibrous material generally distributes impact energy parallel to the first direction "Y" and into the first and second elastomer layers. This causes vibrational energy to be reduced and dampened rather than bounced back against the hand grasping the grip.

While the grip 22 will be described below in connection with a baseball or softball bat, those of ordinary skill in the art will appreciate that the grip 22 can be used with any of the equipment, tools, or devices mentioned above without departing from the scope of the present invention.

When the grip 22 is used with a baseball or softball bat, the grip 22 preferably covers approximately seventeen (17) inches of the handle of the bat as well as covers the knob (i.e., the proximal end 26 of the implement 20) of the bat. The configuration of the grip 22 to extend over a significant portion of the bat length contributes to increase vibrational damping. It is preferred, but not necessary, that the grip 22 be formed as a single, contiguous, one-piece member.

The baseball bat (or implement 20) has a handle 24 including a handle body 28 having a longitudinal portion 30 and a proximal end 26. The material 10 preferably encases at least some of the longitudinal portion 30 and the proximal end 26 of the handle 24. The material 10 can be produced as a composite having two generally separate and distinct layers including a first elastomer layer 12A and a high tensile strength fibrous material layer 14 (which may be a woven cloth layer 16) disposed on the elastomer layer 12A. The high tensile strength fibrous material layer 14 is preferably formed of woven fibers 18. The second elastomer layer 12B may be disposed on a major surface of the high tensile strength fibrous material layer 14 opposite from the first elastomer layer 12A.

As best shown in FIG. 2, a preferred grip 22 is adapted for use with an implement 20 having a handle and a proximal handle end. The grip 22 includes a tubular shell 32 having a distal open end 34 adapted to surround a portion of the handle and a closed proximal end 36 adapted to enclose the proximal end of the handle. The tubular shell 32 is preferably formed of the material 10 which dissipates vibration. The material 10 preferably has at least two generally separate layers including a first elastomer layer 12A and a high tensile strength fibrous material layer 14 (which fibers 18 may be woven to form a cloth layer 16) disposed on the first elastomer layer 12A.

Referring to FIGS. 17-22 and 24-30, when the material of the present invention is directed to one of the types of padding described above (e.g., speaker padding and/or insulation, shoe padding, electronic device cases, mouth guards, umpire protective gear, car interior padding, rollover bar padding, or the like, tool grip, golf club grip, etc.), the padding or item may include a panel 305 formed by a panel body 324 preferably having a generally planar shape. The panel body is preferably configured for placement in a particular location or for covering a portion of an associated device or object. It is preferable that the panel body is flexible so that shaped objects can be wrapped therein. As such, the panel body 324 may be bent around a generally circular, oval, rectangular, octagonal, or polygonal shaped object.

Figure 20:
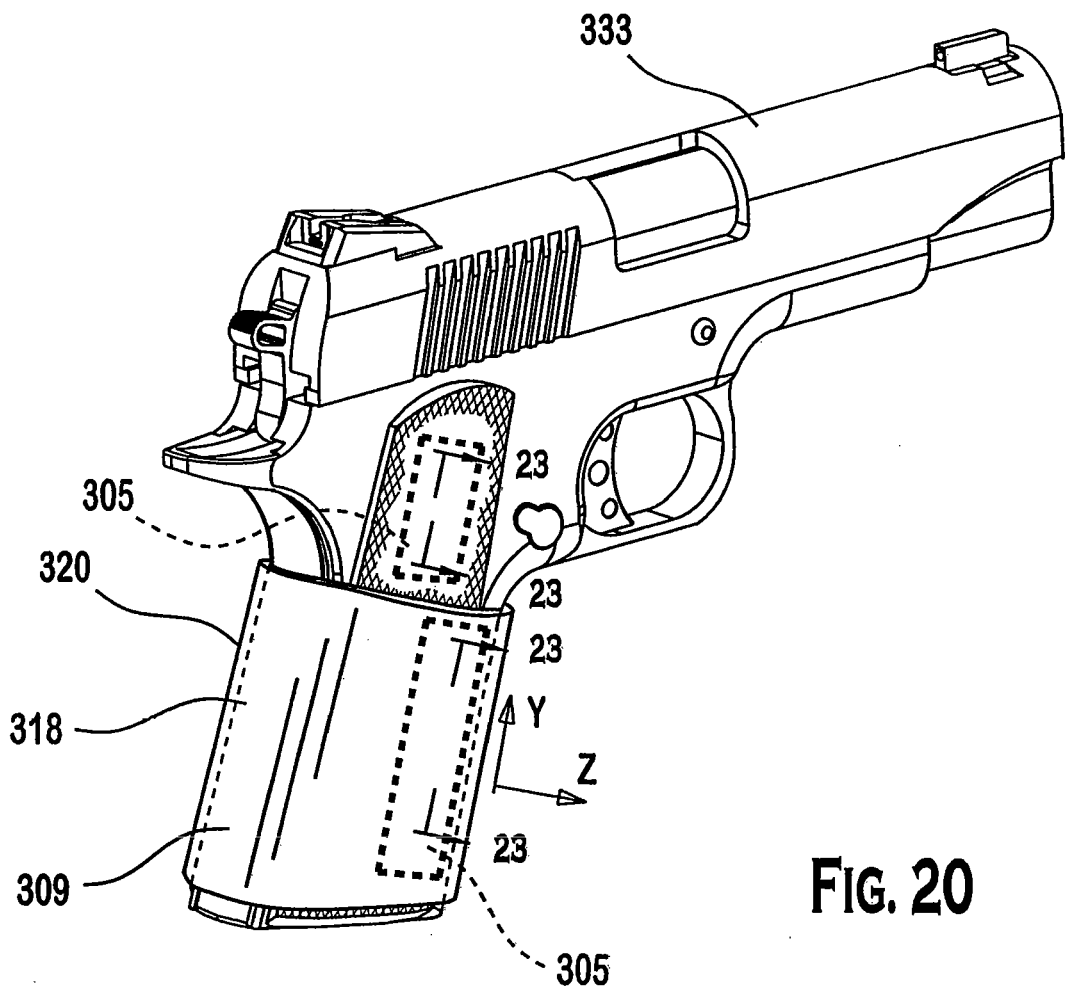
FIG. 20 is a perspective view of a firearm with a grip having at least a panel formed by the material of the present invention; the grip can be entirely formed by the material of the present invention; while the grip is shown on a handgun, those of ordinary skill in the art will appreciate that the grip can be used on any rifle, shotgun, paint ball gun, or projectile launching device without departing from the present invention; the firearm grip can be a separate wrap around grip or can be a grip attached and/or molded to the firearm.

The panel body 324 is formed by a reinforced elastomer material that regulates and dissipates vibration. As shown in FIGS. 4 and 20, the panel body 324 defines a first direction "Y", tangential, or parallel, to an outer surface of the padding body 324, and a second direction "Z", generally perpendicular to the outer surface of the panel body. The reinforced elastomer material includes first and second elastomer layers 12A, 12B. A reinforcement layer 14 is disposed between and generally separates the first and second elastomer layers 12A, 12B. In one embodiment the elastomer layers 12A, 12B are preferably free of voids and/or formed by a thermoset elastomer. The reinforcement layer 14 preferably includes a layer of high tensile strength fibrous material. The high tensile strength fibrous material can be woven into a cloth, chopped, or otherwise distributed. Instead of the reinforcement layer 14 being formed by high tensile strength fibrous material, the reinforcement layer 14 can be formed by a layer of fiberglass, aramid, or any other suitable material. The high tensile strength fibrous material layer 14 is connected to the first and second elastomer layers 12A, 12B generally uniformly throughout to provide substantially complete coverage between the first and second elastomer layers 12A, 12B. The reinforcement layer 14 is preferably generally compliant only in the second direction so as to be generally non energy storing in the second direction "Z". The reinforcement layer 14 generally distributes impact energy parallel to the first direction "Y" and into the first and second elastomer layers 12A, 12B. This causes vibrational energy to be reduced and dampened rather than bounced back. It is preferable that the reinforcement layer 14 prevents the padding from elongating during impact. The panel body 324 can form part or all of a cell phone case, a laptop case, a shoe sidewall, protective umpire gear, a mouth guard, knee pads, interior panels for automobiles or the like.

Multiple methods can be used to produce the composite or vibration dissipating material 10 of the present invention. One method is to extrude the material by pulling a high tensile strength fibrous cloth layer 16 from a supply roll while placing the first and second elastomer layers 12A, 12B on both sides of the woven high tensile strength fibrous cloth 16. A second method of producing the material 10 of the present invention is to mold the first elastomer layer 12A onto the implement 20, then to weave an aramid fiber layer thereover, and then to mold the second elastomer layer 12B thereover.

Alternatively, a cloth layer 16 can be pressured fit to an elastomer layer to form the material 10. Accordingly, the cloth layer 16 can be generally embedded in or held in place by the elastomer layer. The pressured fitting of the reinforcement layer, or fabric layer, 14 to an elastomer preferably results in the reinforcement layer, or fabric layer, 14 being generally interlocked in and/or bonded in position by the elastomer. Thus, the cloth layer can be generally interlocked with the elastomer layer. It is preferable that the high tensile strength cloth generally not be able to slide laterally between the first and second elastomer layers. The cloth layer in the resulting material would be generally fixed in position. One of ordinary skill in the art would realize that the cloth layer 14 in the resulting material would be generally interlocked and/or bonded in position by the elastomer 12A, 12B. Alternatively, the material 10 can be assembled by using adhesive or welding to secure the elastomer layer(s) to the reinforced layer.

It is preferred that the woven high tensile strength fibers are connected to the first and second elastomer layers generally uniformly throughout to provide substantially complete coverage between the first and second thermoset elastomer layers. The cloth layer is generally non energy storing in a direction generally perpendicular to a major material surface. This results in the vibrational energy being generally evenly redistributed throughout the material by the cloth layer. This is due to the high tensile strength fibers transmitting/storing energy unidirectionally along the length of the fiber and generally not storing energy in a direction generally perpendicular to the length of the fiber or perpendicular to a cloth layer formed by the fibers.

In other words, the cloth layer 16 is preferably compliant generally only in a direction generally perpendicular to a major material surface so as to be generally non energy storing in the direction perpendicular to the major material surface and to generally distribute energy parallel to the major material surface and into the first and second elastomer layers. The present invention preferably generally dissipates vibration throughout the material to prevent "bounce back" (e.g., to avoid having a runner's feet absorbed too much vibration during athletics).

In some cases the high tensile fibrous material can be pulped to form an imperforate sheet that may be secured in position between the first and second elastomer layers 12A, 12B. Those of ordinary skill in the art will appreciate from this disclosure that any known method of making composite or vibration dissipating materials can be used to form the material 10.

The covering of the proximal end of an implement 20 by the grip 22 results in reduced vibration transmission and in improved counter balancing of the distal end of the implement 20 by moving the center of mass of the implement 20 closer to the hand of a user (i.e., closer to the proximal end 26). This facilitates the swinging of the implement 20 and can improve sports performance while reducing the fatigue associated with repetitive motion.

FIGS. 3-4 illustrate another embodiment of the present invention. As shown therein a cover in the form of a sleeve 210 is mounted on the handle or lower portion 218 of a baseball bat 210. Sleeve 210 is premolded so that it can be fit onto the handle portion of the bat 212 in a quick and convenient manner. This can be accomplished by having the sleeve 210 made of a stretchable or resilient material so that its upper end 214 would be pulled open and could be stretched to fit over the knob 217 of the bat 212. Alternatively, or in addition, sleeve 210 may be provided with a longitudinal slit 16 to permit the sleeve to be pulled at least partially open and thereby facilitate snapping the sleeve 210 over the handle 218 of the bat 212. The sleeve would remain mounted in place due to the tacky nature of the sleeve material and/or by the application of a suitable adhesive on the inner surface of the sleeve and/or on the outer surface of handle 218.

A characterizing feature of sleeve 210, as illustrated in FIGS. 3-4, is that the lower end of the sleeve includes an outwardly extending peripheral knob 2220. Knob 220 could be a separate cap snapped onto or secured in any other manner to the main portion of sleeve 210. Alternatively, knob 220 could be integral with and molded as part of the sleeve 210.

In a broad practice of this invention, sleeve 210 can be a single layer. The material would have the appropriate hardness and vibration dampening characteristics. The outer surface of the material would be tacky having high friction characteristics.

Alternatively, the sleeve 210 could be formed from a two layer laminate where the vibration absorbing material forms the inner layer disposed against the handle, with a separate tacky outer layer made from any suitable high friction material such as a thermoplastic material with polyurethane being one example. Thus, the two layer laminate would have an inner elastomer layer which is characterized by its vibration dampening ability, while the main characteristic of the outer elastomer layer is its tackiness to provide a suitable gripping surface that would resist the tendency for the user's hand to slide off the handle. The provision of the knob 220 also functions both as a stop member to minimize the tendency for the handle to slip from the user's hand and to cooperate in the vibration dampening affect.

FIG. 4 illustrates the preferred form of multilayer laminate which includes the inner vibration absorbing layer 222 and the outer tacky gripping layer 224 with an intermediate layer 226 made of a stiffening material which dissipates force. If desired layer 226 could be innermost and layer 224 could be the intermediate layer. A preferred stiffening material would be aramid fibers which could be incorporated in the material in any suitable manner as later described with respect to FIGS. 13-16. However, fiberglass or any high tensile strength fibrous material can be used as the stiffening material forming the layer. Additionally, in one embodiment, the stiffening layer is substantially embedded in or held in place by the elastomer layer(s).

FIG. 5 schematically shows what is believed to be the affect of the shock forces from vibration when the implement makes contact such as from the bat 212 striking a ball. FIG. 5 shows the force vectors in accordance with a three layer laminate, such as illustrated in FIG. 4, wherein elastomeric layers 222, 224 are made of a silicone material. The intermediate layer 226 is an aramid layer made of aramid fibers. The initial shock or vibration is shown by the lateral or transverse arrows 228 on each side of the sleeve laminate 210. This causes the elastomeric layers 222,224 to be compressed along the arc 230. The inclusion of the intermediate layer 226 made from a force dissipating material spreads the vibration longitudinally as shown by the arrows 232. The linear spread of the vibration causes a rebound effect which totally dampens the vibration.

Laboratory tests were carried out at a prominent university to evaluate various grips mounted on baseball bats. In the testing, baseball bats with various grips were suspended from the ceiling by a thin thread; this achieves almost a free boundary condition that is needed to determine the true characteristics of the bats. Two standard industrial accelerometers were mounted on a specially fabricated sleeve roughly in positions where the left hand and the right hand would grip the bat. A known force was delivered to the bat with a standard calibrated impact hammer at three positions, one corresponding to the sweet spot, the other two simulating "miss hits" located on the mid-point and shaft of the bat. The time history of the force as well as the accelerations were routed through a signal conditioning device and were connected to a data acquisition device. This was connected to a computer which was used to log the data.

Two series of tests were conducted. In the first test, a control bat (with a standard rubber grip, WORTH Bat—model #C405) was compared to identical bats with several "Sting-Free" grips representing practices of the invention. These "Sting-Free" grips were comprised of two layers of pure silicone with various types of high tensile fibrous material inserted between the two layers of silicone. The types of KEVLAR, a type of aramid fiber that has high tensile strength, used in this test were referenced as follows: "005", "645", "120", "909". Also, a bat with just a thick layer of silicone but no KEVLAR was tested. With the exception of the thick silicone (which was deemed impractical because of the excessive thickness), the "645" bat showed the best reduction in vibration magnitudes.

The second series of tests were conducted using EASTON Bats (model #BK8) with the "645" KEVLAR in different combinations with silicone layers: The first bat tested was comprised of one bottom layer of silicone with a middle layer of the "645" KEVLAR and one top layer of silicone referred to as "111". The second bat test was comprised of two bottom layers of silicone with a middle layer of KEVLAR and one top layer of silicone referred to as "211". The third bat tested was comprised of one bottom layer of silicone with a middle layer of KEVLAR and two top layers of silicone referred to as "112". The "645" bat with the "111" configuration showed the best reduction in vibration magnitudes.

In order to quantify the effect of this vibration reduction, two criteria were defined: (I) the time it takes for the vibration to dissipate to an imperceptible value; and, (2) the magnitude of vibration in the range of frequencies at which the human hand is most sensitive.

The sting-free grips reduced the vibration in the baseball bats by both quantitative measures. In particular, the "645" KEVLAR in a "111" configuration was the best in vibration reduction. In the case of a baseball bat, the "645" reduced the bat's vibration in about ⅕ the time it took the control rubber grip to do so. The reduction in peak magnitude of vibration ranged from 60% to 80%, depending on the impact location and magnitude.

It was concluded that the "645" KEVLAR grip in a "111" combination reduces the magnitude of sensible vibration by 80% that is induced in a baseball bat when a player hits a ball with it. This was found to be true for a variety of impacts at different locations along the length of the bat. Hence, a person using the "Sting-Free" grips of the invention would clearly experience a considerable reduction in the sting effect (pain) when using the "Sting-free" grip than one would with a standard grip.

In view of the above tests a particularly preferred practice of the invention involves a multilayer laminate having an aramid such as KEVLAR, sandwiched between layers of pure silicone. The above indicated tests show dramatic results with this embodiment of the invention. As also indicated above, however, the laminate could comprise other combinations of layers such as a plurality of bottom layers of silicone or a plurality of top layers of silicone. other variations include a repetitive laminate assembly wherein a vibration dampening layer is innermost with a force dissipating layer against the lower vibration dampening layer and then with a second vibration dampening layer over the force dissipating layer followed by a second force dissipating layer, etc. with the final laminate layer being a gripping layer which could also be made of vibration dampening material. Among the considerations in determining which laminate should be used would be the thickness limitations and the desired vibration dampening properties.

The various layers could have different relative thicknesses. Preferably, the vibration dampening layer, such as layer 222, would be the thickest of the layers. The outermost gripping layer, however, could be of the same thickness as the vibration dampening layer, such as layer 224 shown in FIG. 4 or could be a thinner layer since the main function of the outer layer is to provide sufficient friction to assure a firm gripping action. A particularly advantageous feature of the invention where a force dissipating stiffening layer is used is that the force dissipating layer could be very thin and still achieve its intended results. Thus, the force dissipating layer would preferably be the thinnest of the layers, although it might be of generally the same thickness as the outer gripping layer. If desired the laminate could also include a plurality of vibration dampening layers (such as thin layers of gel material) and/or a plurality of stiffening force dissipating layers. Where such plural layers are used, the various layers could differ in the thickness from each other.

FIGS. 3-4 show the use of the invention where the sleeve 210 is mounted over a baseball bat 212 having a knob 217. The same general type structure could also be used where the implement does not have a knob similar to a baseball bat knob. FIG. 6, for example, illustrates a variation of the invention wherein the sleeve 210A would be mounted on the handle 218A of an implement that does not terminate in any knob. Such implement could be various types of athletic equipment, tools, etc. The sleeve 210A, however, would still have a knob 2220A which would include an outer gripping layer 224A, an intermediate force dissipating layer 226A and an inner vibration dampening layer 222A. In the embodiment shown in FIG. 6, the handle 218A extends into the knob 220A. Thus, the inner layer 222A would have an accommodating recess 34 for receiving the handle 218A. The inner layer 222A would also be of greater thickness in the knob area as illustrated.

FIG. 7 shows a variation where the sleeve 210B fits over handle 218B without the handle 218B penetrating the knob 220B. As illustrated, the outer gripping layer 224B would be of uniform thickness both in the gripping area and in the knob. Similarly, the intermediate force dissipating layer 226B would also be of uniform thickness. The inner shock absorbing layer 222B, however, would completely occupy the portion of the knob inwardly of the force dissipating layer 226B since the handle 218B terminates short of the knob 2220B.

FIG. 8 shows a variation of the invention where the gripping cover 236 does not include a knob. As shown therein, the gripping cover would be mounted over the gripping area of a handle 238 in any suitable manner and would be held in place either by a previously applied adhesive or due to the tacky nature of the innermost vibration dampening layer 240 or due to resilient characteristics of the cover 236. Additionally, the cover might be formed directly on the handle 238. FIG. 10, for example, shows a cover 236B which is applied in the form of tape.

As shown in FIG. 8 the cover 236 includes one of the laminate variations where a force dissipating layer 242 is provided over the inner vibration dampening layer 240 with a second vibration dampening layer 244 applied over force dissipating layer 242 and with a final thin gripping layer 246 as the outermost layer. As illustrated, the two vibration dampening layers 240 and 244 are the thickest layers and may be of the same or differing thickness from each other. The force dissipating layer 242 and outer gripping layer 244 are significantly thinner.

FIG. 9 shows a cover 236A mounted over a hollow handle 238A which is of non-circular cross-section. Handle 238A may, for example, have the octagonal shape of a tennis racquet.

FIG. 10 shows a further cover 236B mounted over the handle portion of tool such as hammer 248. As illustrated, the cover 236B is applied in tape form and would conform to the shape of the handle portion of hammer 248. Other forms of covers could also be applied rather than using a tape. Similarly, the tape could be used as a means for applying a cover to other types of implements.

Figure 11:
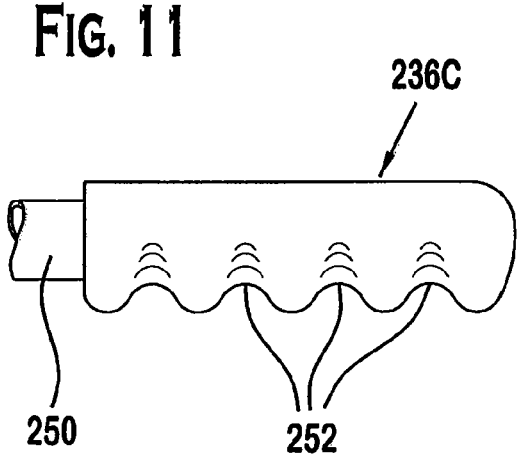
FIG. 11 is an elevational view showing a portion of a handlebar incorporating a vibration dampening cover in accordance with this invention; the handlebar grip can include an attached insert (that is also formed of the material of the present invention) that is located inside of a hollow in the handlebar to effectively cause the handlebar structure to become another layer of the material of the present invention (for example, if the handlebar is formed of a composite, then the composite material would just form another layer of the material of the present invention)

FIG. 11 illustrates a cover 236C mounted over the end of a handlebar, such as the handlebar of various types of cycles or any other device having a handlebar including steering wheels for vehicles and the like. FIG. 11 also illustrates a variation where the cover 236C has an outer contour with finger receiving recesses 252. Such recesses could also be utilized for covers of other types of implements.

Figure 12:
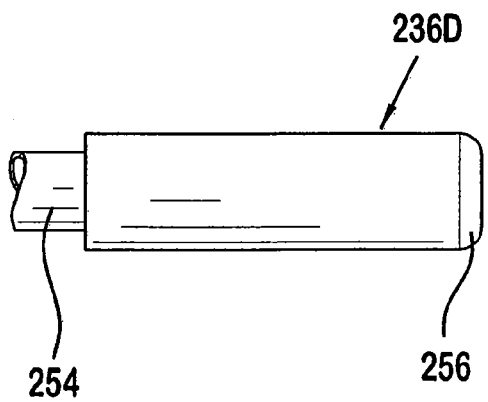
FIG. 12 is a view similar to FIG. 11 of yet another practice of this invention.

FIG. 12 illustrates a variation of the invention where the cover 236D is mounted to the handle portion of an implement 254 with the extreme end 256 of the implement being bare. This illustration is to show that the invention is intended to provide a vibration dampening gripping cover for the handle of an implement and that the cover need not extend beyond the gripping area. Thus, there could be portions of the implement on both ends of the handle without having the cover applied to those portions.

In a preferred practice of the invention, as previously discussed, a force dissipating stiffening layer is provided as an intermediate layer of a multilayer laminate where there is at least one inner layer of vibration dampening material and an outer layer of gripping material with the possibility of additional layers of vibration dampening material and force dissipating layers of various thickness. As noted the force dissipating layer could be innermost. The invention may also be practiced where the laminate includes one or more layers in addition to the gripping layer and the stiffening layer and the vibration dampening layer. Such additional layer(s) could be incorporated at any location in the laminate, depending on its intended function (e.g., an adhesive layer, a cushioning layer, etc.).

Figure 13:
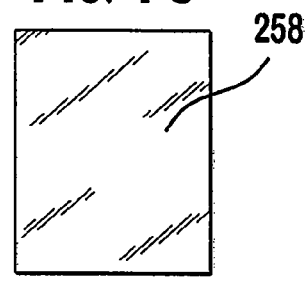
FIGS. 13-16 are plan views of various forms of the intermediate force dissipating layer which is used in certain practices of this invention.
Figure 14:
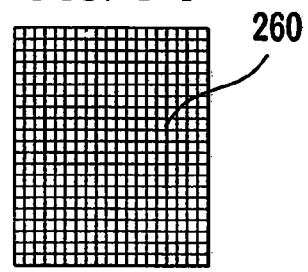
Figure 15:
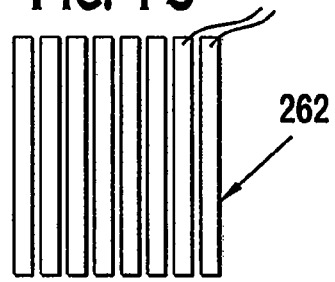
Figure 16:
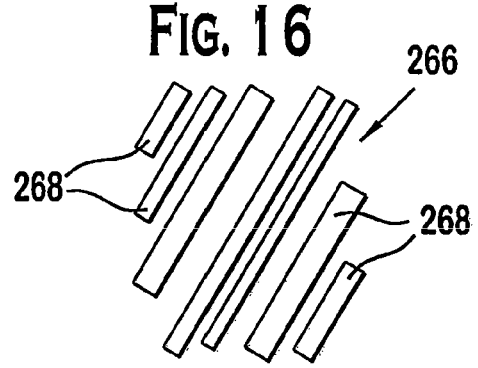

The force dissipating layer could be incorporated in the laminate in various manners. FIG. 13, for example, illustrates a force dissipating stiffening layer 258 in the form of a generally imperforate sheet. FIG. 14 illustrates a force dissipating layer 260 in the form of an open mesh sheet. This is a particularly advantageous manner of forming the force dissipating layer where it is made of KEVLAR fibers. FIG. 15 illustrates a variation where the force dissipating layer 262 is formed from a plurality of individual strips of material 264 which are parallel to each other and generally identical to each other in length and thickness as well as spacing. FIG. 16 shows a variation where the force dissipating layer 266 is made of individual strips 268 of different sizes and which could be disposed in a more random fashion regarding their orientation. Although all of the strips 268 are illustrated in FIG. 14 as being parallel, non-parallel arrangements could also be used.

The vibration dampening grip cover of this invention could be used for a wide number of implements. Examples of such implements include athletic equipment, hand tools and handlebars. For example, such athletic equipment includes bats, racquets, sticks, javelins, etc. Examples of tools include hammers, screwdrivers, shovels, rakes, brooms, wrenches, pliers, knives, handguns, air hammers, etc. Examples of handlebars include motorcycles, bicycles and various types of steering wheels.

A preferred practice of this invention is to incorporate a force dissipating layer, particularly an aramid, such as KEVLAR fiber, into a composite with at least two elastomers. One elastomer layer would function as a vibration dampening material and the other outer elastomer layer which would function as a gripping layer. The outer elastomer layer could also be a vibration dampening material. Preferably, the outer layer completely covers the composite.

There are an almost infinite number of possible uses for the composite of laminate of this invention. In accordance with the various uses the elastomer layers may have different degrees of hardness, coefficient of friction and dampening of vibration. Similarly, the thicknesses of the various layers could also vary in accordance with the intended use. Examples of ranges of hardness for the inner vibration dampening layer and the outer gripping layer (which may also be a vibration absorbing layer) are 5-70 Durometer Shore A. One of the layers may have a range of 5-20 Durometer Shore A and the other a range of 30-70 Durometer Shore A for either of these layers. The vibration dampening layer could have a hardness of less than 5, and could even be a 000 Durometer reading. The vibration dampening material could be a gel, such as a silicone gel or a gel of any other suitable material. The coefficient of friction as determined by conventional measuring techniques for the tacky and non-porous gripping layer is preferably at least 0.5 and may be in the range of 0.6-1.5. A more preferred range is 0.7-1.2 with a still more preferred range being about 0.8-1. The outer gripping layer, when also used as a vibration dampening layer, could have the same thickness as the inner layer. When used solely as a gripping layer the thickness could be generally the same as the intermediate layer, which might be about $\frac{1}{20}$ to $\frac{1}{4}$ of the thickness of the vibration dampening layer.

The grip cover of this invention could be used with various implements as discussed above. Thus, the handle portion of the implement could be of cylindrical shape with a uniform diameter and smooth outer surface such as the golf club handle 238 shown in FIG. 6. Alternatively, the handle could taper such as the bat handle shown in FIGS. 3-4. Other illustrated geometric shapes include the octagonal tennis racquet handle 238A shown in FIG. 9 or a generally oval type handle such as the hammer 248 shown in FIG. 10. The invention is not limited to any particular geometric shape. In addition, the implement could have an irregular shape such as a handle bar with finger receiving depressions as shown in FIG. 11. Where the outer surface of the implement handle is of non-smooth configuration the inner layer of the cover could press against and generally conform to the outer surface of the handle and the outermost gripping layer of the cover could include its own finger receiving depressions. Alternatively, the cover may be of uniform thickness of a shape conforming to the irregularities in the outer surface of the handle.

Figure 31:
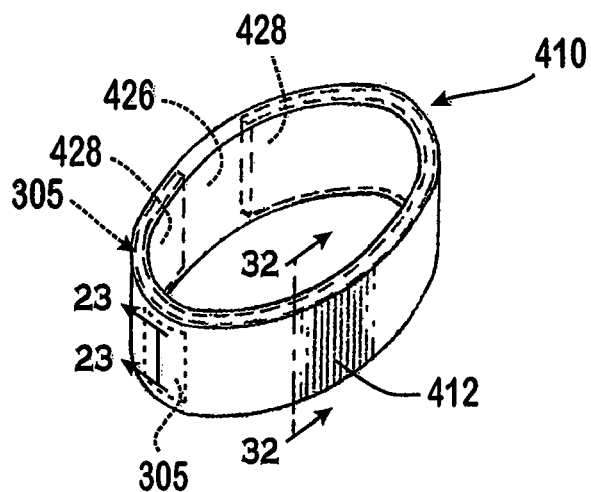
FIG. 31 is a perspective view of a headband formed, at least in part, by the material of the present invention.
Figure 32:
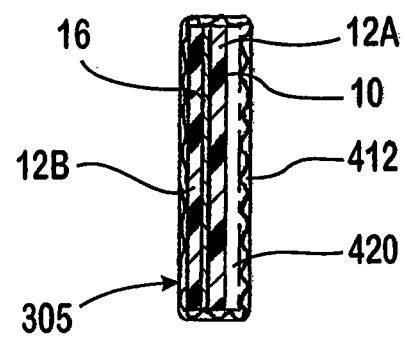
FIG. 32 is a cross-sectional view of a portion of the headband of FIG. 31 as taken along the line 32-32 in FIG. 31.

Referring to FIGS. 31 and 32, the material 10 of the present invention can be used to form part of a headband 410. The headband preferably has a peripheral outer fabric layer 412 that forms a hollow tubular shape in which the material 10 is located. Space 420 represents schematically room for one or more layers of the material 10. A particular advantage of the headband 410 is that it lends itself more readily to acceptance by users, such as children, who prefer not to wear large and cumbersome head protective gear. Although FIG. 1 shows the headband 410 to be a continuous endless flexible loop, it is to be understood that the invention could be incorporated in a headband or visor where the headband or visor does not extend completely around the head three hundred and sixty degrees. Instead, the headband or visor could be made of a stiff springy material having a pair of free ends 428 separated by a gap 426.

Figure 33:
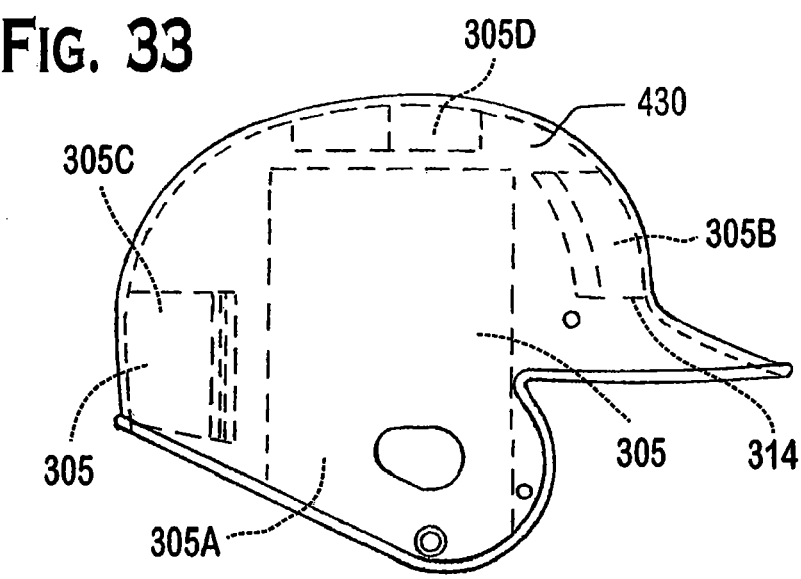
FIG. 33 is a side elevational view of a helmet including panels formed by the material of the present invention.
Figure 34:
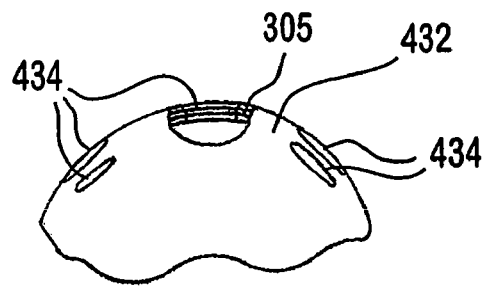
FIG. 34 is a perspective, partially broken away view of a cycling helmet incorporating the material of the present invention.

FIG. 33 shows panels 305 of material 10 incorporated into a helmet 430. The panels include temple and ear covering panels 305A; forehead covering panels 305B; neck panels 305C; and top panels 305D. FIG. 34 shows a cyclist helmet 432 with air vents 434 therein. A broken away portion of the top of the cyclist helmet shows the integration of at least one panel 305 with the helmet 432. Although two particular types of helmets are specifically discussed, those of ordinary skill in the art will appreciate from this disclosure that the material 10 can be incorporated into any type of hat (such as a hard hat or a baseball cap), helmet (such as a paintball helmet, a batting helmet, a motorcycle helmet, or an army helmet) or the like without departing from the present invention. The panel 305 can be a lining for hard shell headgear, for a shell, or for a soft cap.

FIGS. 37 and 38 illustrate a shirt 440 and pants 444 incorporating panels 305 formed of the material 10 of the present invention. A preferred cross-section of the panels 305 is shown in FIG. 23. The shirt panels 305 can vary in number and position as desired. The pants 444 preferably include multiple panels 305, including a thigh protection panel 305F; a hip protection panel 305E; and a rear protection panel 305G.

Figure 41:
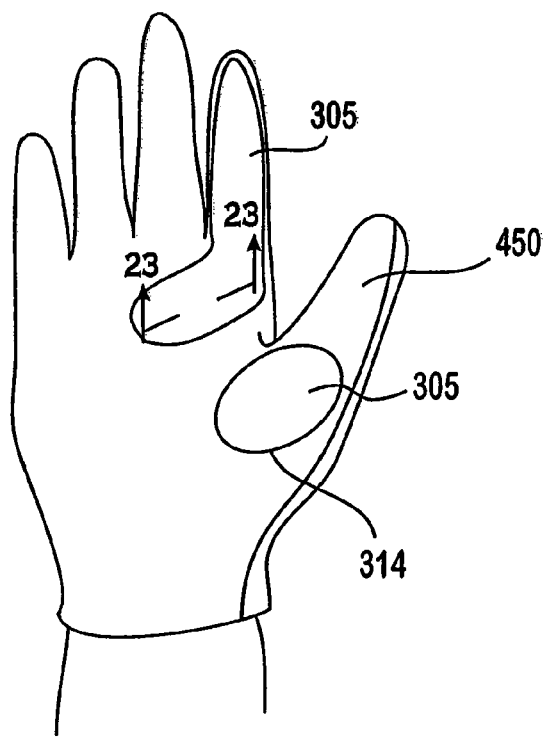
FIG. 41 is a elevational view of a batting glove incorporating the material of the present invention.
Figure 42:
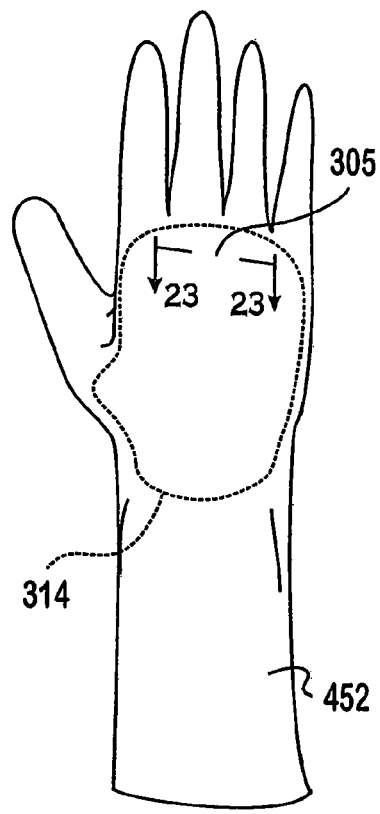
FIG. 42 is a elevational view of a lady's dress glove incorporating the material of the present invention.
Figure 43:
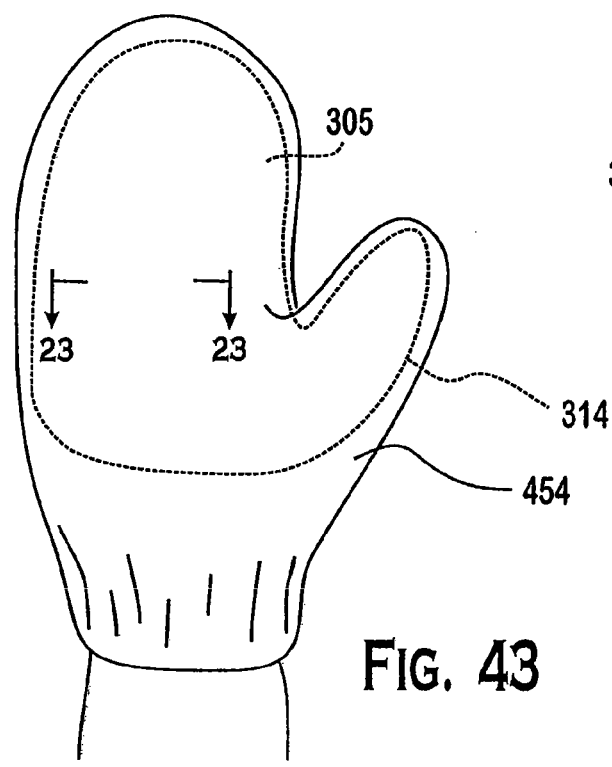
FIG. 43 is a elevational view of a ski mitten incorporating the material of the present invention.
Figure 44:
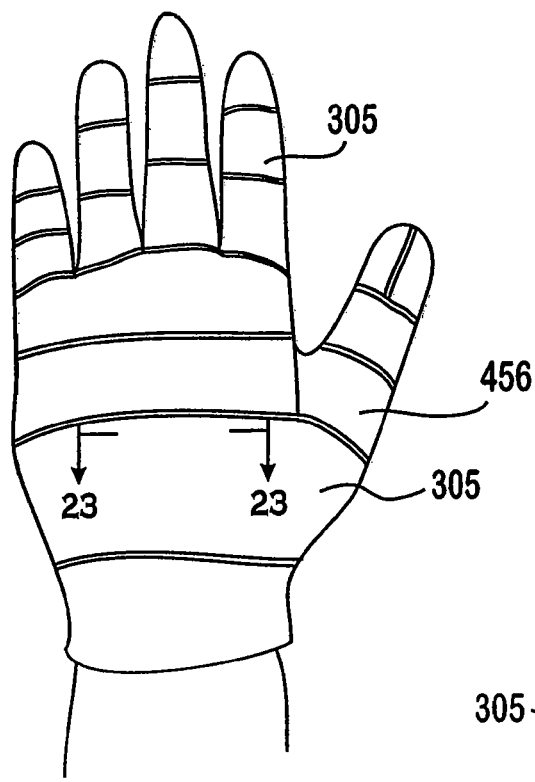
FIG. 44 is a elevational view of a lacrosse glove incorporating the material of the present invention.
Figure 45:
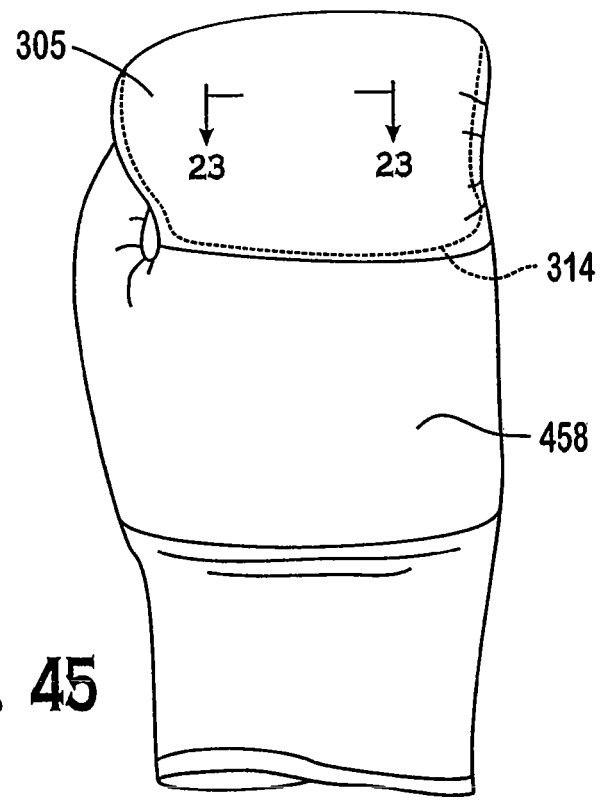
FIG. 45 is a elevational view of boxing glove incorporating the material of the present invention.

As detailed above, the material 10 of the present invention can be used to form gloves or to form panels 305 incorporated into gloves. The preferred cross-section of the glove panels 305 is also shown in FIG. 23. FIG. 35 illustrates a glove 436 suitable for both baseball and softball that uses panels 305 to provide protection to a palm area 437. FIG. 36 illustrates a weightlifting glove 438 having panels 305 of the material 10 thereon. 9 illustrates a golf glove 446 having at least one panel 305 thereon. FIG. 40 illustrates the type of glove 448 used for rope work or by rescue services personnel with panels 305 of the material 10 of the present invention. FIG. 41 shows a batting glove 450 with panels 305 thereon. The material 10 can also be used to form panels 305 for women's dress gloves 452 or ski mittens 454, as shown in FIGS. 42 and 43. Lacrosse gloves 456 and boxing gloves 458 can also be formed entirely of the material 10 of the present invention or can incorporate panels 305 of the material 10. Although specific types of gloves have been mentioned above, those of ordinary skill in the art will appreciate that the material 10 of the present invention can be incorporated into any type of gloves, athletic gloves, dress gloves, or mittens without departing from the scope of the present invention.

Figure 46:
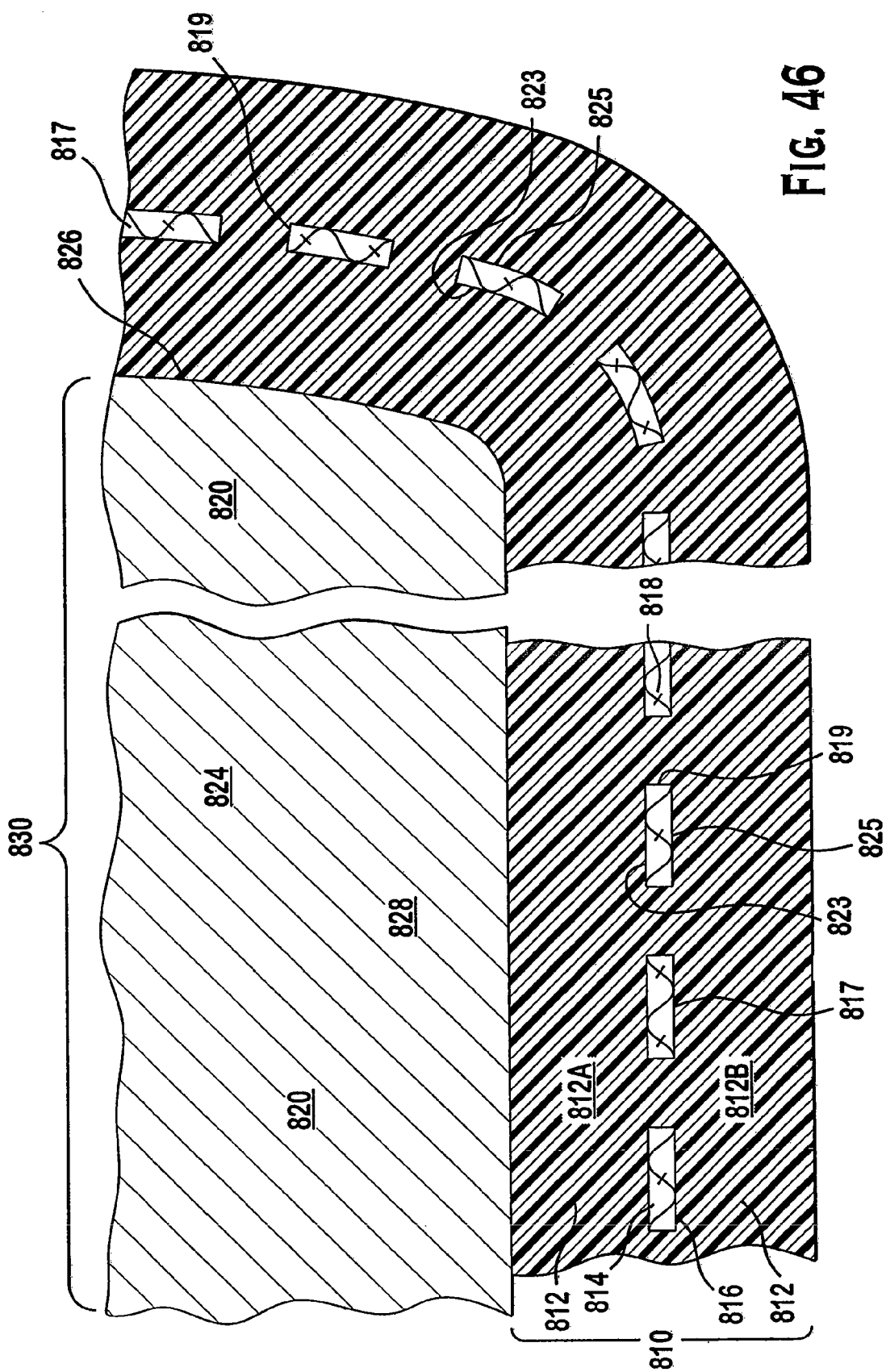
FIG. 46 is a cross-sectional view of another embodiment of the material of the present invention illustrating a single layer vibration dissipating material with a support structure embedded therein, the material extends along a longitudinal portion of an implement and covers a proximal end thereof.

With reference to FIGS. 46-51 in particular, it is preferred that the material 810 have a single contiguous elastomer body 812. Referring to FIG. 46, the support structure has first and second major surfaces 823, 825. In one embodiment, the elastomer 812 extends through the support structure 817 so that the portion of the elastomer 812A contacting the first major support structure surface 823 (i.e., the top of the support structure 817) and the portion of the elastomer 812B contacting the second major support structure surface 825 (i.e., the bottom of the support structure) form the single contiguous elastomer body 812. Elastomer material provides vibration damping by dissipating vibrational energy. Suitable elastomer materials include, but are not limited, urethane rubbers, silicone rubbers, nitrile rubbers, butyl rubbers, acrylic rubbers, natural rubbers, styrene-butadiene rubbers, and the like. In general, any suitable elastomer or polymer material can be used to form the vibration dissipating layer 812.

Referring to FIGS. 47-51, the support structure 817 can be any one (or combination of) of a polymer, an elastomer, a plurality of fibers, a plurality of woven fibers, and a cloth. If the support structure 817 and the layer 812 are both polymers or both elastomers, then they can be the same or different from each other without departing from the scope of the present invention. If vibration dissipating material is 812 if formed of the same material as the support structure 817, then the support structure 817 can be made more rigid than the main layer 812 by embedding fibers 814 therein. It is preferable that the support structure 817 is generally more rigid than the vibration dissipating material 812.

Figure 48:
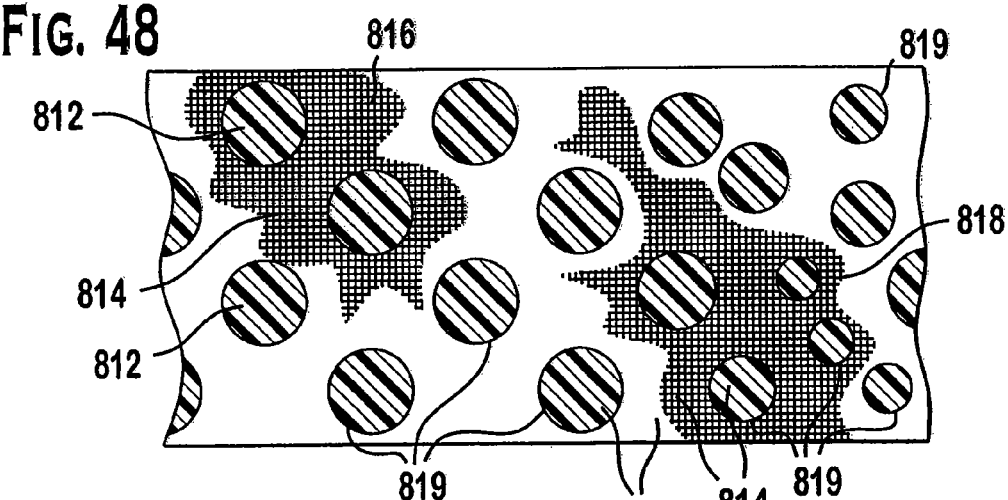
FIG. 48 is a cross-sectional view of an embodiment of the support structure as taken along the lines 48-48 of FIG. 47, the support structure is formed of polymer and/or elastomer and/or fibers, either of which may contain fibers, passageways extend through the support structure allowing the vibration dissipating material to penetrate the support structure.
Figure 49:
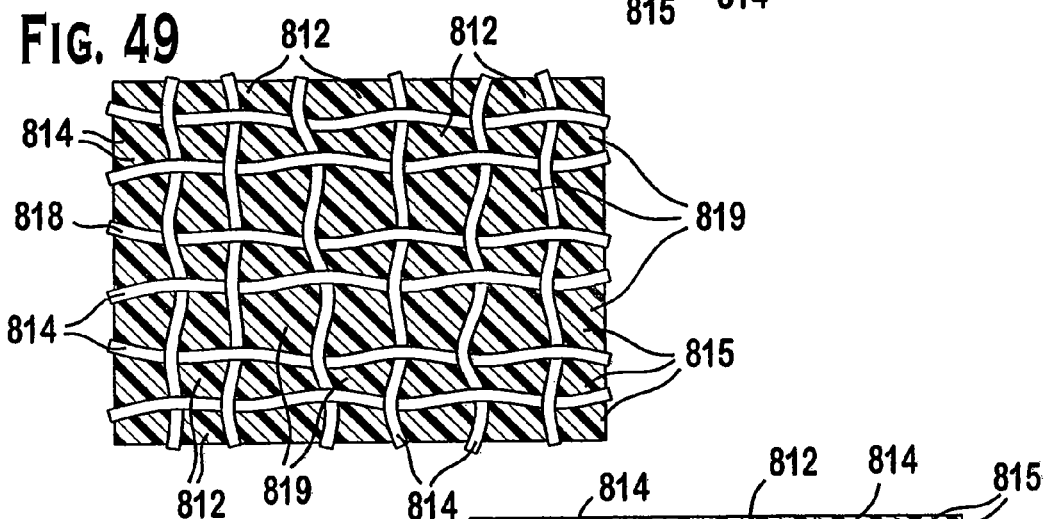
FIG. 49 is cross-sectional view of an alternate embodiment of the support structure as viewed in a manner similar to that of FIG. 48 illustrating a support structure formed by woven fibers, passageways through the woven fibers allow the support structure to be penetrated by the vibration dissipating material.
Figure 50:
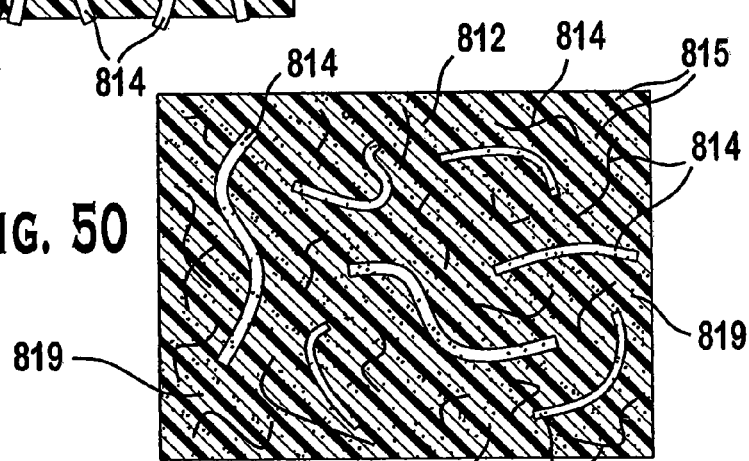
FIG. 50 is cross-sectional view of another alternate support structure as viewed in a manner similar to that of FIG. 48, the support structure formed by plurality of fibers, passageways past the fibers allow the vibration dissipating material to penetrate the support structure.
Figure 51:
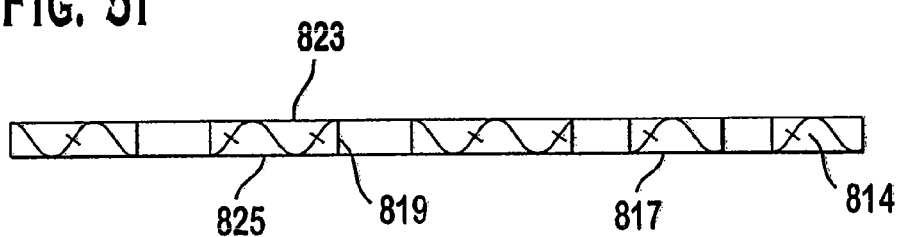
FIG. 51 is a side elevational view of the support structure of FIG. 48.

Referring specifically to FIG. 48, the support structure 817 may be formed of an elastomer that may but does not necessarily, also have fibers 814 embedded therein (exemplary woven fibers are shown throughout portions of FIG. 8). Referring to FIG. 49, the support structure 817 may be formed by a plurality of woven fibers 818. Referring to FIG. 50, the support structure 817 may be formed by a plurality of fibers 814. Regardless of the material forming the support structure 817, it is preferable that passageways 819 extend into the support structure 817 to allow the elastomer 812 to penetrate and embed the support structure 817. The term "embed," as used in the claim and in the corresponding portions of the specification, means "contact sufficiently to secure thereon and/or therein."

Figure 47:
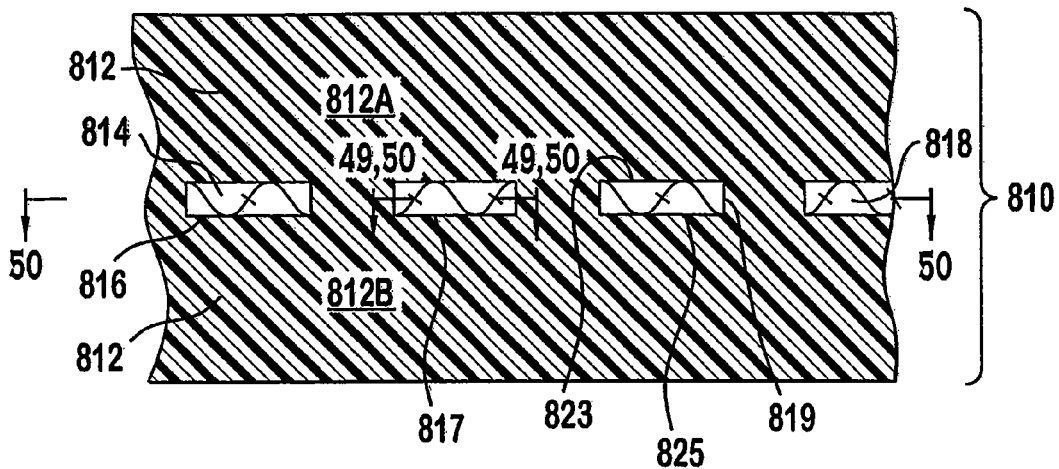
Figure 47A:
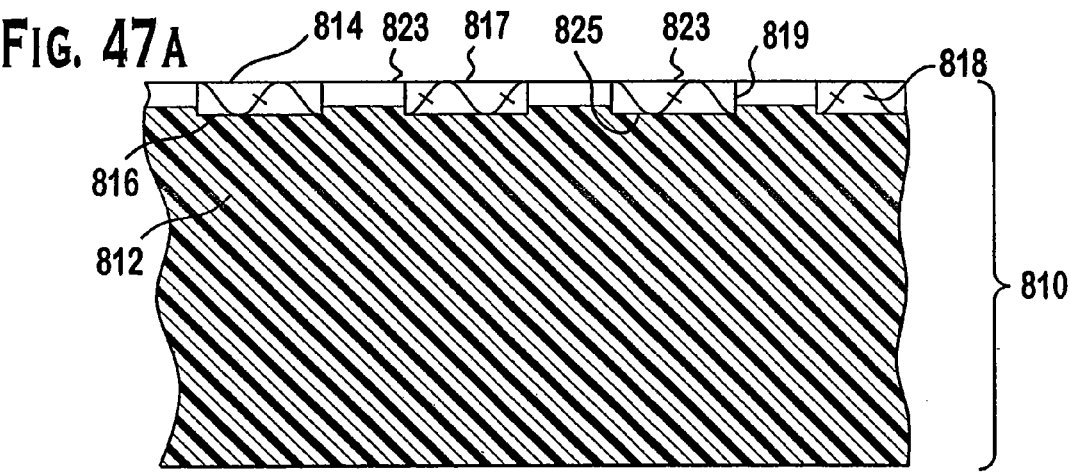
FIG. 47A is a cross-sectional view of another embodiment of the material of the present invention with the support structure embedded thereon and the vibration dissipating material penetrating the support structure.
Figure 47B:
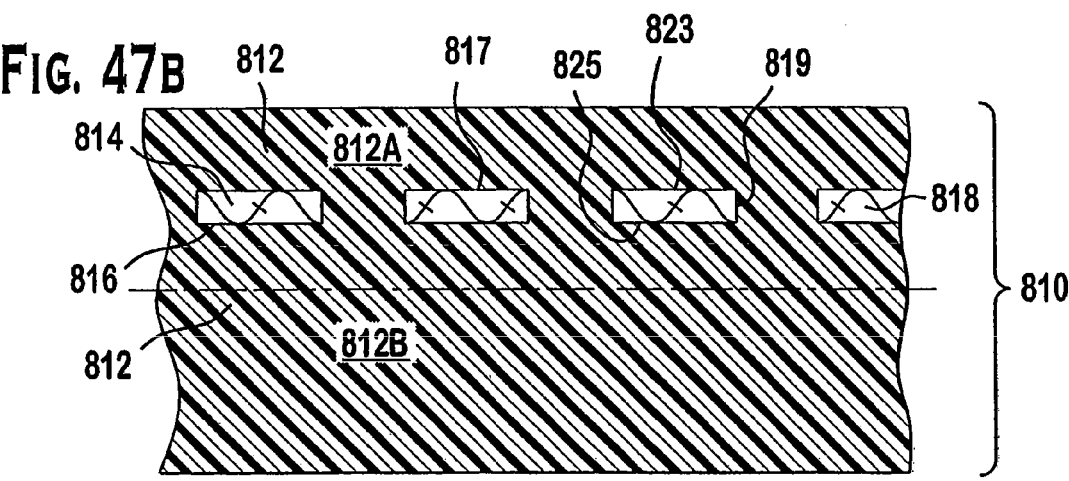
FIG. 47B is cross-sectional view of another embodiment of the material of the present invention with the support structure embedded within the vibration dissipating material and the vibration dissipating material penetrating the support structure, the support structure is positioned off center within the vibration dissipating material.

Accordingly, the support structure 817 shown in FIG. 47A is embedded by the elastomer 812 even though the elastomer 812 does not fully enclose the support structure 817. Additionally, as shown in FIG. 47B, the support structure 817 can be located at any level or height within the elastomer 812 without departing from the scope of the present invention. While the passageways 819 are shown as extending completely through the support structure 817, the invention includes passageways 819 that extend partially through the support structure 817.

Referring again to FIG. 47A, in one embodiment, it is preferred that the support structure 817 be embedded on the elastomer 812, with the elastomer penetrating the support structure 817. The support structure 817 being generally along a major material surface 838 (i.e., the support structure 817 is generally along the top of the material).

The fibers 814 are preferably, but not necessarily, formed of aramid fibers. Referring to FIG. 49, the fibers 814 can be woven to form a cloth 816 that is disposed on and/or within the elastomer 812. The cloth layer 816 can be formed of woven aramid fibers or other types of fiber. The aramid fibers 814 block and redirect vibrational energy that passes through the elastomer 812 to facilitate the dissipation of vibrations. The aramid fibers 818 redirect vibrational energy along the length of the fibers 818. Thus, when the plurality of aramid fibers 818 are woven to form the cloth 816, vibrational energy emanating from the implement 820 that is not absorbed or dissipated by the elastomer layer 812 is redistributed evenly along the material 810 by the cloth 816 and preferably also further dissipated by the cloth 816.

It is preferable that the aramid fibers 818 are formed of a suitable polyamide fiber of high tensile strength with a high resistance to elongation. However, those of ordinary skill in the art will appreciate from this disclosure that any aramid fiber suitable to channel vibration can be used to form the support structure 817 without departing from scope of the present invention. Additionally, those of ordinary skill in the art will appreciate from this disclosure that loose aramid fibers or chopped aramid fibers can be used to form the support structure 817 without departing from the scope of the present invention. The aramid fibers may also be formed of fiberglass or the like.

When the aramid fibers 818 are woven to form the cloth 816, it is preferable that the cloth 816 include at least some floating aramid fibers 818. That is, it is preferable that at least some of the plurality of aramid fibers 818 are able to move relative to the remaining aramid fibers 818 of the cloth 816. This movement of some of the aramid fibers 818 relative to the remaining fibers of the cloth converts vibrational energy to heat energy.

Figure 52:
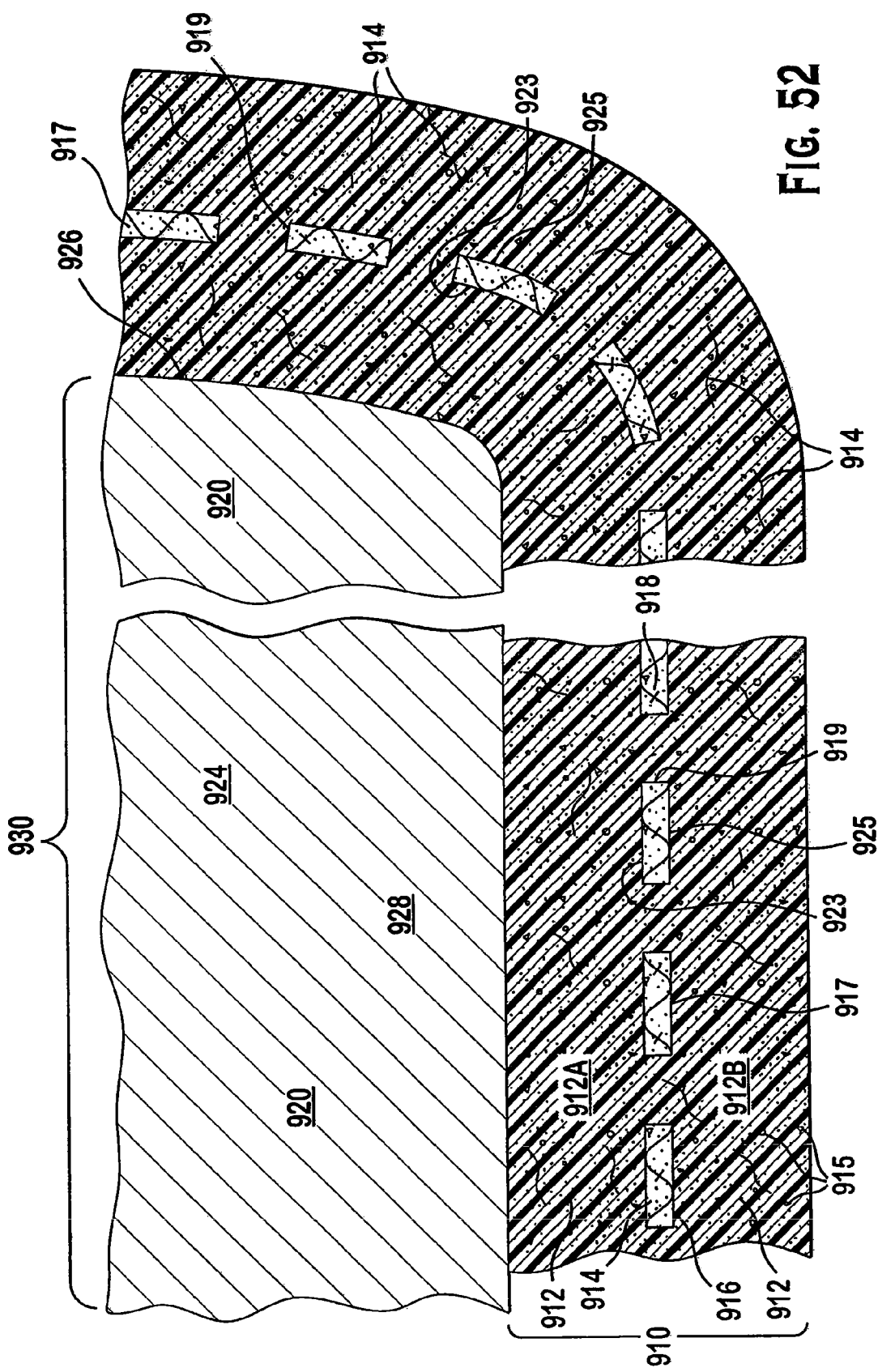
FIG. 52 is a cross-sectional view of another embodiment of the material of the present invention illustrating a single layer vibration dissipating material with a support structure embedded therein, the material extends along a longitudinal portion of an implement and covers a proximal end thereof.
Figure 53:
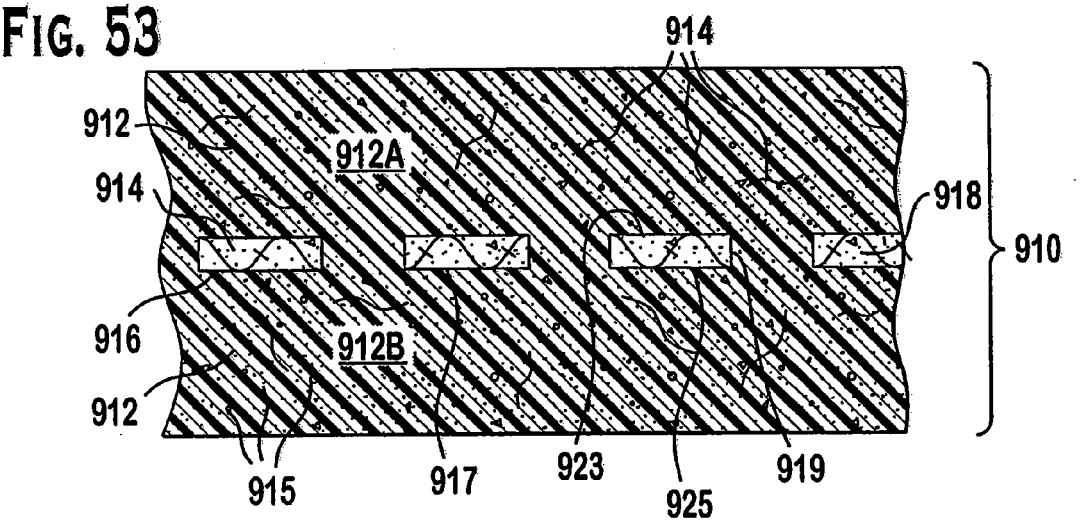

With reference to FIGS. 52-53, the elastomer layer 912 acts as a shock absorber by converting mechanical vibrational energy into heat energy. The embedded support structure 917 redirects vibrational energy and provides increased stiffness to the material 910 to facilitate a user's ability to control an implement 920 encased, or partially encased, by the material 910. The elastomer layer 912, 912A, or 912B may include a plurality of fibers 914 (further described below) or a plurality of particles 915 (further described below). The incorporation of the support structure 917 on and/or within the material 910 allows the material 910 to be formed by a single elastomer layer without the material 910 being unsuitable for at least some of the above-mentioned uses. The support structure 917 may also include a plurality of fibers 914 or a plurality of particles 915. However, those of ordinary skill in the art will appreciate from this disclosure that additional layers of material can be added to any of the embodiments of the present invention disclosed below without departing from the scope of the invention.

In the situation where the support structure 917 is formed by a second elastomer layer, the two elastomer layers can be secured together via an adhesive layer, discreet adhesive locations, or using any other suitable method to secure the layers together. Regardless of the material used to form the support structure 917, the support structure is preferably located and configured to support the first elastomer layer (see FIGS. 53-53B).

It is preferred that the material 910 have a single contiguous elastomer body 912. Referring to FIG. 52, the support structure has first and second major surfaces 923, 925. In one embodiment, the elastomer 912 extends through the support structure 917 so that the portion of the elastomer 912A contacting the first major support structure surface 923 (i.e., the top of the support structure 917) and the portion of the elastomer 912B contacting the second major support structure surface 925 (i.e., the bottom of the support structure) form the single contiguous elastomer body 912. Elastomer material provides vibration damping by dissipating vibrational energy. Suitable elastomer materials include, but are not limited, urethane rubbers, silicone rubbers, nitrile rubbers, butyl rubbers, acrylic rubbers, natural rubbers, styrene-butadiene rubbers, and the like. In general, any suitable elastomer or polymer material can be used to form the vibration dissipating layer 912.

Figure 53A:
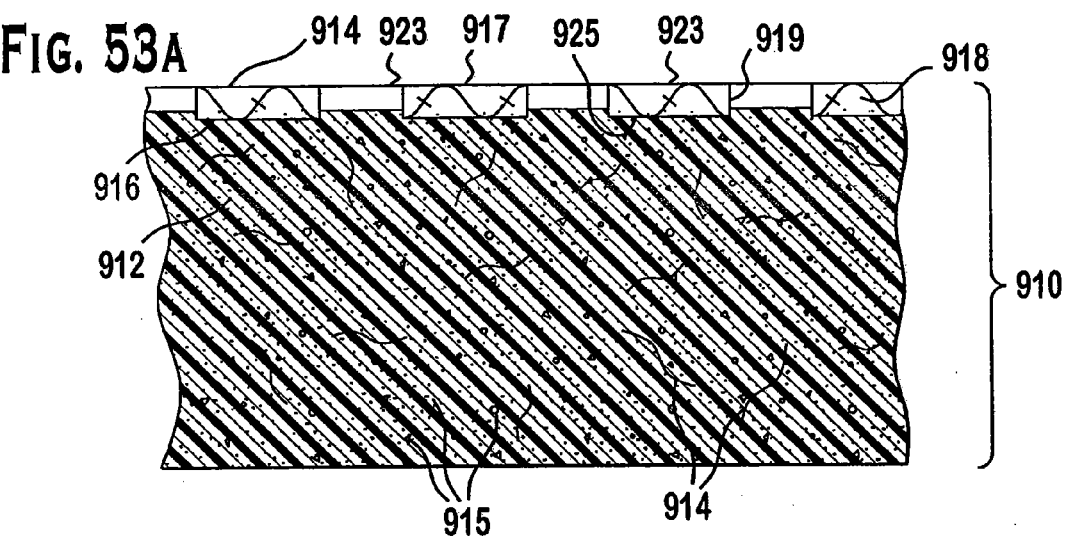
FIG. 53A is a cross-sectional view of another embodiment of the material of the present invention with the support structure embedded thereon and the vibration dissipating material penetrating the support structure.
Figure 53B:
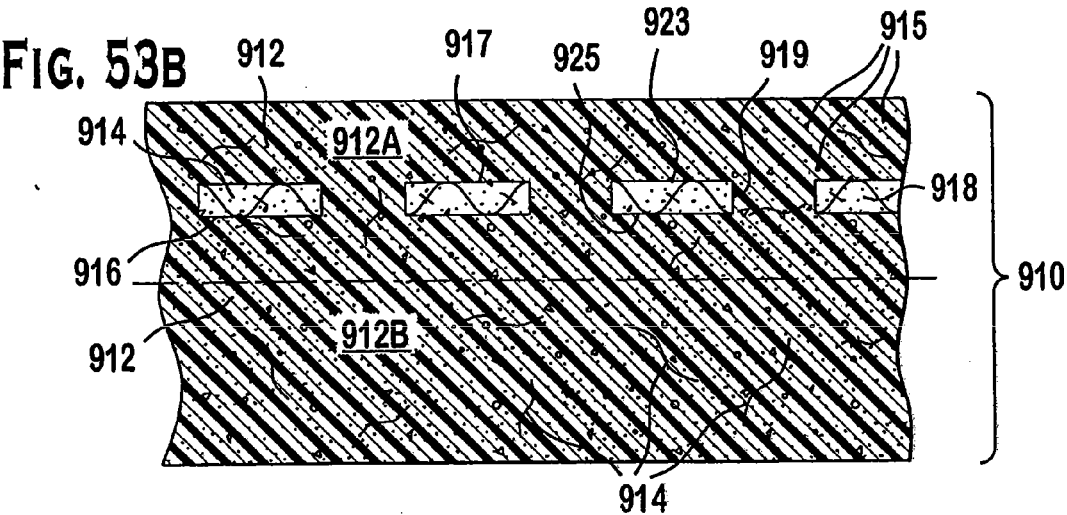
FIG. 53B is cross-sectional view of another embodiment of the material of the present invention with the support structure embedded within the vibration dissipating material and the vibration dissipating material penetrating the support structure, the support structure is positioned off center within the vibration dissipating material.

Referring to FIG. 53A, in one embodiment, it is preferred that the support structure 917 be embedded on the elastomer 912, with the elastomer penetrating the support structure 917. The support structure 917 being generally along a major material surface 938 (i.e., the support structure 917 is generally along the top of the material).

The fibers 914 are preferably, but not necessarily, formed of aramid fibers. However, the fibers can be formed from any one or combination of the following: bamboo, glass, metal, elastomer, polymer, ceramics, corn husks, and/or any other renewable resource. By using fibers from renewable resources, production costs can be reduced and the environmental friendliness of the present invention can be increased.

Particles 915 can be located in either an elastomer layer 912, 912A, and/or 912B and/or in the support structure 915. The particles 915 increase the vibration absorption of the material of the present invention. The particles 915 can be formed of pieces of glass, polymer, elastomer, chopped aramid, ceramic, chopped fibers, sand, gel, foam, metal, mineral, glass beads, or the like. Gel particles 915 provide excellent vibration dampening due their low durometer rating. One exemplary gel that is suitable for use the present invention is silicone gel. However, any suitable gel can be used without departing from the present invention.

In addition to use with implements, sleeves, covers, and the like described above, the material can be used as an athletic tape, padding, bracing material, or the like (as shown in FIGS. 69-78) without departing from the scope of the present invention. Referring to FIGS. 69-78; an athletic tape for wrapping a portion of a person's body; a material having a stretch axis and being adapted to regulate energy by disputing and partially dissipating energy exerted thereon; a padding for covering a portion of a person's body or an object; and/or a brace for wrapping a portion of a person's body is shown.

When the material of the present invention is used to form athletic tape, that athletic tape provides a controlled support for a portion of the person's body. The athletic tape includes a tape body 64 that is preferably stretchable along a longitudinal axis 48 (or stretch axis 50) from a first position to a second position, in which the tape body 64 is elongated by a predetermined amount relative to the first position.

Figure 54:
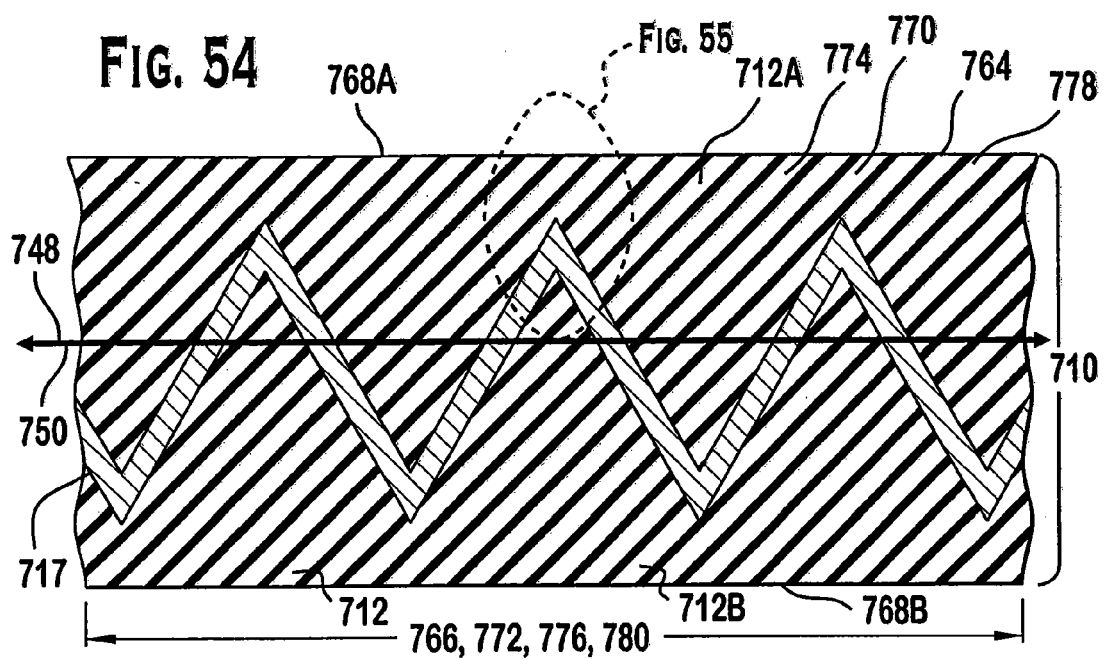
FIG. 54 is a cross-sectional view of yet another embodiment of the material of the present invention illustrating a single layer of vibration dissipating material with a support structure embedded therein; the support structure is disposed within the vibration dissipating material generally along a longitudinal axis in an at least partially non linear fashion so that a length of the support structure, as measured along a surface thereof, is greater than the length of the vibration dissipating material as measured along the longitudinal axis, of the material body.

FIGS. 54 and 56 illustrate another embodiment of the material of the present invention in the first and second positions, respectively. FIGS. 57 and 58 illustrate an alternative embodiment of the material of the present invention in the first and second positions, respectively.

As described below, the configuration of the support structure 17 within the vibration absorbing layer 12 allows the predetermined amount of elongation to be generally fixed so that the athletic tape provides a controlled support that allows limited movement before applying a brake on further movement of the wrapped portion of a person's body. This facilitates movement of a wrapped joint while simultaneously dissipating and absorbing vibration to allow superior comfort and performance as compared to that experienced with conventional athletic tape. While the predetermined amount of elongation can be set to any value, it is preferably less than twenty (20%) percent. The predetermined amount of elongation is more preferably less than two (2%) percent. However, depending on the application any amount of elongation can be used with the material 10 of the present invention.

The tape body 64 preferably includes a first elastomer layer 12 that defines a tape length 66, as measured along the longitudinal axis 48, of the tape body 64. The support structure 17 is preferably disposed within the elastomer layer 12 generally along the longitudinal axis 48 in an at least partially non linear fashion while the tape body is in the first position so that a length of the support structure 17, as measured along a surface thereof, is greater than the tape length 66 of the first elastomer layer 12. It is preferred, by not necessary, that the support structure 17 (or ribbon material) is positioned in a generally sinusoidal fashion within the elastomer layer 12 while the tape body 64 is in the first position. However, the support structure 17 can be positioned in an irregular fashion without departing from the scope of the present invention. As described above, the support structure 17 and/or the elastomer layer 12 can include particles, fibers, or the like (as shown in FIGS. 12 and 13).

Referring to FIGS. 56 and 58, when the tape body 64 is stretched into the second position, the support structure 17 is preferably at least partially straightened so that the support structure 17 is more linear (or in the case of other materials, the support structure 17 would likely be thinner), relative to when the tape body 64 is in the first position. The straightening of the support structure causes energy to be dissipated and preferably generally prevents further elongation of the elastomer layer 12 along the longitudinal axis 48 past the second position. Energy dissipation occurs due to the stretching of the material of the support structure 17 and can occur due to the separation or partial pulling away of the support structure 17 from the attached elastomer layer 12.

Figure 55:
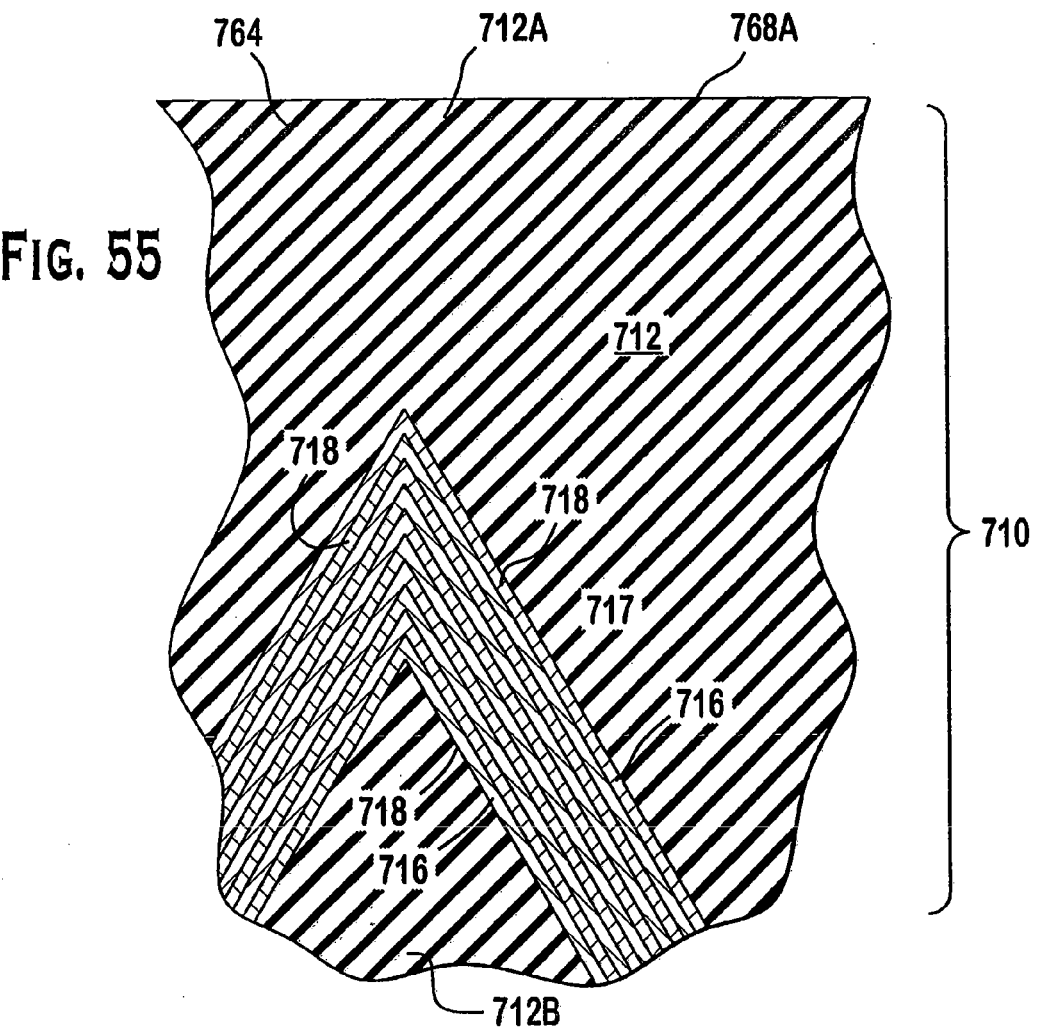
FIG. 55 is an enlarged broken away view of the area enclosed by the dashed lines labeled "FIG. 54" in FIG. 54 and illustrates that the "overall support structure" can actually be formed by a plurality of individual stacked support structures (which can be the same or different from each other) or a successive plurality of stacked fibers and/or a successive plurality of stacked cloth layers.

Referring to FIG. 55, the "overall support structure" 17 may comprise a plurality of stacked support structures, fibers 18, and/or cloth layers 16. It is preferred that the plurality of fibers include aramid fibers or other high tensile strength fibrous material. Alternatively, the plurality of fibers may be formed of fiberglass material or be woven into a ribbon or cloth. The support structure can include any one (or combination) of a polymer, an elastomer, particles; fibers; woven fibers; a cloth; a plurality of cloth layers; loose fibers, chopped fibers, gel particles, particles, sand, or the like without departing from the scope of the present invention.

As detailed above, the support structure 17 and/or the elastomer layer 12 may include a plurality of particles therein. Such particles may include any one or combination of gel particles, sand particles, glass beads, chopped fibers, metal particles, foam particles, sand, or any other particle in parting desirable vibration dissipation characteristics to the material 10.

Referring to FIGS. 54 and 55, it is preferred that the tape body 64 have top and bottom surfaces 68A, 68B, respectively. The bottom surface 68B faces the portion of the person's body when the athletic tape 710 is wrapped thereover. When the support structure 717 is formed by a plurality of fibers 718, it is preferable that the plurality of fibers 718 define multiple stacked fiber layers between the top and bottom surfaces 768A, 768B. It is preferable that the plurality of fibers 718 are stacked between four (4) and sixteen (16) times between the top and bottom surfaces 768A, 768B. It is more preferable still that the plurality of fibers are stacked ten (10) times. As described above, the plurality of fibers 718 may include metal fibers, high tensile strength fibrous material, ceramic fibers, polymer fibers, elastomer fibers, or the like without departing from the scope of the present invention. As shown in FIG. 764, the support structure 717 may be disposed only partially within or on the elastomer layer generally along the longitudinal axis without departing from the scope of the present invention.

Referring again to FIGS. 54-58, the material of the present invention can be an all purpose material for use as desired by a person to regulate energy by distributing and partially dissipating energy exerted thereon. When the material 710 of the present is used as an all purpose material, the all purpose material 710 includes a material body 770 that is elongateable along the stretch axis 750 from a first position (shown in FIGS. 54 and 57) to a second position (shown in FIGS. 55 and 58), in which the material body 770 is elongated by a predetermined amount relative to the first position. The stretch axis 750 is preferably determined during manufacturing by the orientation and geometry of the support structure 717 which preferably limits the directions in which the material body 770 can elongate. If multiple separate material bodies 770 are stacked together, it may be desirable to have the stretch axis 750 of the individual material bodies 770 oriented askew from each other.

The first elastomer layer 712 defines a material length 772, as measured along the stretch axis 750 of the material body 770. The support structure 717 is preferably disposed within the elastomer layer 712 generally along the stretch axis 750 in an at least partially non linear fashion while the material body 770 is in the first position so that a length of the support structure, as measured along the surface thereof, is greater than the material length 772 of the first elastomer layer. When the material body 770 is elongated into the second position, the support structure 717 is at least partially straightened so that the support structure is more linear, relative to when the material body 770 is in the first position.

The support structure 717 is preferably positioned in a sinusoidal fashion within any of the materials 710 of the present invention. The support structure 717 or ribbon may also be positioned in the form of a triangular wave, square wave, or an irregular fashion without departing from the scope of the present invention.

Any of the materials of the present invention may be formed with an elastomer layer 712 formed by silicone or any other suitable material. Depending upon the application, the vibration absorbing material 712 may be a thermoset and/or may be free of voids therein.

Any of the embodiments of the material 710 can be used as an implement cover, grip, athletic tape, an all purpose material, a brace, and/or padding. When the material 710 of the present invention is used as part of a padding, the padding includes a padding body 774 that is elongateable along the stretch axis from a first position to a second position, in which the padding body 774 is elongated by a predetermined amount relative to the first position. The padding includes a first elastomer layer 712 which defines a padding length 776, as measured along the stretch axis 750 of the padding body 774.

The support structure 717 is disposed within the elastomer layer 712 generally along the stretch axis 750 in an at least partially non linear fashion while the padding body 774 is in the first position so that a length of the support structure 717, is measured along a surface thereof, is greater than the padding length 776 of the first elastomer layer 712. When the padding body 774 is elongated into the second position, the support structure 717 is at least partially straightened so that the support structure is more linear, relative to when the padding body 774 is in the first position. The straightening of the support structure 717 causes energy to be dissipated and generally prevents further elongation of the elastomer layer along the stretch axis 750 past the second position.

When the materials 710 of the present invention are incorporated as part of a brace, the brace provides a controlled support for a wrapped portion of a person's body. The brace includes a brace body 778 that is elongateable along the stretch axis 750 from a first position to a second position, in which the brace body 778 is elongated by a predetermined amount relative to the first position. The brace body includes a first elastomer layer 712 that defines a brace length 780, as measured along the stretch axis 750, of the brace body 778.

The support structure 717 is preferably disposed within the elastomer layer generally along the stretch axis 750 in an at least partially non linear fashion while the brace body 778 is in the first position so that a length of the support structure 717, as measured along a surface thereof, is greater than the brace length 780 of the first elastomer layer 712. When the brace body 778 is stretched into the second position, the support structure 717 is at least partially straightened so that the support structure 717 is more linear, relative to when the brace body 778 is in the first position. The straightening of the support structure 717 causes energy to be dissipated and preferably generally prevents further elongation of the elastomer layer 712 along the stretch axis past the second position. Those ordinarily skilled in the art will appreciate that any of the materials 710 of the present invention may be formed into a one piece brace that provides a controlled support as described above without departing from the scope of the present invention.

Referring to FIGS. 54 and 57, depending upon the geometry of the support structure 717 when the material 710 is in the first position, the amount of stretch of the material 710 can be selected. It is preferred that the percentage increase in the material length when the body 764, 770, 774, 778 moves from the first position to the second position is selected based on a desired range of motion. When the material 710 is configured as an athletic tape, the athletic tape may be wrapped about a portion of a person's body multiple times, if necessary, to form a brace. Alternatively, a single layer of material 710 can be wrapped on a person and secured in place using conventional athletic tape or the like. It is preferable that the successive wrappings of athletic tape are affixed to each other to form a generally one piece brace. This can be accomplished by using tape that is self fusing to allow multiple adjacent wrappings of the athletic tape to fuse together to form an integral piece. One method of fusing wrappings of the athletic tape is for the elastomer layer of each of the multiple adjacent wrappings to contact the elastomer layer of the adjacent wrappings to fuse together to form a single elastomer layer. Self fusing technology can be used with any of the materials 710 of the present invention and can be used in any of the applications for which those materials are suitable. By way of non limiting example, self fusing material 710 can be used with baseball bats, lacrosse sticks, tennis rackets, gun covers and wraps, implements, sports implements, tape, padding, braces, or the like.

Figure 59:
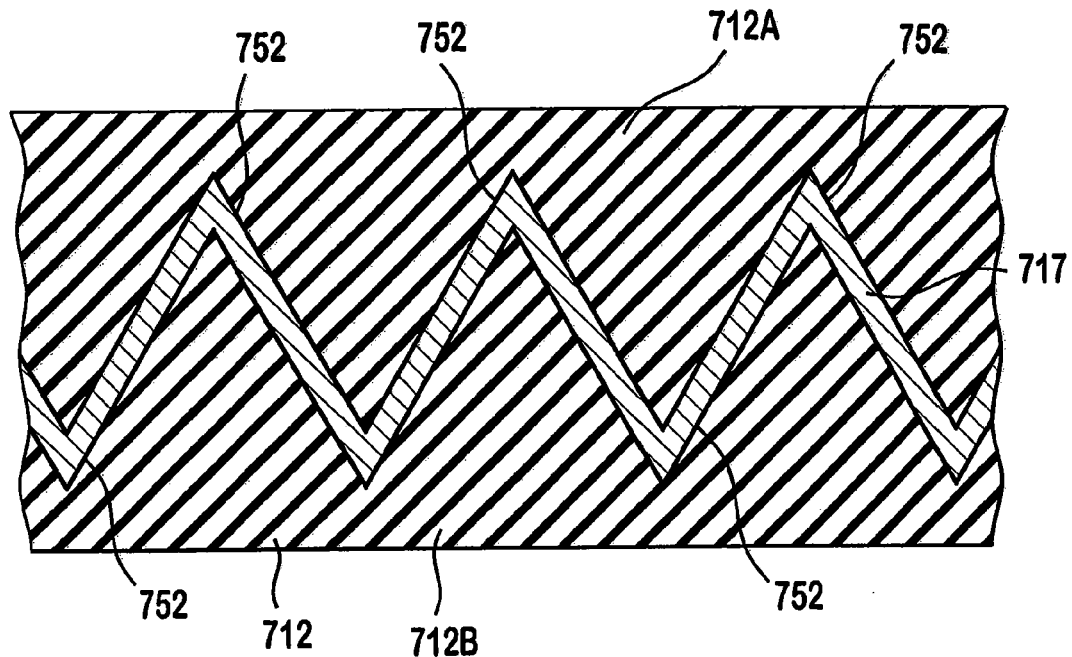
FIG. 59 is a cross-sectional view of another embodiment of the material of the present invention illustrating the support structure with an adhesive layer generally over its major surfaces to allow the elastomer material to be secured thereto rather than molded and/or extruded thereover.
Figure 60:
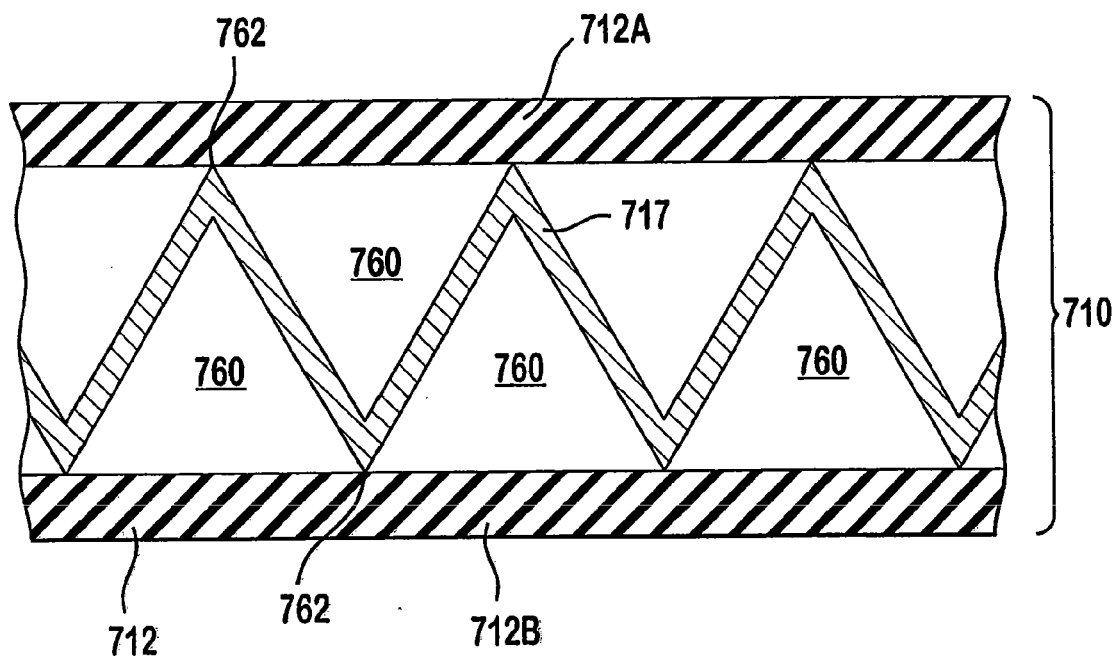
FIG. 60 is a cross-sectional view of another embodiment of the material of the present invention illustrating the support structure, or ribbon material, positioned between two spaced elastomer layers with the support structure's peaks molded, fastened, and/or otherwise affixed to the elastomer layer at a plurality of locations; air gaps are preferably present about the support structure to facilitate longitudinal stretching of the material; alternatively, the support structure can be secured only at its lateral ends (i.e., the left and right ends of the support structure viewed in FIG. 60) to the elastomer layers so that the remainder of the support structure moves freely within an outer sheath of elastomer material and functions as a spring/elastic member to limit the elongation of the material.
Figure 61:
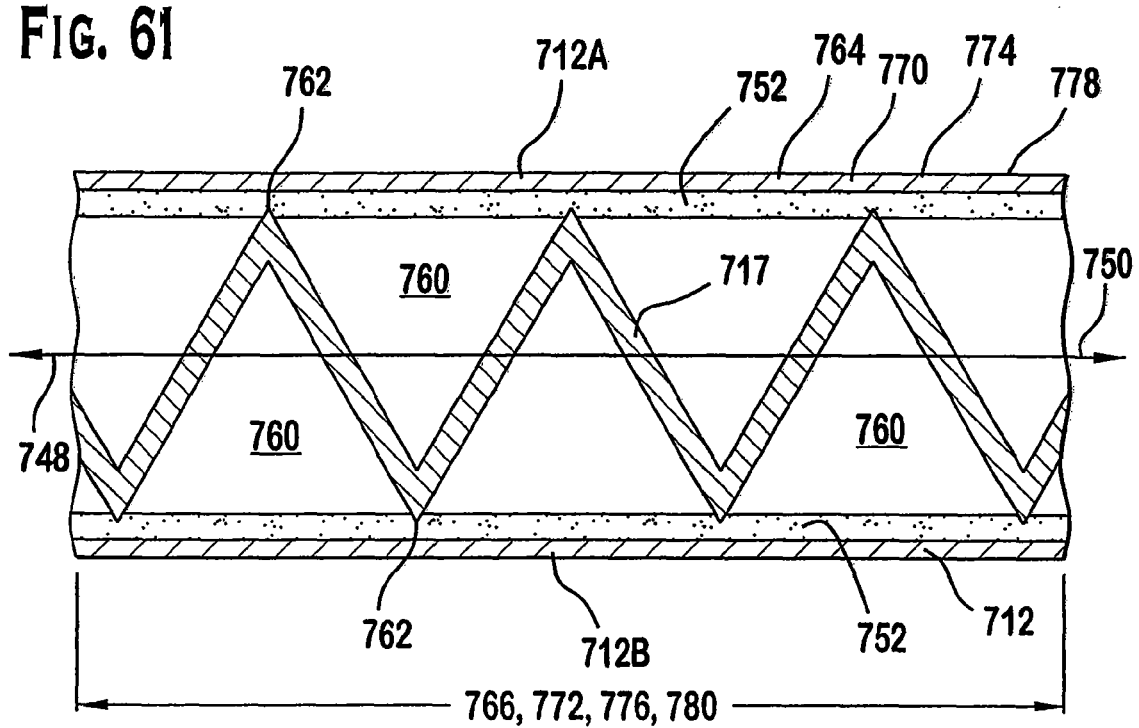
FIG. 61 is another embodiment of the vibration dissipating material of the present invention and is similar to the material shown in FIG. 60, except that the support structure's peaks are secured to the elastomer layers via an adhesive layer.
Figure 62:
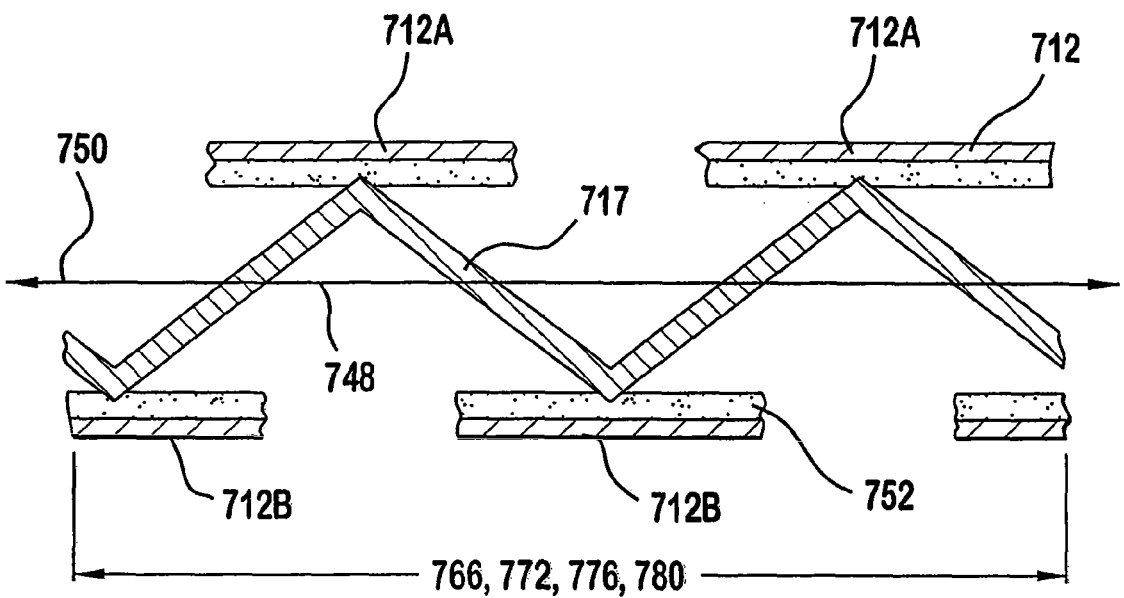
FIG. 62 is another embodiment of the vibration dissipating material of the present invention and illustrates the vibration dissipating material and any accompanying adhesive actually physically breaking when the support structure is elongated into the second position; the breaking of the vibration dissipating material results in further energy dissipation and vibration absorption in addition to that dissipated by the support structure.
Figure 63:
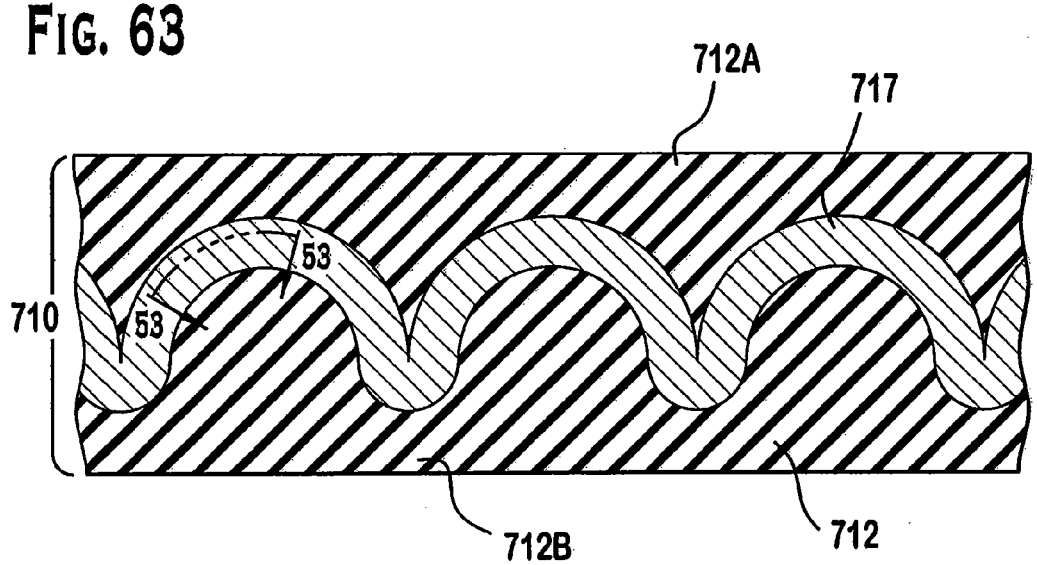
FIG. 63 is another embodiment of the vibration dissipating material of the present invention and illustrates that the support structure, or ribbon material, can be disposed in any geometry within the vibration dissipating material; additionally, individually rigid squares, buttons, or plates (not shown) can be positioned on one side of the material to further spread impact force along the surface of the material prior to the dissipation of vibration by the material in general; additionally, such buttons, plates, or other rigid surfaces can be attached directly to a mesh or other flexible layer that is disposed over the material shown in FIG. 63 so that impact force on one of the rigid members causes deflection of the entire mesh or other layer for energy absorption prior to vibration absorption by the material; the section line labeled 53-53 in this Figure signifies that it is possible that the support structure shown in FIG. 63 is generally the same as that illustrated in FIG. 53.
Figure 64:
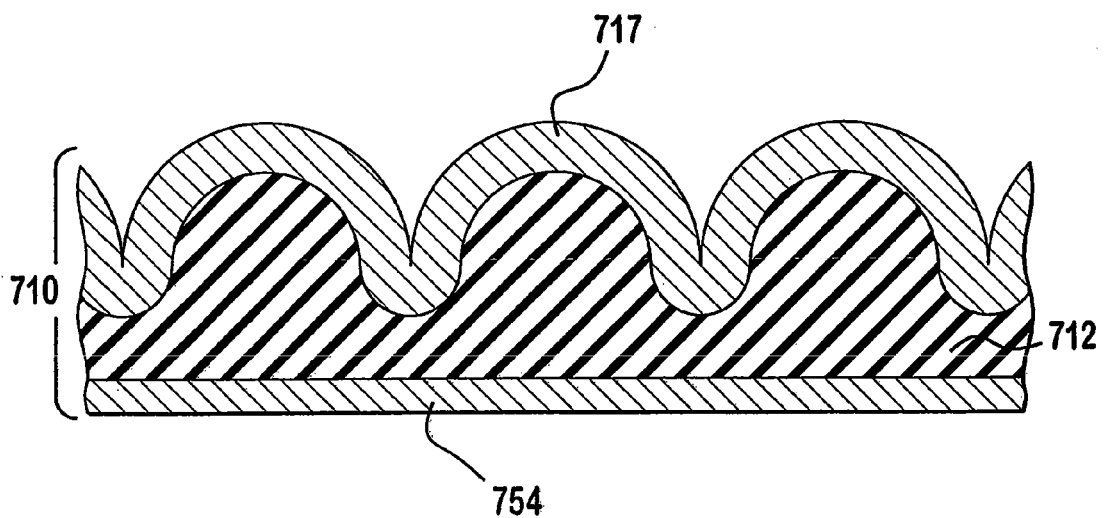
FIG. 64 is a cross-sectional view of another embodiment of the material of the present invention and illustrates that the support structure can be positioned generally along an outer surface of the vibration dissipating material without departing from the scope of the present invention.
Figure 65:
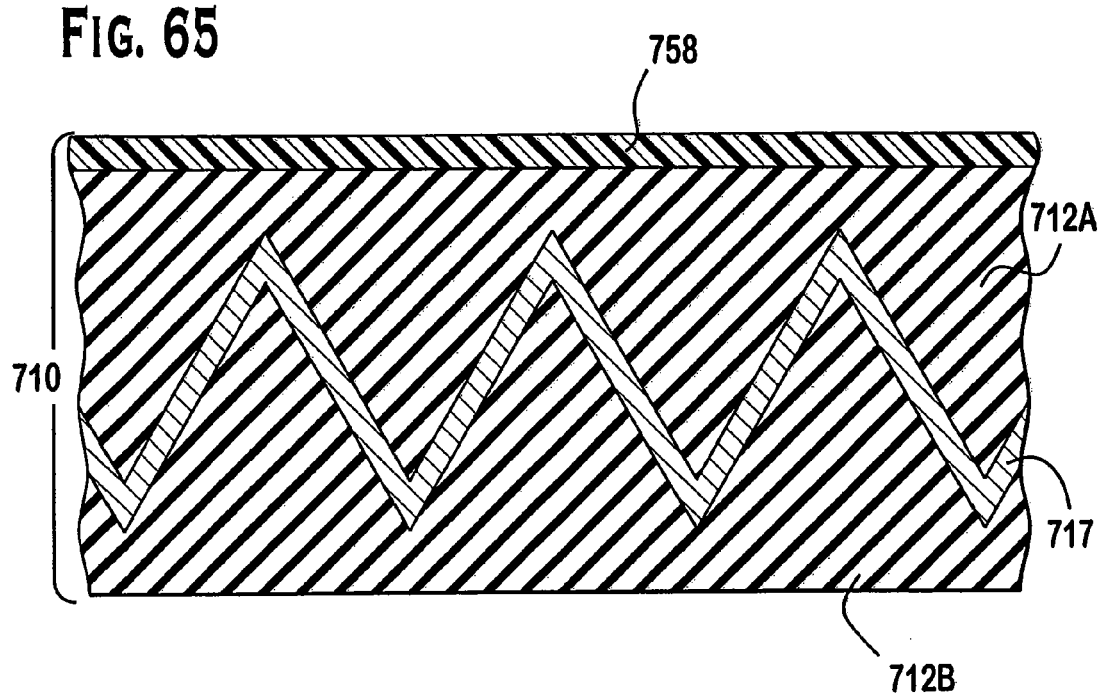
FIG. 65 is a cross-sectional view of another embodiment of the vibration dissipating material with a shrinkable layer of material disposed on a major surface thereof; the shrinkable material can be a heat shrinkable material or any other type of shrinking material suitable for use with the present invention; once the material is properly positioned, the shrinkable layer can be used to fix the material in position and, preferably, can also be used as a separate breakable layer to further dissipate vibration in a fashion similar to the breakable layer described in connection with FIG. 62.
Figure 66:
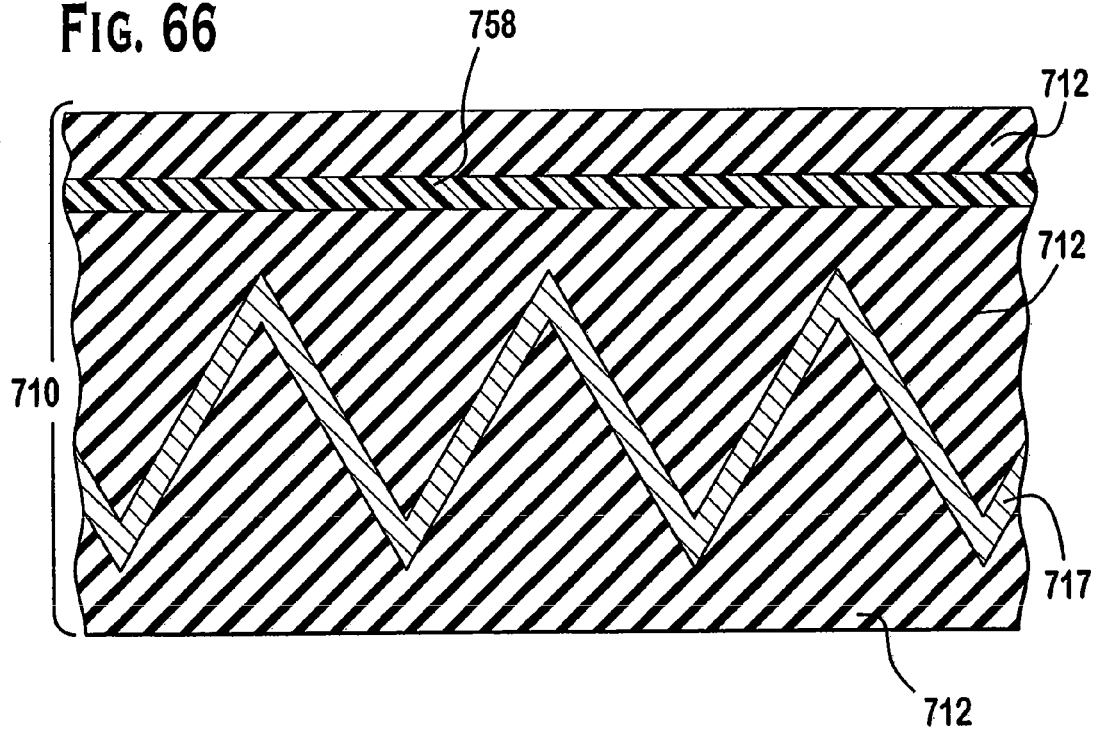
FIG. 66 is another embodiment of the vibration dissipating material of the present invention and illustrates the shrinkable layer disposed within the vibration dissipating material; the shrinkable layer can be a solid layer, a perforated layer, a mesh or netting, or shrinkable fibers.

Referring to FIGS. 59, 60, and 62, adhesive 52 may be used to connect the support structure 717 to the vibration absorbing material 712. Referring to FIGS. 60-62, air gaps 760 can be present proximate to the support structure 717 without departing from the scope of the present invention. Referring to FIG. 60, the material can be secured at its peak 762 to the vibrating absorbing material 712 or can be secured only at its ends with the vibration absorbing material 712 forming a protective sheath for the support structure 717 which would act as an elastic member in this instance.

Figure 67:
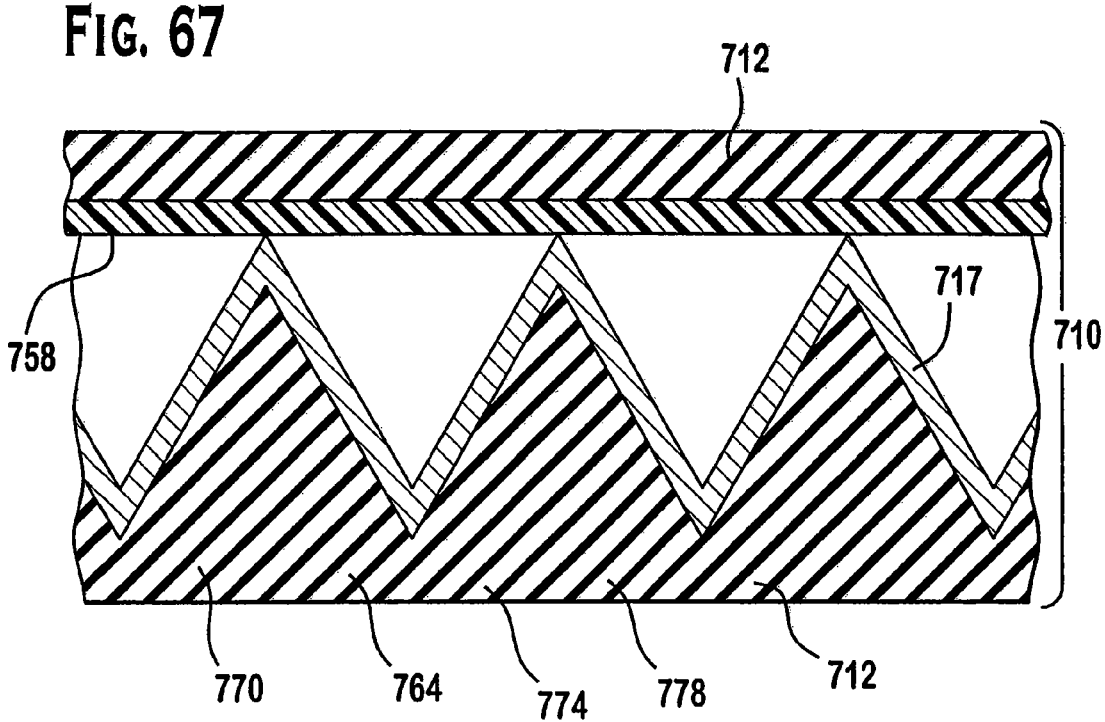
FIG. 67 is another embodiment of the vibration absorbing material of the present invention and illustrates the shrinkable layer being disposed over peaks of the support structure with an optional vibration absorbing layer thereover.
Figure 68:
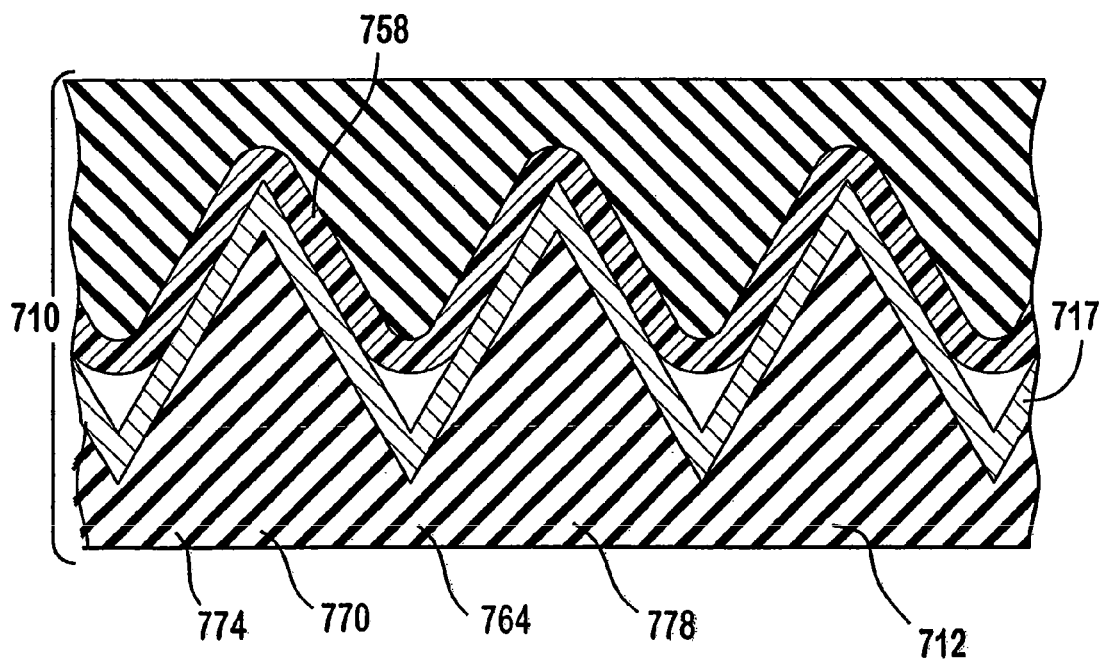
FIG. 68 is a cross-sectional view of the material of FIG. 67 when the shrinkable layer has been shrunk down over the support structure after the material is placed in a desired configuration; although the optional additional vibration absorbing material is not shown in FIG. 68, it can be left in position above the shrinkable layer to form a protective sheath or also pulled down into the gaps between the peaks of the support structure.
Figure 69:
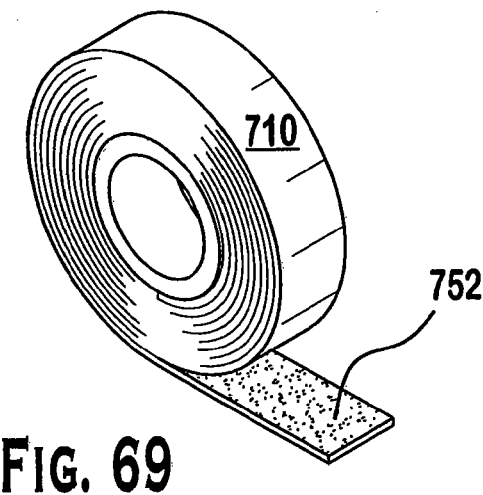
FIG. 69 illustrates the material of the present invention configured as athletic tape with an optional adhesive layer.
Figure 70:
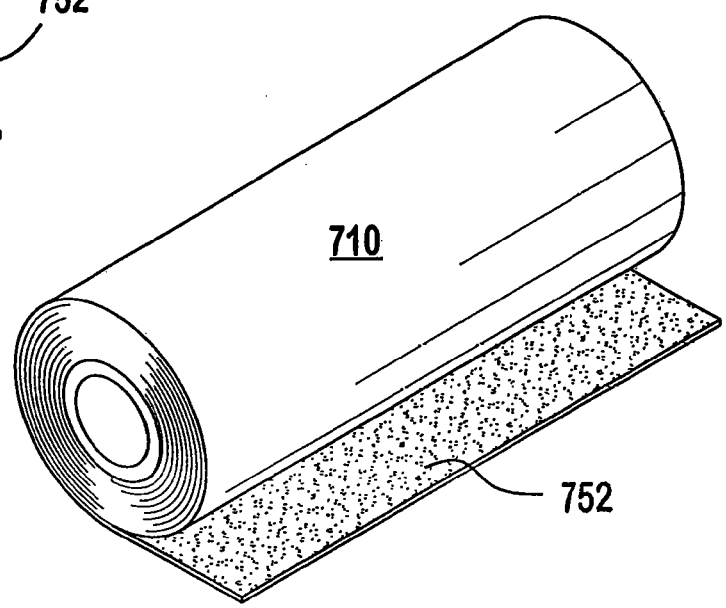
FIG. 70 illustrates the material of the present invention as a roll of material/padding/wide wrap material or the like with an optional adhesive layer thereon.
Figure 71:
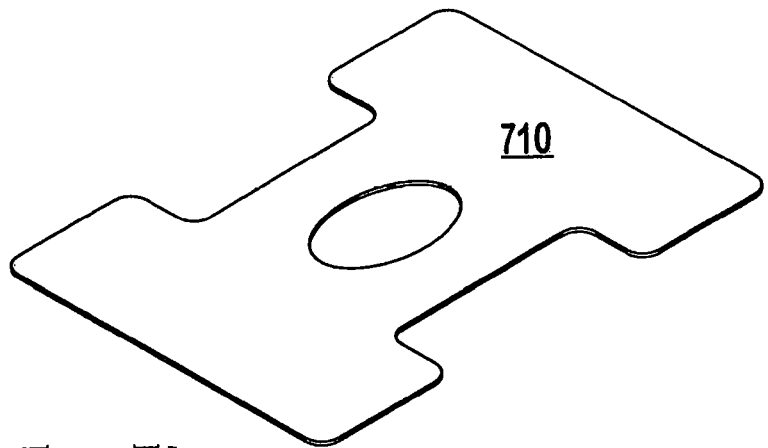
FIG. 71 illustrates the material of the present invention configured as a knee bandage.
Figure 72:
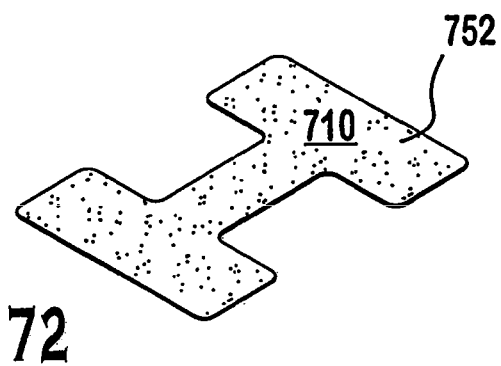
FIG. 72 illustrates the material of the present invention with an optional adhesive layer configured as a finger and/or joint bandage; while various bandages, wraps, padding, materials, tapes, or the like are shown, the material of the present invention can be used for any purpose or application without departing from the scope of the present invention.
Figure 73:
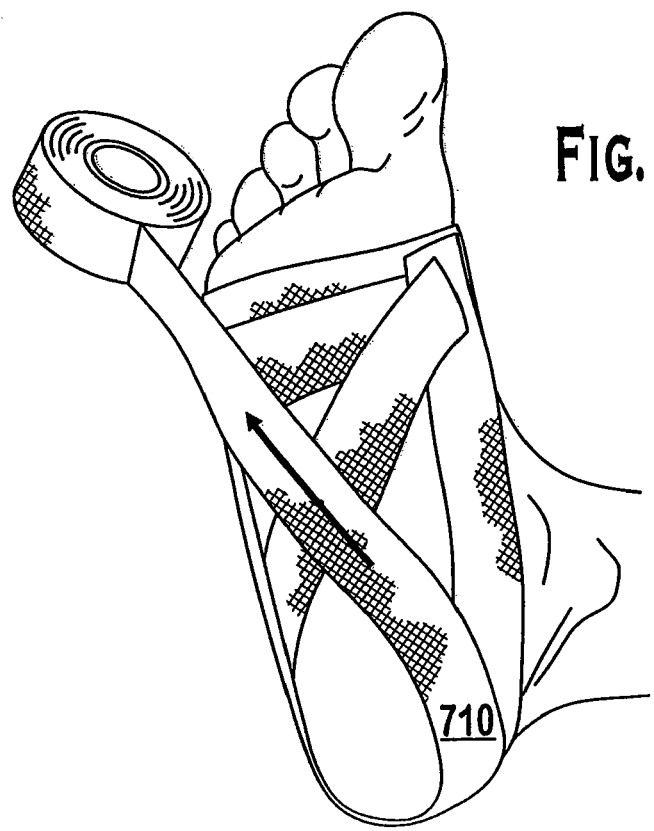
FIG. 73 illustrates the material of the present invention used to form a foot brace.
Figure 74:
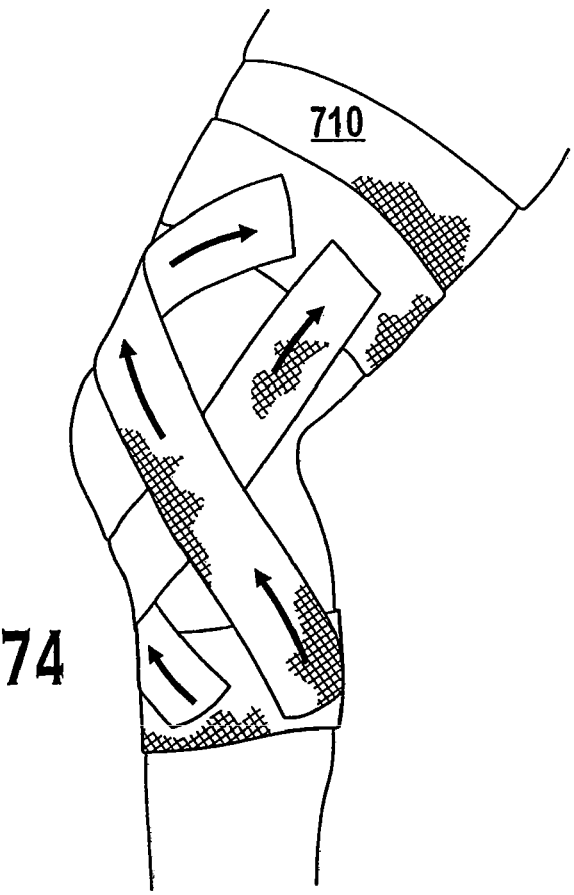
FIG. 74 illustrates the material of the present invention wrapped to form a knee supporting brace.
Figure 75:
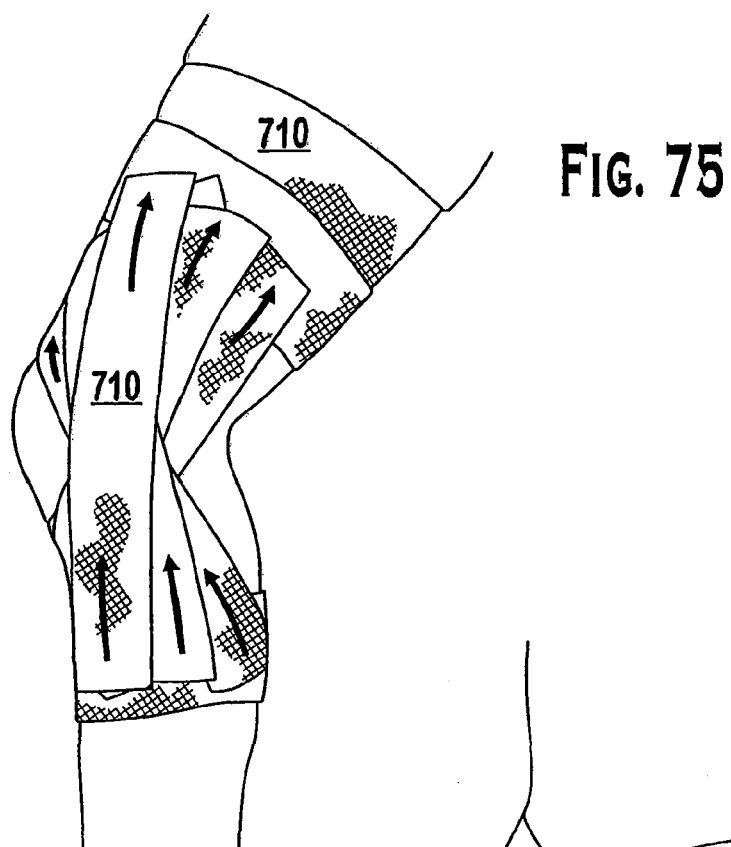
FIG. 75 illustrates additional layers of material used to brace the ligaments in a person's leg.
Figure 76:
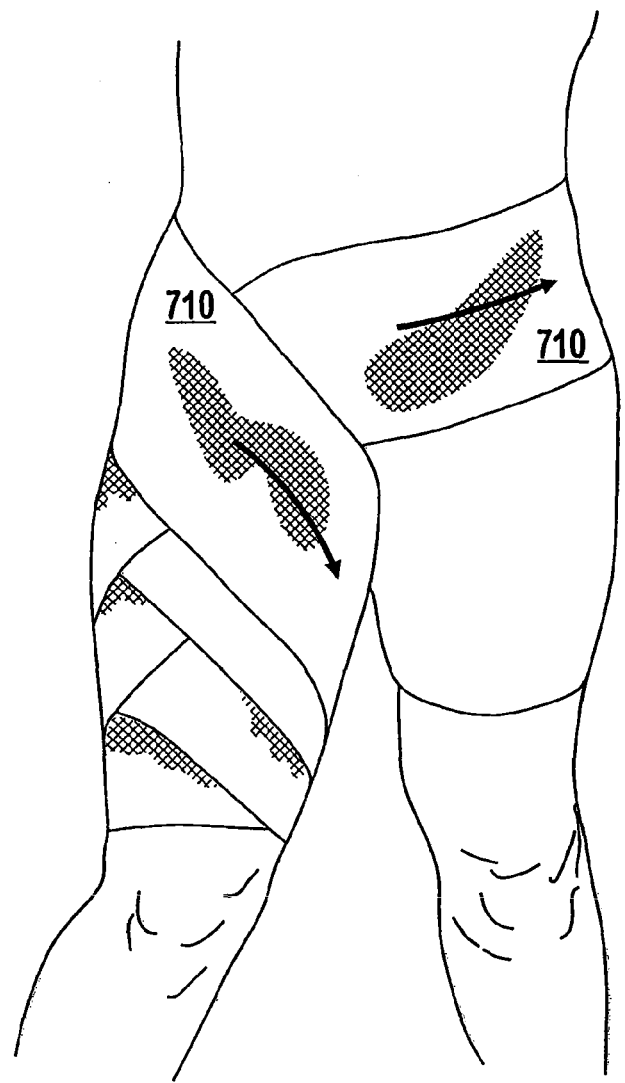
FIG. 76 illustrates the material of the present invention used to form a hip support.
Figure 77:
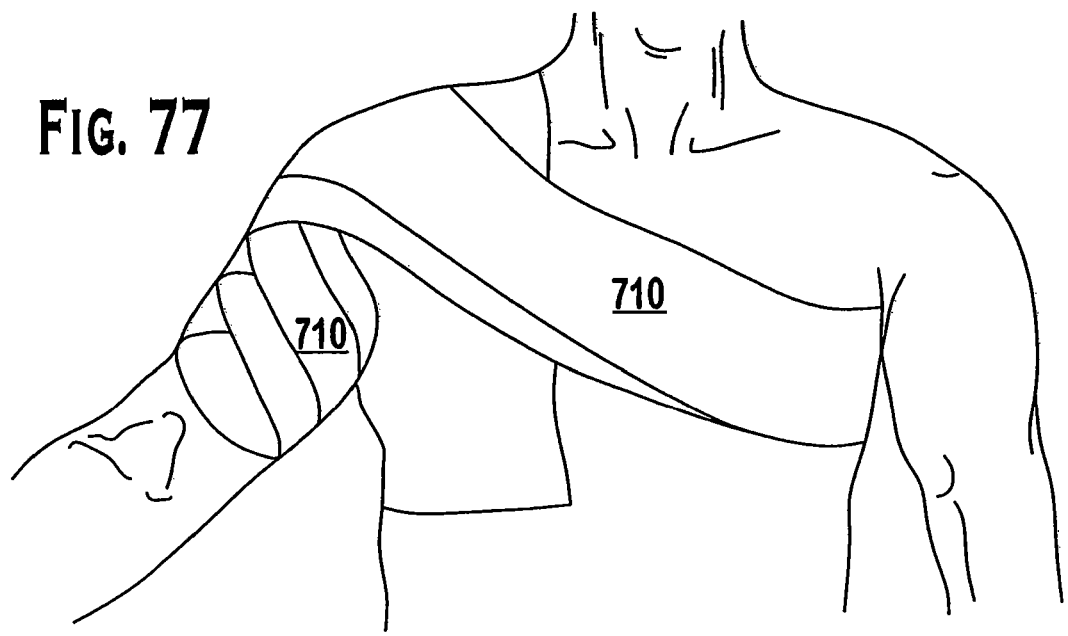
FIG. 77 illustrates the material of the present invention used to form a shoulder brace.
Figure 78:
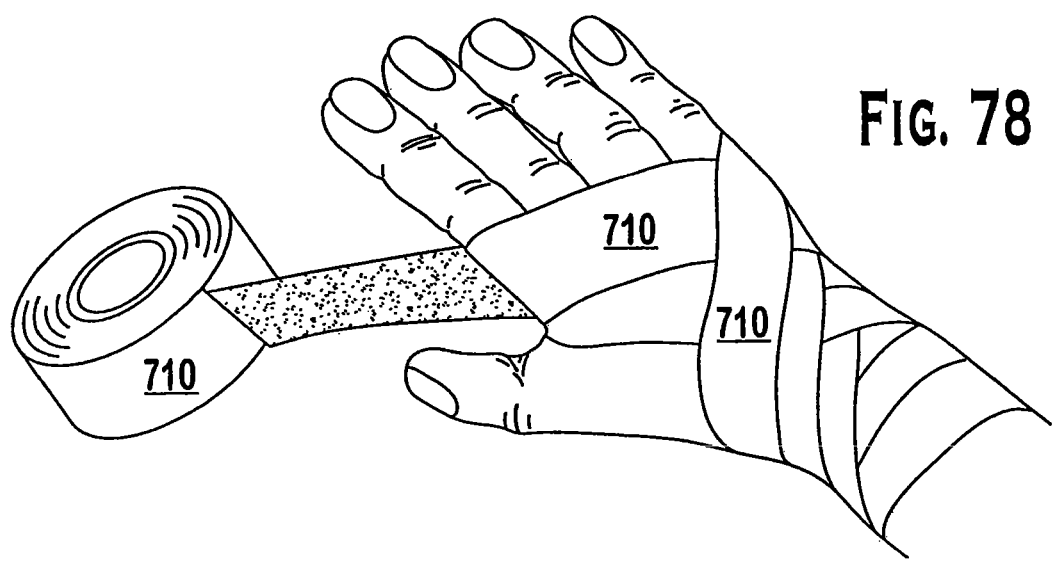
FIG. 78 illustrates the material of the present invention wrapped to form a hand and wrist brace; while the material of the present invention has been shown in conjunction with various portions of the person's body, those of ordinary skill in the art will appreciate from this disclosure that the material of the present invention can be used as an athletic brace, a medical support, or a padding for any portion of a person's body without the departing from the scope of the present invention.

FIGS. 65-68 illustrate the material 710 of the present invention incorporating a shrink layer 758 which can be used to secure the material 710 in position. Additionally, the shrinkable layer 758 may be configured to break when a certain stress threshold is reached to provide further energy dissipation. Referring to FIG. 67, a shrinkable layer 758 is in its pre-shrink configuration. Referring to FIG. 68, once the shrinkable layer 758 has been activated, the shrinkable layer 758 preferably deforms about one side of the support structure 717 to hold the material 710 in position. The shrinkable layer 758 can be heat or water activated. Alternative known activation methods are also suitable for use with the present invention.

FIG. 62 illustrates another embodiment of the present invention in which the vibration absorbing layer 712 is configured to break apart during the elongation of the support structure 717 to allow for greater energy dissipation.

Any of the materials 710 of the present invention can be used in conjunction with additional layers of rigid or flexible materials without departing from the scope of the present invention. For example, the materials 710 of the present invention may be used with a hard shell outer layer which is designed to dissipate impact energy over the entire material 710 prior to the material 710 deforming to dissipate energy. One type of rigid material that can be used in combination with the materials 710 of the present invention is molded foam. Molded foam layers preferably include multiple flex seams that allow portions of the foam layer to at least partially move relative to each other even though the overall foam layer is a single body of material. This is ideal for turning an impact force into a more general blunt force that is spread over a larger area of the material 710. Alternatively, individual foam pieces, buttons, rigid squares, or the like can be directly attached to an outer surface of any of the materials 710 of the present invention. Alternatively, such foam pieces, buttons, rigid squares, or the like can be attached to a flexible layer or fabric that will dissipate received impact energy over the length of the fabric fibers prior to the dissipation of energy by the material 710.

FIGS. 79, 79a, and 82-86 show yet another embodiment of the inventive material of the invention, in which the material comprises two aramid layers 1010, 1012 with an elastomeric layer 1020 therebetween shown in the simpleset configuration in FIG. 19a). The applicant has found that this configuration is an effective padding for high weight or impact resistant configurations because the aramid material layers 1010, 1012, resist impact and discourage displacement of the elastomeric layer 1020. This allows for the use of very low durometer elastomers, rubbers, and gels, with durometers in the hundred to thousand ranges while still providing excellent stability.

Alternately, rather than using aramid layers, other fibers could be used, including high tensile strength fibers.

While other high tensile strength materials could be used, aramids with a tensile modulus of between 70 and 140 GPa are preferred, and nylons such as those with a tensile strength of between 6,000 and 24,000 psi are also preferred. Other material layers and fibers could substitute for the aramid layers 1010, 1012; in particular, low tensile strength fibers could be combined with higher tensile strength fibers to yield layers 1010, 1012 that would be suitable to stabilize and contain the elastomeric layer 1020. For example, cotton, kenaf, hemp, flax, jute, and sisal could be combined with certain combinations of high tensile strength fibers to form the supportive layers 1010, 1012.

In use, the first and second aramid material layers 1010, 1012 are preferably coated with a bonding layer 1010a, 1010b, 1012a, 1012b, preferably of the same material as the elastomeric material that facilitates bonding between the aramid layers 1010, 1012 and the elastomeric layer 1020, although these bonding layers are not required. Further, although equal amounts of the bonding layers 1010a, 1010b, 1012a, 1012b are shown on either side of the aramid layers 1010, 1012, the bonding layers 1010a, 1010b, 1012a, 1012b need not be evenly distributed over the aramid layers 1010, 1012.

The applicant has observed that the aramid layers 1010, 1012 distribute impact and vibration over a larger surface area of the elastomeric layer 1020. This finding has suggested using the material in heavier impact applications, such as using it as a motor mount 1030 or flooring 1035, 1037, since the aramid layers 1010, 1012 will discourage displacement of the elastomeric layer 1020, while still absorbing much of the vibration in those applications. This property could be useful in many of the above-noted applications, and in particular in impact absorbing padding, packaging, electronics padding, noise reducing panels, tape, carpet padding, and floor padding.

Figure 79:
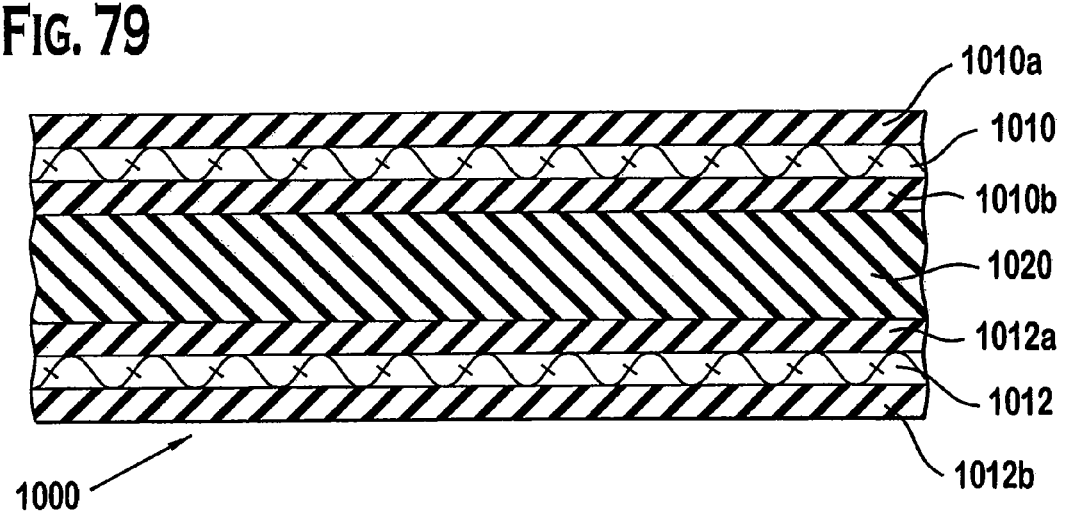
FIG. 79 is a cross-sectional view of another embodiment of the material of the invention.
Figure 79A:
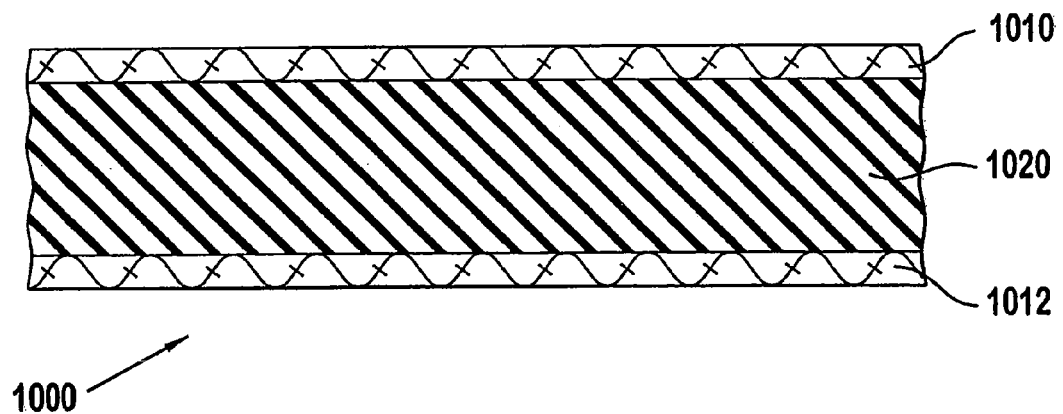
FIG. 79a is a cross-sectional view of another embodiment of the material of the invention.
Figure 80:
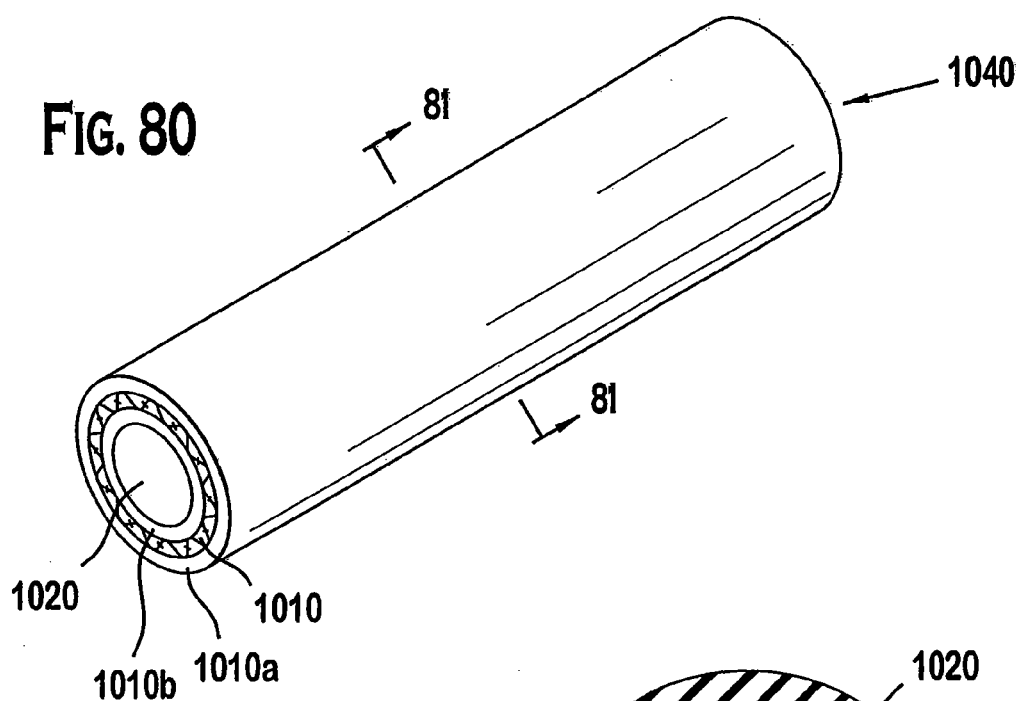
FIG. 80 shows the material of FIG. 80 closed upon itself in a tube.

FIGS. 80, 81, 81a, and 87 show a variant of the material shown in FIG. 79, without the second layer of aramid 1012. The aramid layer 1010 could be coated with the bonding layer 1010a, 1010b or not.

Figure 81:
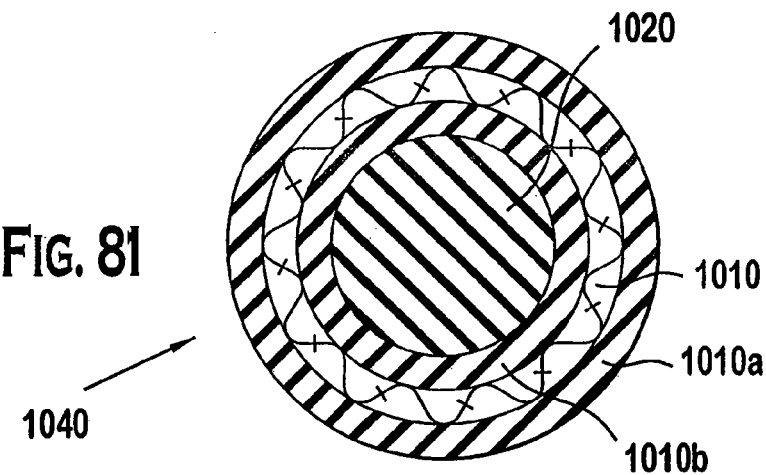
FIG. 81 is a cross section through the lines 81-81 in FIG. 80.
Figure 81A:
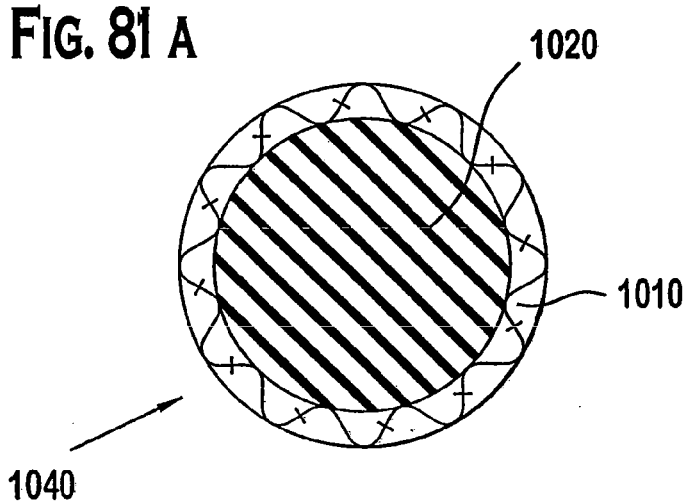
FIG. 81a is an alternate material cross section through the lines 81-81 in FIG. 80.
Figure 82:
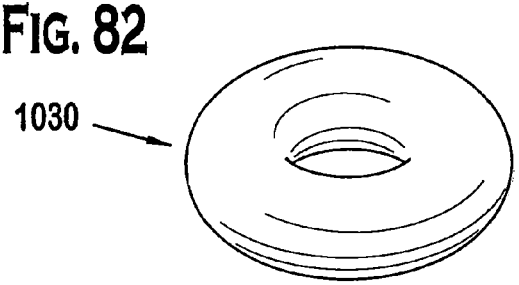
FIG. 82 is a toroidal shaped embodiment of the invention.
Figure 83:
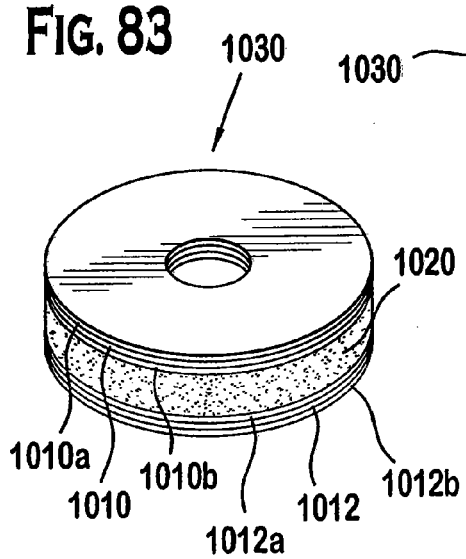
FIG. 83 is an open cylinder-shaped embodiment using the material of the invention.
Figure 84:
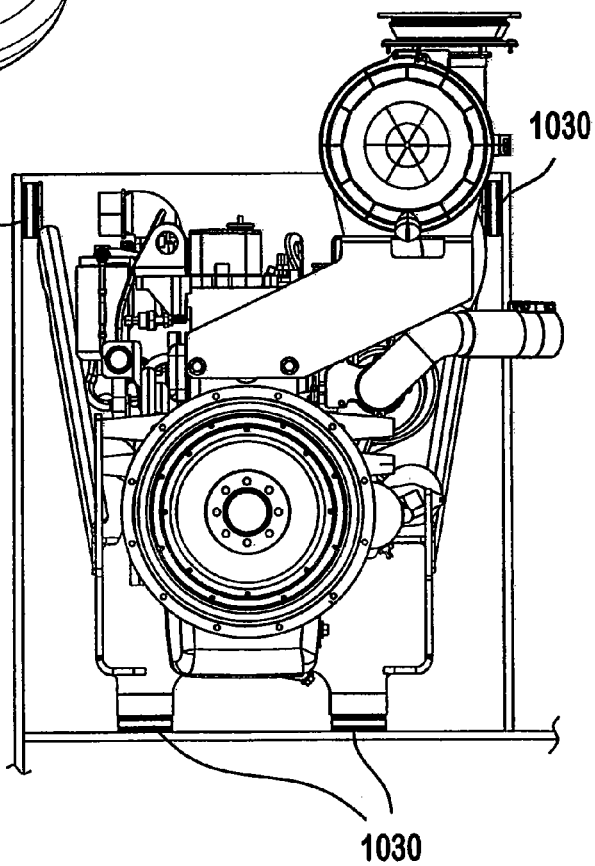
FIG. 84 shows the open cylinder embodiment as applied in an engine mount.
Figure 85:
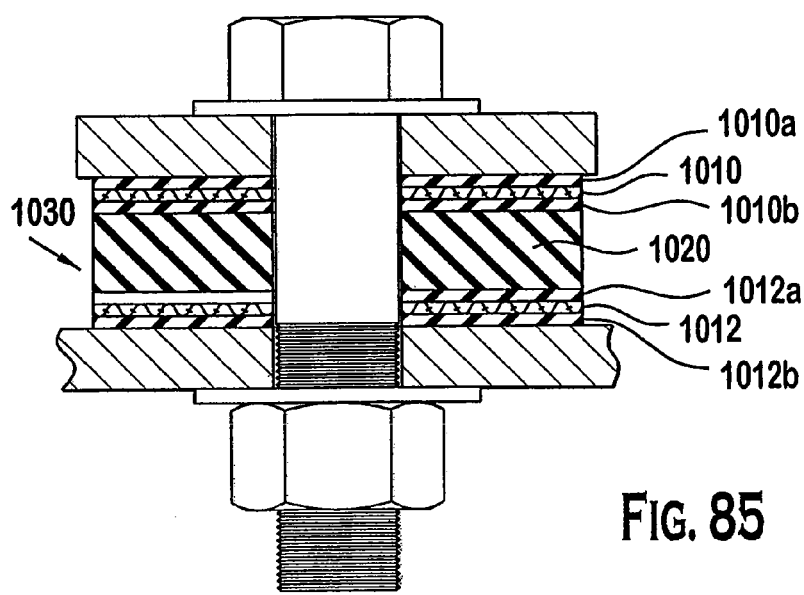
FIG. 85 shows an open cylinder embodiment as applied as a shock absorber.
Figure 86:
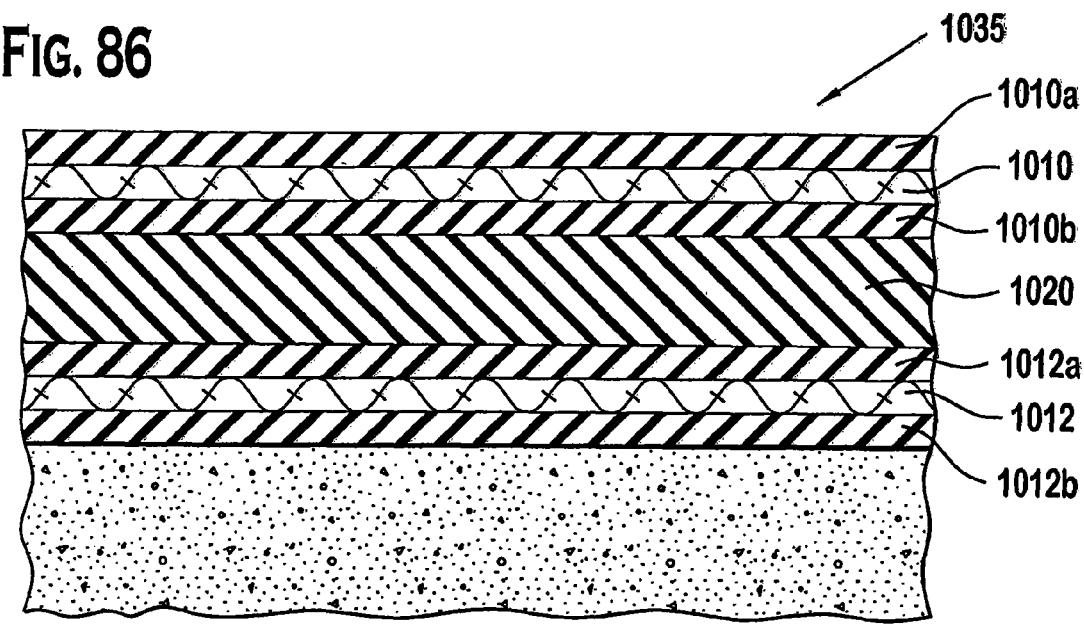
FIGS. 86 and 87 show variant embodiments of the material of FIG. 79 as used in a flooring surface.
Figure 87:
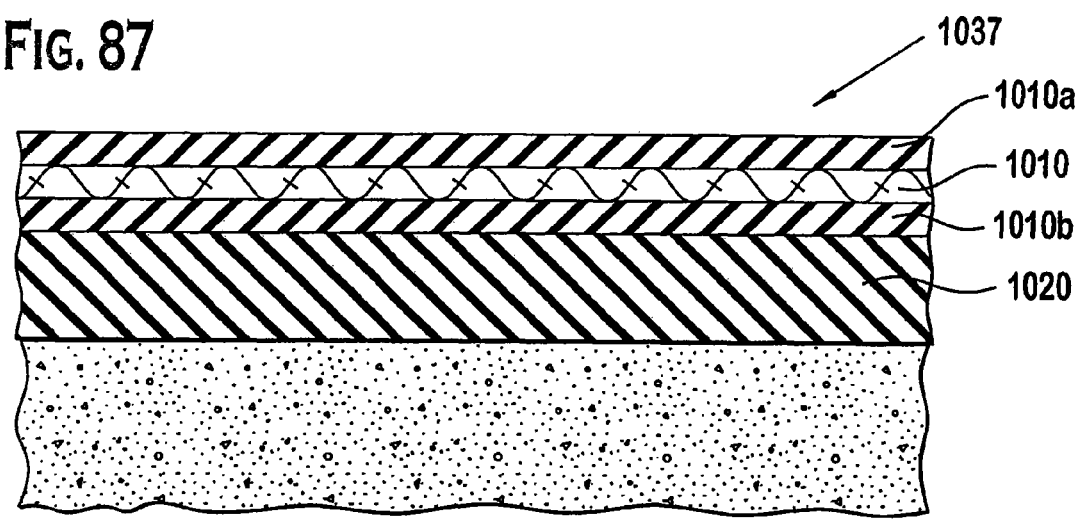
Figure 88:
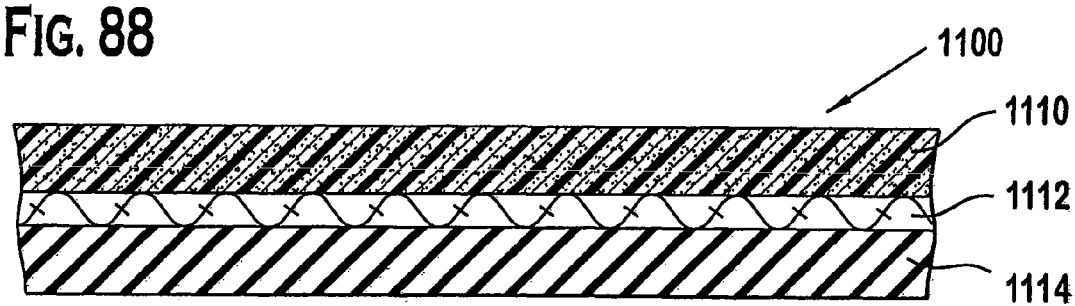
FIG. 88 shows a cross section of another material embodiment of the invention.
Figure 89:
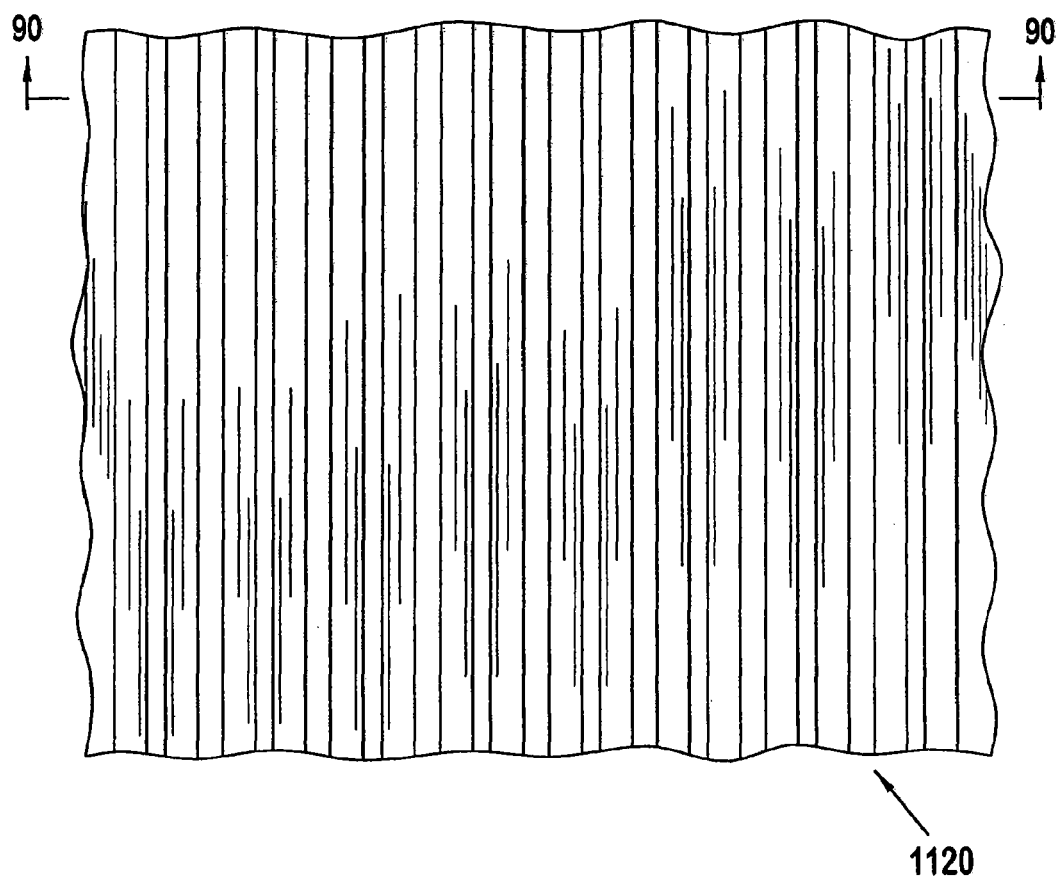
FIG. 89 shows a top view of the material of FIG. 88 with grooves formed therein.

In use, this material can be used as a flooring 1037, as shown in FIG. 87, as a spring in FIG. 81a, or also as a motor mount 1050. As a spring, shown in FIGS. 81 and 81a, the aramid layer 1010 contains and stabilizes the elastomeric layer 1020 when the generally shaped cylinder 1040 is in tension or compression. Such a spring could be used in any spring application.

In use as a motor mount, the material is formed as a cylinder 1040, in which the aramid layer 1010 forms an outer cylinder with an elastomer 1020 located therebetween. This cylinder 1040 is closed on itself (by gluing or welding) to form the toroidal shaped shock absorber 1050, which could be used as a motor mount.

Figure 90:
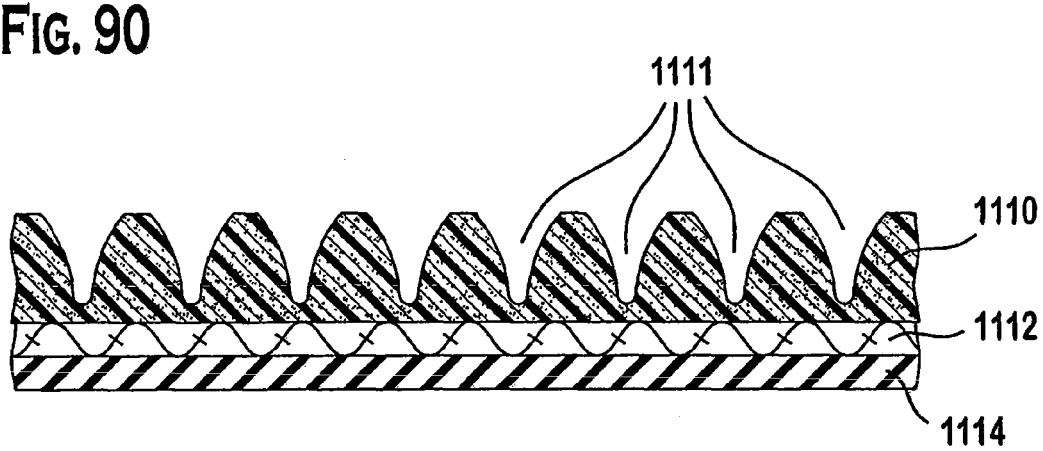
FIG. 90 is a cross section of FIG. 89 along the lines 90-90.
Figure 91:
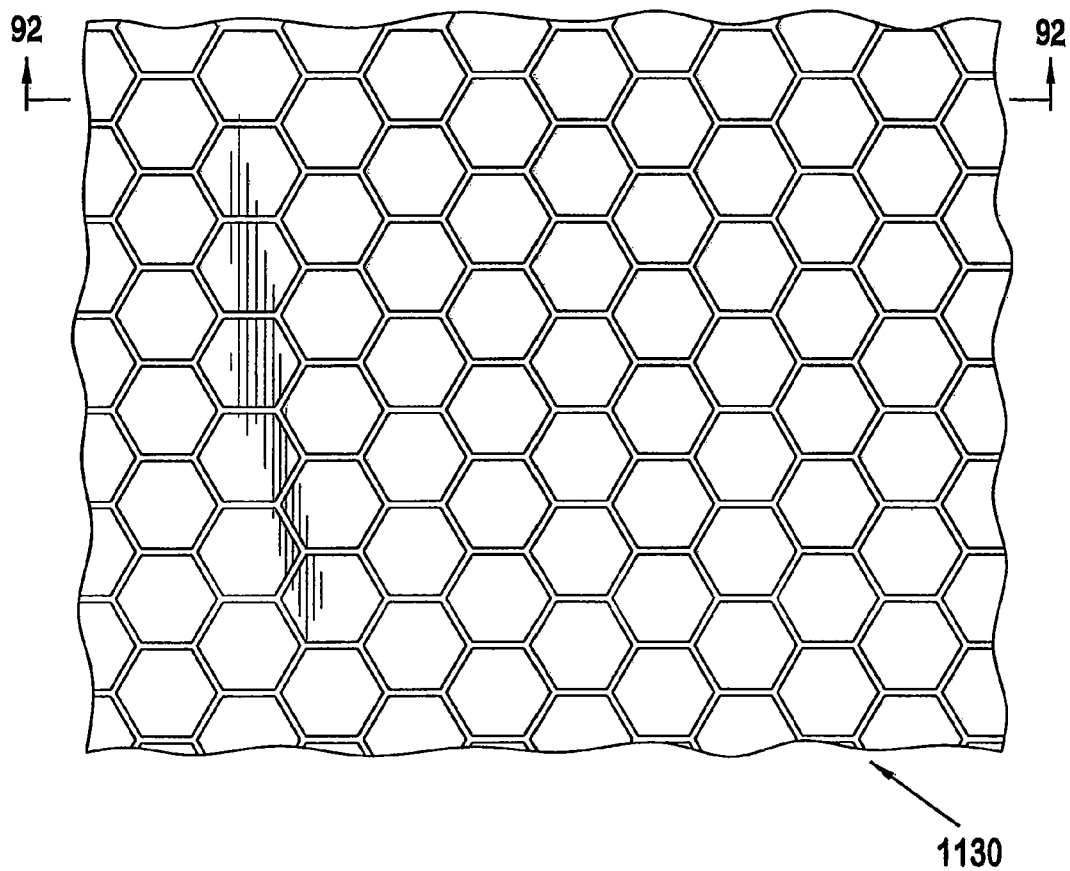
FIG. 91 shows a top view of the material of FIG. 88 with grooves formed therein.
Figure 92:
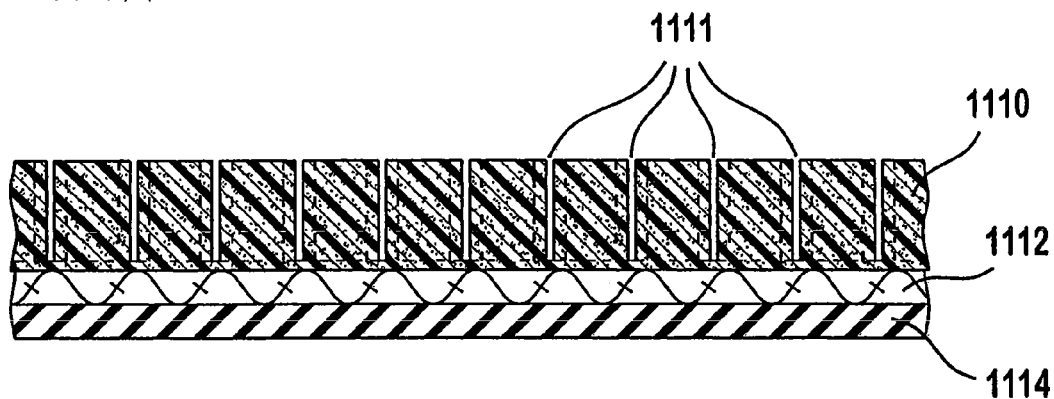
FIG. 92 is a cross section of FIG. 91 along the lines 92-92.

FIGS. 89-93 show another material for use with the invention. The cross-section of FIG. 90 shows the layers of the material, which comprise a foam layer 1110, aramid layer 1112, and elastomeric layer 1114. The foam layer 1110 is a generally rigid layer of foam that the applicant has found is particular good at dissipating a point impact, and thus has been found particular suited for impact resistance, such as for example, as armor and protection in the sports of football, baseball, soccer, or paintball. It should be understood that the elastomeric layer 1114 is generally adjacent to, or substantially adjacent to the body being protected from impact.

Figure 93:
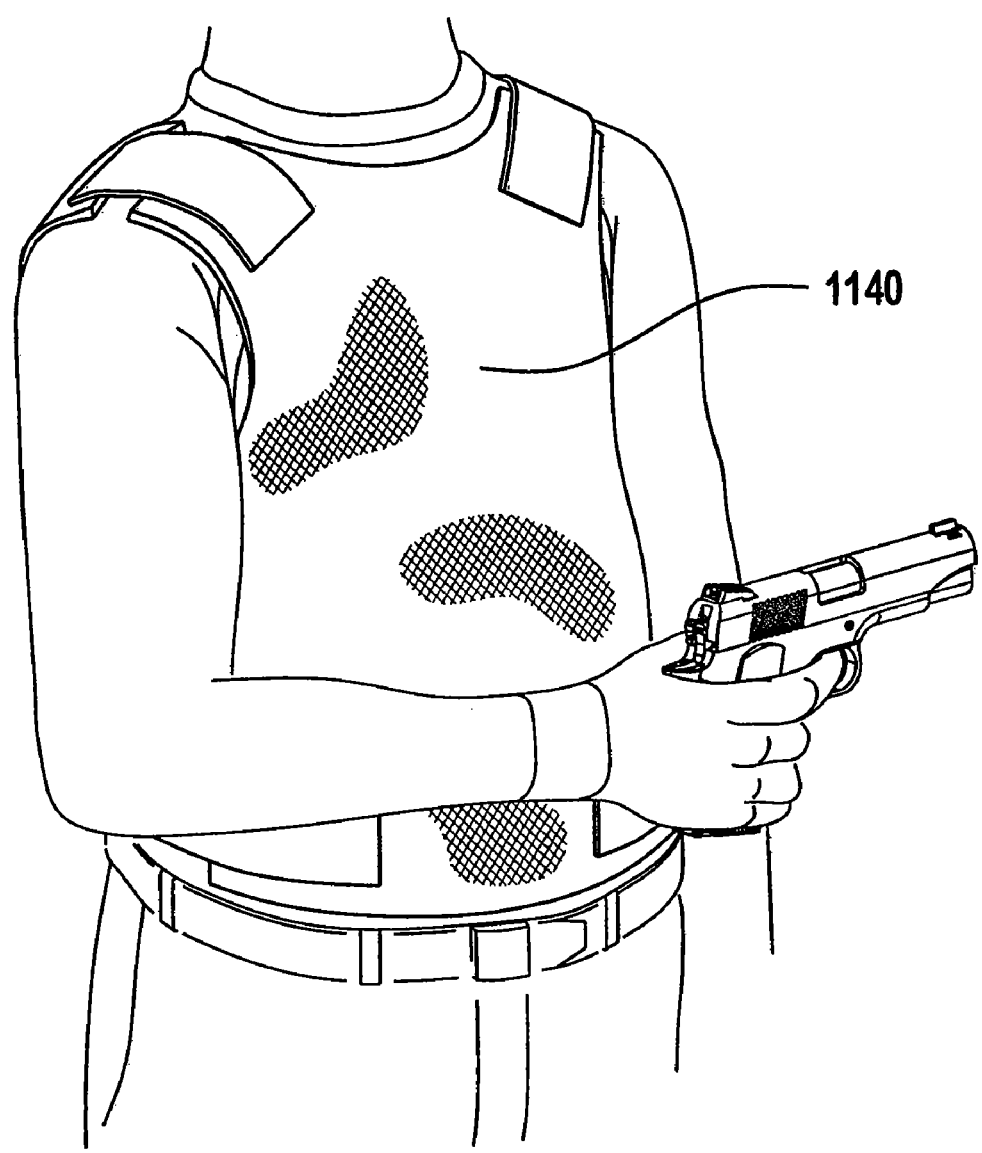
FIG. 93 shows the material of FIG. 88 as used with a protective vest.

The foam layer 1110 is preferably rigid and inflexible, although softer foam layers may be used. The rigid foam layers 1110 present a problem in that many impact-resistant applications require flexible material, i.e., paintball padding and armor that can flex around a person's body. The applicant solved this problem by forming narrow areas of weakness 1111 in the foam layer. These areas can be formed by cutting, stamping, or forming the area of predetermined weakness, but in any event, the allow for the foam layer 1110 to bend at these areas 1111. Various shapes of the areas of predetermined weakness could be used depending on the needed flexibility. As shown, parallel, hexagonal, and herringbone (diamond) areas are presently preferred. FIG. 93 shows an embodiment in which the paintball armor 1140 has the herringbone pattern.

Finally, the applicant has found that a fourth rigid layer comprising plastic, foam, or metal, could be added over the foam/aramid/elastomer to further dissipate impact energy.

It is recognized by those skilled in the art, that changes may be made to the above-described embodiments of the invention without departing from the broad inventive concept thereof. For example, the material 10 may include additional layers (e.g., five or more layers) without departing from the scope of the claimed present invention. It is understood, therefore, that this invention is not limited to the particular embodiments disclosed, but is intended to cover all modifications which are within the spirit and scope of the invention as defined by the appended claims and/or shown in the attached drawings.

What is claimed is:

1. A vibration-reducing material comprising:
   first and second flexible or semi-rigid aramid material layers that distribute vibration to facilitate vibration dampening, each of the first and second aramid material layers including at least some floating fibers and having a cylindrical shape extending between opposed planar end surfaces; and
   an elastomeric layer that is substantially free of voids configured to absorb vibration and impact energy, the elastomer layer having a cylindrical shape and located substantially between one of the planar end surfaces of the first aramid material layer and one of the planar end surfaces of the second aramid material layer.

2. The vibration-reducing material of claim 1, wherein the aramid material layer is a high tensile strength layer.

3. The vibration-reducing material of claim 2, wherein the high tensile strength layer is impact resistant.

4. The vibration-reducing material of claim 2, wherein the high tensile strength layer has a tensile modulus of between 70 and 140 GPa.

5. The vibration-reducing material of claim 2, wherein the high tensile strength layer is coated with a bonding layer that facilitates bonding between the high tensile strength layer and the elastomeric layer.

6. The vibration-reducing material of claim 5, wherein the bonding layer is made from the same material as the elastomeric layer.

7. The vibration-reducing material of claim 6, wherein the high tensile strength fabric layer has two sides, each of which has a coating of the bonding material.

8. The vibration-reducing material of claim 1, used to reduce vibration as a motor mount.

9. The vibration-reducing material of claim 1, used as a spring.

10. The vibration-reducing material of claim 1, used to reduce vibration as an item selected from the group consisting of: impact absorbing padding, flooring, packaging, electronics padding, noise reducing panels, tape, carpet padding, and floor padding.

11. The vibration-reducing material of claim 1, wherein the vibration-reducing material is chemical resistant.

12. The vibration-reducing material of claim 1, wherein the cylinder is closed onto itself to form a toroidal shape.

13. A motor mount made with the material of claim 12.

14. A spring made with the material of claim 12.

15. The vibration-reducing material of claim 1, wherein the aramid material has a tensile strength between 6,000 and 24,000 psi.

* * * * *